US008101351B2

(12) United States Patent
Maertens et al.

(10) Patent No.: US 8,101,351 B2
(45) Date of Patent: *Jan. 24, 2012

(54) PROCESS FOR TYPING OF HCV ISOLATES

(75) Inventors: Geert Maertens, Bruges (BE); Lieven Stuyver, Herzele (BE); Rudi Rossau, Ekeren (BE); Hugo Van Heuverswyn, Laame (BE)

(73) Assignee: Innogenetics N.V., Ghent (BE)

( * ) Notice: Subject to any disclaimer, the term of this patent is extended or adjusted under 35 U.S.C. 154(b) by 1110 days.

This patent is subject to a terminal disclaimer.

(21) Appl. No.: 11/826,099

(22) Filed: Jul. 12, 2007

(65) Prior Publication Data

US 2010/0120121 A1    May 13, 2010

Related U.S. Application Data

(60) Division of application No. 10/412,290, filed on Apr. 14, 2003, now Pat. No. 7,258,977, which is a continuation of application No. 09/899,044, filed on Jul. 6, 2001, now Pat. No. 6,548,244, which is a division of application No. 09/378,900, filed on Aug. 23, 1999, now Pat. No. 6,495,670, which is a division of application No. 09/044,665, filed on Mar. 19, 1998, now Pat. No. 6,051,696, which is a division of application No. 08/256,568, filed as application No. PCT/EP93/03325 on Nov. 26, 1993, now Pat. No. 5,846,704.

(30) Foreign Application Priority Data

Nov. 27, 1992 (EP) ..................................... 92403222
Aug. 31, 1993 (EP) ..................................... 93402129

(51) Int. Cl.
C12Q 1/68 (2006.01)
C07H 21/00 (2006.01)
C07H 21/02 (2006.01)
C07H 21/04 (2006.01)

(52) U.S. Cl. ........ 435/6.1; 536/22.1; 536/23.1; 536/24.3
(58) Field of Classification Search ........... 435/6, 235.1; 536/22.1, 23.1, 24.3, 24.32
See application file for complete search history.

(56) References Cited

U.S. PATENT DOCUMENTS

| 5,043,272 | A |   | 8/1991  | Hartley |
|-----------|---|---|---------|---------|
| 5,077,193 | A |   | 12/1991 | Mishiro et al. |
| 5,176,994 | A |   | 12/1992 | Moshiro et al. |
| 5,252,743 | A |   | 10/1993 | Barrett et al. |
| 5,372,928 | A |   | 12/1994 | Miyamura et al. |
| 5,410,068 | A | * | 4/1995  | Coull et al. .................... 548/545 |
| 5,427,909 | A |   | 6/1995  | Okamoto et al. |
| 5,428,145 | A |   | 6/1995  | Okamoto et al. |
| 5,459,034 | A | * | 10/1995 | Tabaqchali et al. ............... 435/6 |
| 5,527,669 | A |   | 6/1996  | Resnick et al. |
| 5,550,016 | A |   | 8/1996  | Okamoto et al. |
| 5,620,852 | A |   | 4/1997  | Lin et al. |
| 5,629,153 | A |   | 5/1997  | Urdea |
| 5,629,158 | A |   | 5/1997  | Uhlen et al. |
| 5,846,704 | A | * | 12/1998 | Maertens et al. .................. 435/5 |
| 5,871,903 | A |   | 2/1999  | Miyamura et al. |
| 6,051,696 | A | * | 4/2000  | Maertens et al. ............ 536/23.1 |
| 6,171,784 | B1 |  | 1/2001  | Maertens et al. |
| 6,190,864 | B1 |  | 2/2001  | Cha |
| 6,297,370 | B1 |  | 10/2001 | Cha et al. |
| 6,495,670 | B1 | * | 12/2002 | Maertens et al. ............ 536/23.1 |
| 6,548,244 | B2 | * | 4/2003  | Maertens et al. .................. 435/5 |
| 7,157,226 | B1 | * | 1/2007  | Maertens et al. .................. 435/6 |
| 7,258,977 | B1 | * | 8/2007  | Maertens et al. .................. 435/6 |
| 7,855,052 | B2 | * | 12/2010 | Maertens et al. .................. 435/6 |

FOREIGN PATENT DOCUMENTS

| EP | 0461863      | 12/1991 |
| EP | 0469348      | 2/1992  |
| EP | 0 531 974 A1 | 3/1993  |
| EP | 529493 A2    | 3/1993  |
| WO | WO 92/02642  | 2/1992  |
| WO | WO92/10588   | 6/1992  |
| WO | WO 92/19743  | 11/1992 |
| WO | WO 93/23569  | 11/1993 |

OTHER PUBLICATIONS

Sommer et al., Minimal homology requirements for PCR primers. Nucleic Acids Research 17(16): 6749 (1989).*
Simmonds et al, J. of General Virology 74: 661-668 (1993).
Chan et al, J. of General Virology 73: 1131-1141 (1992).
Okamoto et al, J. of General Virology 7: 2697-2704 (1991).
Ogata et al, PNAS (USA) 88: 3392-3396 (1991).
Enomoto et al, Biochemical Biophysical Research Communications 170(3): 121-1025 (1990).
Choo et al, PNAS (USA) 88: 2451-2455 (1991).
Okamoto et al., Japanese J. of Experimental Medicine 60 : 167-177 (1990).
Bukh et al., PNAS 89 :4942-4946 (1992).
Okamoto et al., J. of General Virology 72 : 2697-2704 (1991).
Okamoto et al., Virology 188 :331-341 (1992).
Cha et al., PNAS 89 : 7144-7148 (1992).
Inchaupse et al., Hepatology 14 : 595-600 (1991).
Weiner et al., Lancet 335 : 1-3 (1990).

(Continued)

Primary Examiner — E C Whisenant
(74) Attorney, Agent, or Firm — Nixon & Vanderhye P.C.

(57) ABSTRACT

The invention relates to a process for genotyping any HCV isolate present in a biological sample, previously identified as being HCV positive, and for classifying said isolate according to the percentage of homology with other HCV isolates, comprising the steps of:
  contacting said sample in which the ribonucleotides or deoxyribonucleotides have been made accessible, if need be, under suitable denaturation, with at least one probe from about 10 to about 40 nucleotides, with said probe being liable to hybridize to a region being in the domain extending from nucleotide at position −291 to nucleotide at position −66 of the 5' untranslated region of one of the HCV isolates represented by their cDNA sequences, with said numbering of position beginning with the first ATG codon of the open reading frame encoding the HCV polyprotein, or with said probe being complementary to the above-defined probes,
  detecting the complexes possibly formed between said probe and the nucleotide sequence of the HCV isolate to be identified.

9 Claims, 14 Drawing Sheets

OTHER PUBLICATIONS

Lee et al., J. of Clinical Microbiology 30 : 1602-1604 (1992).
Cha et al., J. of Clincal Microbiology 29(11):2528-2534 (1991).
Hu et al., J. Clin. Invest. 89, 2040-2045 (1992).
Nakao et al., J. of General Virology 72: 2105-2112 (1991).
Nedjar (1991) J. Virological Methods 35, 297-304.
Martell (1992) J. Virol. 66, 3225-3229.
Sommer et al., (1989) Nucleic Acids Research 17, 6749.
Okamoto, J. Gen. Virol., 73, No. 3, Mar. 1992, pp. 673-679.
Takamizawa, J. Virol. 65, 1105-1113 (1991).
Okamoto, J. Gen. Virol. 72, 2697-2704 (1991).
Castillo et al. (1992) Journal of Virological Methods, vol. 38, No. 1, pp. 71-79.
Stuyver et al, "Typing of hepatitis C virus isolates and characterization of new subtypes using a line probe assay", Journal of General Virology (1993), vol. 74, pp. 1093-1102.
Press Release, Sep. 29, 2005, Innogenetics takes legal action to enforce its HCV patent portfolio.
"Expert Report of Bruce K. Patterson, M.D. Regarding the invalidity of Innogenetics, N.V.'s U.S. Patent No. 5,846,704", signed Apr. 10, 2006 (33 pages with 14 page Exhibit A Curriculum Vitae, 2 page Exhibit B, 2 page Exhibit C, 2 page Exhibit D).
Bukh et al, "Importance of primer selection for the detection of hepatitis C virus RNA with the polymerase chain reaction assay", PNAS 89:187-191 (Jan. 1992).
Complaint for Patent Infringement *Innogenetics v. Third Wave Technologies Inc.*, U.S District Court for the Western District of Wisconsin, Case No. 05C 0574 C, Filed Sep. 29, 2005.
TWT's Answer, Affirmative Defenses and Counterclaim. *Innogenetics v. Third Wave Technologies Inc.*, U.S. District Court for the Western District of Wisconsin, Case No. 05C 0574 C, Filed Sep. 29, 2005.
TWT's Supplemental Objections and Responses to Innogenetics' First Set of Interrogatories (Nos. 1-10); More Specifically See the List on pp. 6-7. U.S. District Court for the Western District of Wisconsin, Case No. 05C 0574 C, Filed Sep. 29, 2005.
Plaintiff'S Responses to Third Wave Technologies, Inc.'S First Set of Interrogatories (Nos. 1-11) to Innogenetics N. V.: See Specifically Response to No. 9. U.S. District Court for the Western District of Wisconsin, Case No. 05C 0574 C, Filed Sep. 29, 2005.
Stipulation and Order for Dismissal. U.S. District Court for the Western District of Wisconsin, Case No. 05C 0574 C, Filed Sep. 29, 2005.
Complaint—Summons Issued. U.S. District Court for the Western District of Wisconsin, Case No. 05C 0575 C, Filed Sep. 29, 2005.
Answer U.S. District Court for the Western District of Wisconsin, Case No. 05C 0575 C, Filed Sep. 29, 2005.
Counterclaim and Affirmative Defenses of Deft. U.S. District Court for the Western District of Wisconsin, Case No. 05C 0575 C, Filed Sep. 29, 2005.
Plaintiff'S First Set of Interrogatories U.S. District Court for the Western District of Wisconsin, Case No. 05C 0575 C, Filed Sep. 29, 2005.
Abbott'S First Set of Interrogatories U.S. District Court for the Western District of Wisconsin, Case No. 05C 0575 C, Filed Sep. 29, 2005.
Abbott's First Set of Requests for Admission U.S. District Court for the Western District of Wisconsin, Case No. 05C 0575 C, Filed Sep. 29, 2005.
Answer to Counterclaim by Pltf. U.S. District Court for the Western District of Wisconsin, Case No. 05C 0575 C, Filed Sep. 29, 2005.
Abbott Laboratories' Answers to Innogenetics First Set of Interrogatories U.S. District Court for the Western District of Wisconsin, Case No. 05C 0575 C, Filed Sep. 29, 2005.
Plaintiff's Responses to Abbott Laboratories' First Set of Requests for Admission U.S. District Court for the Western District of Wisconsin, Case No. 05C 0575 C, Filed Sep. 29, 2005.
Plaintiff'S Responses to Defendant Abbott Laboratories' First Set of Interrogatories U.S. District Court for the Western District of Wisconsin, Case No. 05C 0575 C, Filed Sep. 29, 2005.
Deposition of Charles A. Muserlian, Taken Jan. 11, 2006. (*Muselian was the US corresponding attorney during prosecution for the '704 patent.*) U.S. District Court for the Western District of Wisconsin, Case Nos. 05C 0574C & 05C 0575 C, Filed Sep. 29, 2005.
Plaintiffs First Set of Requests for Admission U.S. District Court for the Western District of Wisconsin, Case No. 05C 0575 C, Filed Sep. 29, 2005.
Abbott'S First Supplemental Answers to Innogenetics' First Set of Interrogatories U.S District Court for the Western District of Wisconsin, Case No. 05C 0575 C, Filed Sep. 29, 2005.
Abbott Laboratories' Motion to Compel Full and Complete Interrogatory Responses From Innogenetics, N.V. U.S. District Court for the Western District of Wisconsin, Case No. 05C 0575 C, Filed Sep. 29, 2005.
Abbott Laboratories' Brief in Support of Its Motion to Compel Full and Complete Interrogatory Responses From Innogenetics, N.V. U.S. District Court for the Western District of Wisconsin, Case No. 05C 0575 C, Filed Sep. 29, 2005.
Brief in Opposition by Pltf. to Deft. Motion to Compel. U.S. District Court for the Western District of Wisconsin, Case No. 05C 0575 C. Filed Sep. 29, 2005.
Affidavit of Lissa R Koop. U.S. District Court for the Western District of Wisconsin. Case No. 05C 0575 C, Filed Sep. 29, 2005.
Abbott's Reply Brief in Support of Its Motion to Compel Full and Complete Interrogatory Responses From Innogenetics U.S. District Court for the Western District of Wisconsin, Case No. 05C 0575 C, Filed Sep. 29, 2005.
Transcript of Telephone Motion Hearing, Held Mar. 22, 2006. (E-Notice: Skilton, Carter) U.S. District Court for the Western District of Wisconsin, Case No. 05C 0575 C, Filed Sep. 29, 2005.
Abbott's Third Supplemental Answers to Innogenetics' First Set of Interrogatories U.S. District Court for the Western District of Wisconsin, Case No. 05C 0575 C, Filed Sep. 29, 2005.
Expert Report of Devanand John Crease. Signed Apr. 10, 2006.
Expert Report of Howard J. Worman. U.S District Court for the Western District of Wisconsin, Case No. 06C 0575 C, Filed Sep. 29, 2005 *signed* Apr. 10, 2006.
Abbott's Second Set of Interrogatories U.S District Court for the Western District of Wisconsin, Case No. 05C 0575 C, Filed Sep. 29, 2005.
Proffer of Written Testimony of Dr. Geert Maertens Re. Topic 11 of Deft. First Notice of Deposition. (filed under Seal at the district court) Redact p. 6, section 24-26 U.S. District Court for the Western District of Wisconsin, Case No. 05C 0575 C, Filed Sep. 29, 2005.
Expert Report of Howard J. Worman (Second) U.S. District Court for the Western District of Wisconsin, Case No. 05C 0575 C, Filed Sep. 29, 2005 Signed May 2, 2006.
Expert Report of William S. Reznikoff on Validity in View of the CHA PCT Application. U.S. District Court for the Western District of Wisconsin, Case No. 05C 0575 C, Filed Sep. 29, 2005 Signed May 2, 2006.
Expert Report of Michael Sofocleous. U.S. District Count for the Western District of Wisconsin, Case No. 05C 0575 C, Filed Sep. 29, 2005 Signed May 2, 2006.
Plaintiff'S First Supplemental Responses to Defendant Abbott Laboratories' First Set of Interrogatories . U.S. District Court for the Western District of Wisconsin, Case No. 05C 0575 C, Filed Sep. 29, 2005.
Motion for Summary Judgment of No Inequitable Conduct by Pltf. U.S. District Court for the Western District of Wisconsin, Case No. 05C 0575 C, Filed Sep. 29, 2005.
Brief in Support of Pltf. Motion for S/J of No Inequitable Conduct. U S District Court for the Western District of Wisconsin, Case No. 05C 0575 C, Filed Sep. 29, 2005.
Proposed Findings/Concl. by Pltf. U.S. District Court for the Western District of Wisconsin, Case No. 05C 0575 C, Filed Sep. 29, 2005.
Affidavit of Melody K. Glazer. U.S. District Court for the Western District of Wisconsin, Case No. 05C 0575 C, Filed Sep. 29, 2005.
Motion for Summary Judgment by Deft. U.S. District Court for the Western District of Wisconsin, Case No. 05C 0575 C, Filed Sep. 29, 2005.
Brief in Support of Deft. Motion for Summary Judgment. U.S. District Court for the Western District of Wisconsin, Case No. 05C 0575 C, Filed Sep. 29, 2005.
Proposed Findings/Concl. by Deft. U.S. District Court for the Western District of Wisconsin, Case No. 05C 0575 C, Filed Sep. 29, 2005.

Affidavit of Devanand J. Crease. Affidavit of Devanand J. Crease—vol. 2. U.S. District Court for the Western District of Wisconsin, Case No. 05C 0575 C, Filed Sep. 28, 2005.
Affidavit of Bruce K Patterson, M.D. U.S. District Court for the Western District of Wisconsin, Case No. 05C 0575 C, Filed Sep. 29, 2005.
Supplement to Expert Report of Bruce K Patterson, M.D. Re: Invalidity of Innogenetics '704 Patent U.S. District Court for the Western District of Wisconsin, Case No. 05C 0575 C, Filed Sep. 29, 2 2005.
Motion by Pltf. to Strike Supplemental Expert Report of Bruce K. Patterson, M.D. U.S. District Court for the Western District of Wisconsin, Case No. 05C 0575 C, Filed Sep. 29, 2005.
Brief in Support of Pltf.. Motion to Strike Supplemental Expert Report of Bruce K. Patterson. U.S. District Court for the Western District of Wisconsin, Case No. 05C 0575 C, Filed Sep. 29, 2005.
Abbott's Fourth Supplemental Answers to Innogenetics' First Set of Interrogatories U.S. District Court for the Western.District of Wisconsin, Case No. 05C 0575 C, Filed Sep. 29, 2005.
Brief in Opposition by Deft. to Pltf. Motion to Strike Supplement to Expert Report of Bruce K. Patterson. U.S. District Court for the Western District of Wisconsin, Case No. 05C 0575 C, Filed Sep. 29, 2005.
Brief in Opposition by Pltf. to Deft. Motion for S/J of Inequitable Conduct. U.S. District Court for the Western District of Wisconsin, Case No. 05C 0575 C, Filed Sep. 29, 2005.
Affidavit of Melody K Glazer in Support of Deft. Brief in Opposition to Deft. Motion for S/J of Inequitable Conduct. U.S. District Court for the Western District of Wisconsin, Case No. 05C 0575 C, Filed Sep. 29, 2005.
Brief in Opposition by Deft. to Pltf. Motion for S/J of No Inequitable Conduct. U.S. District Court For the Western District of Wisconsin, Case No. 05C 0575 C, Filed Sep. 29, 2005.
Response to Proposed S/J Findings/Concl. by Deft. to Pltf. Motion for S/J. U.S. District Court for the Western District of Wisconsin, Case No. 05C 0575 C, Filed Sep. 29, 2005.
Brief in Opposition by Pltf. to Deft. Motion for S/J. (filed under Seal at the district court) U.S. District Court for the Western District of Wisconsin, Case No. 05C 0575 C, Filed Sep. 29, 2005.
Response to Proposed S/J Findings/Concl. by Pltf. (Sealed) U.S. District Court for the Western District of Wisconsin, Case No. 05C 0575 C, Filed Sep. 29, 2005.
Proposed Findings/Concl. by Pltf. (Sealed) U.S. District Court for the Western District of Wisconsin, Case No. 05C 0575 C. Filed Sep. 29, 2005.
Affidavit of Howard J. Worman. U.S. District Court for the Western District of Wisconsin. Case No. 05C 0575 C, Filed Sep. 29, 2005.
Brief in Opposition (Corrected) by Pltf. to Deft. Motion for S/J (filed under SEAL at the district court) U.S. District Court for the Western District of Wisconsin, Case No. 05C 0575 C, Filed Sep. 29, 2005.
Deposition of Ann De Clercq, Taken Mar. 22, 2006. U.S. District Court for the Western District of Wisconsin, Case No. 05C 0575 C, Filed Sep. 29, 2005.
Deposition of Catherine Grosset-Fournier, Taken Mar. 21, 2006. U.S. District Court for the Western District of Wisconsin Case No. 05C 0575 C, Filed Sep. 29, 2005.
Brief in Reply in Support of Pltf. Motion for S/J of No Inequitable Conduct. U.S. District Court for the Western District of Wisconsin, Case No. 05C 0575 C, Filed Sep. 29, 2005.
Affidavit of Melody K. Glazer. U.S. District Court for the Western District of Wisconsin. Case No. 05C 0575 C, Filed Sep. 29, 2005.
Brief in Reply in Support of Deft. Motion for S/J. U.S. District Court for the Western District of Wisconsin, Case No. 05C 0575 C, Filed Sep. 29, 2005.
Deposition of Devanand John Crease, Taken Apr. 24, 2006. U.S. District Court for the Western District of Wisconsin, Case No. 05C 0575 C, Filed Sep. 29, 2005.
Deposition of Howard J. Worman, Taken Apr. 28, 2006. U.S. District Court for the Western District of Wisconsin, Case No. D5C 0575 C, Filed Sep. 29, 2005.
Motion by Pltf. to Strike Deft. New Construction of Claim "Method of Genotyping" or Leave to Reply to New Construction. U.S. District Court for the Western District of Wisconsin, Case No. 05C 0575 C, Filed Sep. 29, 2005.

Brief in Support of Pltf. Motion to Strike Deft. New Construction of Claim "Method of Genotyping" or Leave to Reply. U.S. District Court for the Western District of Wisconsin, Case No. 05C 0575 C, Filed Sep. 29, 2005.
Affidavit of Melody K. Glazer in Support of Pltf. Motion to Strike Deft. New Term Method of Genotyping. U.S. District Court for the Western District of Wisconsin. Case No. 05C 0575 C. Filed Sep. 29, 2005.
Innogenetics Second Set of Requests for Admission U.S. District Court for the Western District of Wisconsin, Case No. 05C 0576 C, Filed Sep. 29, 2005.
Brief in Opposition by Deft. to Pltf. Motion to Strike Deft. New Claim Construction and Argument Re: S/J Reply Brief. U.S. District Court for the Western District of Wisconsin, Case No. 05C 0575 C, Filed Sep. 29, 2005.
Order Granting Pltf S/J Mot Re No Inequitable Conduct: Deft S/J Mot Denied: Brfg Set on Fees/Costs Re Inequitable Conduct. U.S. District Court for the Western District of Wisconsin, Case No. 05C 0575 C, Filed Sep. 29, 2005.
Motion by Deft for Leave to Supplement Proposed Findings of Fact in Support of S/J Motion. U.S. District Court for the Western District of Wisconsin. Case No. 05C 0575 C, Filed Sep. 29, 2005.
Innogenetics' Second Supplemental Responses to Abbott'S First Set of Interrogatories U.S. District Court for the Western District of Wisconsin, Case No. 05C 0575 C. Filed Sep. 29. 2005.
Abbotts Fifth Supplemental Answers to Innogenetics' First Set of Interrogatories U.S. District Court for the Western District of Wisconsin, Case No. 05C 0575 C, Filed Sep. 29, 2005.
Innogenetics' Responses to Defendant Abbott Laboratories' Supplemental Proposed Findings of Fact in Support of Its Motion for Summary Judgment U.S. District Court for the Western District of Wisconsin, Case No. 05C 0575 C, Filed Sep. 29, 2005.
Declaration of David L. Anstaett in Support of Plaintiff's Responses to Defendant Abbott Laboratories' Supplemental Proposed Findings of Fact in Support of Its Motion for Summary Judgment U.S District Court for the Western District of Wisconsin, Case No. 05C 0575 C. Filed Sep. 29, 2005.
Defendant Abbott Laboratories' Motion for Reconsideration of Exceptional Case Finding Under 35 U.S.C. § 285 U.S. District Court for the Western District of Wisconsin, Case No. 05C 0575 C. Filed Sep. 29, 2005.
Defendant Abbott Laboratories' Brief Supporting Its Motion for Reconsideration of Exceptional Case Finding Under 35 U.S.C. § 285 U.S. District Court for the Western District of Wisconsin, Case No. 05C 0575 C, Filed Sep. 29, 2005.
Deposition of Howard J. Worman, Taken Jul. 21, 2006 U.S. District Court for the Western District of Wisconsin, Case No. 05C 0575 C, Filed Sep. 29, 2005.
Abbott's Notice Pursuant to 35 U.S.C. § 282 U.S. District Court for the Western District of Wisconsin, Case No. 05C 0575 C, Filed Sep. 29, 2005.
Abbott's Amended Notice,Pursuant to 35 U.S.C. § 282 U.S. District Court for the Western District of Wisconsin, Case No: 05C 0575 C, Filed Sep. 29, 2005.
Order Granting in Part/Denying in Part Pltf. Mot./Strike Supplmtl. Expert Report of Dr. Patterson; Fees and Costs Denied U.S. District Court for the Western District of Wisconsin, Case No. 05C 0575 C, Filed Sep. 29, 2005.
Abbott'S Responses to Innogenetics Second Set of Requests for Admissions U.S. District Court for the Western District of Wisconsin, Case No. 05C 0575 C, Filed Sep. 29, 2005.
Brief in Support of Deft. Motion in Limine to Preclude Reference to S/J Decision. U.S District Court for the Western District of Wisconsin, Case No. 05C 0575 C, Filed Sep. 29, 2005.
Motion in Limine by Deft to Exclude Evidence That Invention is Pioneering. U S. District Court for the Western District of Wisconsin, Case No. 05C 0575 C, Filed Sep. 29, 2005.
Brief in Support of Deft. Motion in Limine to Exclude Evidence That Invention Is Pioneering. U.S District Court for the Western District of Wisconsin, Case No. 05C 0575 C, Filed Sep. 29, 2005.
Motion in Limine by Deft. to Exclude Evidence Relating to '944 Patent. U.S District Court for the Western District of Wisconsin, Case No. 05C 0575 C, Filed Sep. 29, 2005.

Brief in Support of Deft. Motion in Limine to Exclude Evidence Relating to '944 Patent. U.S. District Court for the Western District of Wisconsin, Case No. 05C 0575 C, Filed Sep. 29, 2005.

Motion in Limine by Deft. to Exclude Evidence That Claimed Method of Genotyping Requires Using Multiple Probes. U.S. District Court for the Western District of Wisconsin, Case No. 05C 0575 C, Filed Sep. 29, 2005.

Brief in Support of Deft. Motion in Limine to Exclude Evidence Re: Method of Genotyping. U.S. District Court for the Western District of Wisconsin, Case No. 05C 0575 C, Filed Sep. 29, 2005.

Motion in Limine by Deft. to Exclude Reference to Licensing Agreement Re: 704 Patent. U.S. District Court for the Western District of Wisconsin, Case No. 05C 0575 C. Filed Sep. 29, 2005.

Brief in Support of Deft. Motion in Limine to Exclude Reference to Licensing Agreement Re: '704 Patent. U.S. District Court for the Western District of Wisconsin, Case No. 05C 0575 C, Filed Sep. 29, 2005.

Motion in Limine by Deft. to Exclude Evidence of Patent Law. U.S. District Court for the Western District of Wisconsin, Case No. 05C 0575 C, Filed Sep. 29, 2005.

Brief in Support of Deft. Motion in Limine to Exclude Evidence of Patent Law. U.S. District Court for the Western District of Wisconsin, Case No. 05C 0575 C, Filed Sep. 29, 2005.

Proposed Jury Instructions by Deft. Re: Liability. U.S District Court for the Western District of Wisconsin, Case No. 05C 0575 C, Filed Sep. 29, 2005.

Proposed Special Verdict by Deft. Re: Liability. U.S. District Court for the Western District of Wisconsin, Case No. 05C 0575 C, Filed Sep. 29, 2005.

Motion in Limine by Pltf. to Exclude Testimony of Bruce Patterson Re: Obviousness. U.S. District Court for the Western District of Wisconsin, Case No. 05C 0575 C, Filed Sep. 29, 2005.

Motion in Limine by Pltf. to Exclude Evidence of Prosecution of European Patent. U.S. District Court for the Western District of Wisconsin, Case No. 05C 0575 C, Filed Sep. 29, 2005.

Motion in Limine by Pltf. to Exclude Testimony of Bruce Patterson Re: Anticipation. U.S. District Court for the Western District of Wisconsin, Case No. 05C 0575 C, Filed Sep. 29, 2005.

Motion in Limine by Pltf. to Exclude Testimony of Tai-An Cha and Thomas White. U.S. District Court for the Western District of Wisconsin, Case No. 05C 0575 C, Filed Sep. 29, 2005.

Motion in Limine by Pltf. to Exclude Deft Section 112 Defenses. U.S. District Court for the Western District of Wisconsin, Case No. 05C 0575 C, Filed Sep. 29, 2005.

Brief in Opposition by Pltf. to Deft. Motion for Reconsideration of Exceptional Case. U.S. District Court for the Western District of Wisconsin, Case No. 05C 0575 C, Filed Sep. 29, 2005.

Proposed Jury Instructions by Pltf. Re: Liability. U.S. District Court for the Western District of Wisconsin, Case No. 05C 0575 C, Filed Sep. 29, 2005.

Proposed Special Verdict by Pltf. Re: Liability. U.S. District Court for the Western District of Wisconsin, Case No. 05C 0575 C, Filed Sep. 29, 2005.

Motion in Limine by Deft. to Exclude Testimony From William S. Reznikoff on Validity. U.S. District Court for the Western District of Wisconsin, Case No. 05C 0575 C, Filed Sept. 29, 2005.

Brief in Support of Deft. Motion in Limine to Exclude Testimony From William S. Reznikoff on Validity. (filed under SEAL at the district court) U.S. District Court for the Western District of Wisconsin, Case No. 05C 0575 C. Filed Sep. 29, 2005.

Motion in Limine by Deft. to Exclude Hearsay Testimony of Dr. Geert Maertens. (filed under SEAL at the district court) U.S. District Court for the Western District of Wisconsin, Case No. 05C 0575 C, Filed Sep. 29, 2005.

Brief in Support of Deft. Motion in Limine to Exclude Hearsay Testimony of Dr. Geert Martens. (filed under SEAL at the district court) U.S. District Court for the Western District of Wisconsin, Case No. 05C 0575 C, Filed Sep. 29, 2005.

Order Granting Pltf Mots/Amend. to Strike New Claim Const, to Suppl Prop Findings; Deft S/J Mot Denied; Claims Construed U.S. District Court for the Western District of Wisconsin, Case No. 05C 0575 C, Filed Sep. 29, 2005.

Expert Report of (Supplemental) of Howard J. Worman. U.S. District Court for the Western District of Wisconsin, Case No. 05C 0575 C, Filed Sep. 29, 2005.

Brief in Reply in Support of Deft. Motion for Reconsideration of Exceptional Case Finding Under 35 U.S.C. 285. U.S. District Court for the Western District of Wisconsin, Case No. 05C 0575 C, Filed Sep. 29 2005.

Brief in Opposition by Pltf, to Deft. Mot. in Limine to Exclude Testimony From William Reznikoff on Validity. (filed under SEAL at the district court) U.S. District Court for the Western District of Wisconsin, Case No. 05C 0575 C, Filed Sep. 29, 2005.

Brief in Opposition by Pltf. to Deft. Mot. in Limine to Preclude Reference to Summary Judgment Decision. U.S. District Court for the Western District of Wisconsin, Case No. 05C 0575 C Filed Sep. 29 2005.

Brief in Opposition by Pltf. to Deft Motion in Limine to Exclude Hearsay Testimony of Geert Maertens, U.S. District Court for the Western District of Wisconsin, Case No. 05C 0575 C, Filed Sep. 29, 2005.

Brief in Opposition by Deft. to Pltf. Motion in Limine to Exclude Section 112 Defenses. U.S. District Court for the Western District of Wisconsin, Case No. 05C 0575 C, Filed Sep. 29, 2005.

Brief in Opposition by Deft. to Pltf. Motion in Limine to Exclude Testimony of Bruce Patterson Re: Obviousness. U.S. District Court for the Western District of Wisconsin, Case No. 05C 0575 C, Filed Sep. 29, 2005.

Brief in Opposition by Deft. to Pltf. Motion in Limine Re: Anticipation. U.S. District Court for the Western District of Wisconsin, Case No. 05C 0575 C, Filed Sep. 29. 2005.

Brief in Opposition by Deft. to Pltf. Motion in Limine to Exclude Testimony of Tai-An Cha and Thomas White. U.S. District Court for the Western District of Wisconsin, Case No. 05C 0575 C. Filed Sep. 29.2005.

Brief in Opposition by Deft. to Pltf. Motion in Limine to Exclude Evidence of Prosecution of European Patent. U.S. District Court for the Western District of Wisconsin, Case No. 050 0575 C. Filed Sep. 29, 2005.

Brief in Opposition by Pltf. to Deft. Motion in Limine to Exclude Reference to License Agreements Involving '704 Patent. U.S. District Court for the Western District of Wisconsin, Case No. 05C 0575 C, Filed Sep. 29, 2005.

Brief in Opposition by Pltf. to Deft. Motion in Limine to Exclude Evidence Relating to '944 Patent. U.S. District Court for the Western District of Wisconsin Case No. 05C 0575 C, Filed Sep. 29, 2005.

Brief in Opposition by Pltf. to Deft. Motion in Limine to Exclude Evidence That Invention Claimed Is "Pioneering." U.S. District Court for the Western District of Wisconsin, Case No. 05C 0575 C, Filed Sep. 29, 2005.

Brief in Opposition by Pltf. to Deft. Motion in Limine to Exclude Evidence of Patent Law, Practice or Procedure. U.S. District Court for the Western District of Wisconsin, Case No. 05C 0575 C, Filed Sep. 29, 2005.

Brief in Opposition by Pltf. to Deft. Motion in Limine to Exclude Evidence Re: "Multiple Probes." U.S. District Court for the Western District of Wisconsin Case No. 050 0575 C, Filed Sep. 29, 2005.

Orders—FPTC. U.S. District Court for the Western District of Wisconsin. Case No. 05C 0575 Filed Sep. 29, 2005 U.S. District Court for the Western District of Wisconsin, Case No. 05C 0575 C, Filed Sep. 29, 2005.

Transcript of Final Pretrial Conference, Held Aug. 17, 2006. (E: Notice Sent to All Counsel of Record). U.S. District Court for the Western District of Wisconsin, Case No. 050 0575 C, Filed Sep. 29, 2005.

Order Denying Deft, Mot. in Limine to Exclude Evidence That Claimed Method of Genotyping Requires Using Multiple Probes. U.S. District Court for the Western District of Wisconsin, Case No. 05C 0575 C, Filed Sep. 29, 2005.

Notification That Pltf. Does Not Oppose Deft. Motion in Limine to Preclude Evidence of HCV Quantitative Assay. U.S. District Court for the Western District of Wisconsin, Case No. 05C 0575 C. Filed Sep. 29 2005.

Deft. Notice To Court of Pltf. Withdrawal of Claims. U.S. District Court for the Western District of Wisconsin, Case No. 05C 0575 C, Filed Sep. 29, 2005.

Proposed Special Verdict by Pltf.—Liability (Redlined Version) U.S. District Court for the Western District of Wisconsin, Case No. 05C 0575 C, Filed Sep. 29, 2005.

Motion by Pltf. to Clarify Court Construction of Term Specifically Hybridizes. U.S. District Court for the Western District of Wisconsin, Case No. 05C 0575 C, Filed Sep. 29, 2005.

Motion in Limine by Deft. to Exclude Reference to Aug. 11, 2006 Order U.S. District Court for the Western District of Wisconsin, Case No. 05C 0575 C, Filed Sep. 29, 2005.

Proposed Special Verdict by Deft. Re: Liability —Revised. U.S. District Court for the Western District of Wisconsin Case No. 050 0575 C, Filed Sep. 29, 2005.

Proposed Jury Instructions by Deft. Re: Liability—Revised. U.S. District Court for the Western District of Wisconsin, Case No. 05C 0575 C, Filed Sep. 29, 2005.

Introductory Jury Instructions. U.S. District Court for the Western District of Wisconsin, Case No. 05C 0575 C, Filed Sep. 29, 2005.

Pltf. Additional Proposed Jury Instruction Re: Court Ruling on Infringement. U.S. District Court for the Western District of Wisconsin, Case No. 05C 0575 C, Filed Sep. 29, 2005.

Deft. Objection to Pltf. Proposed Jury Instruction Regarding Court Ruling of Infringement. U.S. District Court for the Western District of Wisconsin, Case No. 05C 0575 C, Filed Sep. 29, 2005.

Deft. Revised Proposed Post-Trial Jury Instructions on Invalidity. U.S. District Court for the Western District of Wisconsin, Case No. 05C 0575 C, Filed Sep. 29, 2005.

Motion by Pltf. for a Curative Instruction. U.S. District Court for the Western District of Wisconsin, Case No. 05C 0575 C, Filed Sep. 29, 2005.

Transcript of First Day of Trial (Excluding Voir Dire), Held Aug. 28, 2006. U.S. District Court for the Western District of Wisconsin, Case No. 05C 0575 C, Filed Sep. 29, 2005.

Transcript of Second Day of Trial Morning Session—vol. 1, Held Aug. 29, 2006. U.S. District Court for the Western District of Wisconsin, Case No. 05C 0575 C, Filed Sep. 29, 2005.

Transcript of Second Day of Trial Morning Session—vol. 2, Held Aug. 29, 2006. U.S. District Court for the Western District of Wisconsin, Case No. 05C 0575 C, Filed Sep. 29, 2005.

Transcript of Second Day of Trial Afternoon Session—vol. 3, Held Aug. 29, 2006. U.S. District Court for the Western District of Wisconsin, Case No. 05C 0575 C, Filed Sep. 29, 2005.

Brief in Opposition by Deft. to Pltf. Motion for a Curative Instruction. U.S. District Court for the Western District of Wisconsin, Case No. 05C 0575 C, Filed Sep. 29, 2005.

Transcript of Third Day Jury Trial U.S. District Court for the Western District of Wisconsin, Case No. 05C 0575 C, Filed Sep. 29, 2005.

Transcript of Fourth Day of Jury Trial U.S. District Court for the Western District of Wisconsin, Case No. 05C 0575 C, Filed Sep. 29, 2005.

Post-Trial Jury Instructions—Invalidity. U.S. District Court for the Western District of Wisconsin, Case No. 05C 0575 C, Filed Sep. 29, 2005.

Special Verdict—Liability. U.S. District Court for the Western District of Wisconsin. Case No. 05C 0575 C, Filed Sep. 29, 2005.

Transcript of Fifth Day of Jury Trial; Held Sep. 1, 2006. U.S. District Court for the Western District of Wisconsin, Case No. 05C 0575 C, Filed Sep. 29, 2005.

Transcript of Sixth Day Jury Trial, vol. 1, 2, Held Sep. 5, 2006, U.S. District Court for the Western District of Wisconsin. Case No. 05C 0575 C, Filed Sep. 29, 2005.

Transcript of Seventh Day of Jury Trial, Morning Session—vol. 1, 2, Held Sep. 6, 2006. U.S. District Court for the Western District of Wisconsin, Case No. 05C 0575 C. Filed Sep. 29, 2005.

Transcript of Eighth Day of Jury Trial—vol. I, II, III. Held Sep. 7, 2006. U.S. District Court for the Western District of Wisconsin, Case No. 05C 0575 C, Filed Sep. 29, 2005.

Transcript of Ninth Day of Jury Tria—vol. I, II, III. Held Sep. 8, 2006. U.S. District Court for the Western District of Wisconsin, Case No. 05C 0575 C, Filed Sep. 29, 2005.

Special Verdict Damages. U.S. District Court for the Western District of Wisconsin, Case No. 05C 0575 C, Filed Sep. 29, 2005.

Judgment in Favor of Pltf. Finding Willful Infringement by Deft. and Awarding Damages of $7,000,000. (BBC/TMO) CC Mld. U.S. District Court for the Western District of Wisconsin, Case No. 05C 0575 C, Filed Sep. 29, 2005.

Motion by Deft. for New Trial on Issues of Infringement and Invalidity. U.S. District Court for the Western District of Wisconsin, Case No. 05C 0575 C, Filed Sep. 29, 2005.

Brief in Support of Deft. Motion for New Trial on Issues of Infringement and Invalidity. U.S. District Court for the Western District of Wisconsin. Case No. 05C 0575 C, Filed Sep. 29, 2005.

Innogenetics' Brief in Opposition to Abbott's Motion for New Trial on the Issues of Infringement and Invalidity (Trial Phase I) U.S. District Court for the Western District of Wisconsin, Case No. 05C 0575 C, Filed Sep. 29, 2005.

Reply Brief in Support of Abbott'S Motion for New Trial on the Issues of Infringement and Invalidity (Trial Phase I). U.S. District Court for the Western District of Wisconsin, Case No. 05C 0575 C, Filed Sep. 29, 2005.

Opinion and Order Re New Trial on the Issues of Infringement, Invalidity, Damages, Willfulness and Permanent Injunction. U.S. District Court for the Western District of Wisconsin, Case No. 05C 0575 C, Filed Sep. 29, 2005.

Statement of Assignee, Innogenetics, executed Feb. 13, 2007.

* cited by examiner

| Isolate | Type | 240↓ -230↓ -220↓ -180↓ -170↓ -160↓ -150↓ -140↓ GAGTGTCGTGCAGCCTCCAGGACCC*AGTACACCGGAATTGCCAGGACGACCGGGTCCTTTC..TTGGATC.AA | Accession number ref. | |
|---|---|---|---|---|
| HCV-1 | 1a | GAGTGTCGTGCAGCCTCCAGGACCC*AGTACACCGGAATTGCCAGGACGACCGGGTCCTTTC..TTGGATC.AA | 1 | |
| HCV-J | 1b | -----T--------------------*------------------------------------.--------- | 2 | SEQ ID NO 61 |
| BE82 | 1b | --------------------------*------------------------------------.--------- | | SEQ ID NO 62 |
| BE90 | 1b | --------------------------*-----------------T------------------.-T------- | | |
|  |  |  |  |  |
| HC-J6 | 2a | ----------A---------------*--------------C--------G-A--T-------.-A------- | 3 | SEQ ID NO 63 |
| HC-J8 | 2b | ----------A---------------*--------------C--------A-G-A-A---T--.-A------- | 4 | |
| BE91 | 2b | ----------A---------------*--------------C--------A-G-A-A---T--.-A------- | | |
|  |  | 32 |  |  |
| BE92 | 2c | ----------A---------------*--------------C-----------A---T-----.-A------- | | SEQ ID NO 64 |
|  |  | 33 |  |  |
| BR56 | 3a | --------------------------*--------------C-----------C--TG--GT-.-G------- | 5 | SEQ ID NO 65 |
| BE93 | 3a | --------------------------*--------------C-----------C--TG--GT-.-G------- | | SEQ ID NO 66 |
| BE94 | 3a | --------------------------*--------------C-----------C--TG--GT-.-G------- | | |
|  |  |  |  |  |
| HCV-TR | 3b | --------------------------*--------------C-----------C---G--T--.-A------- | 6 | |
|  |  |  |  |  |
| BE99 | 3c | --------------------------*--------------C-----------C--G--TT--.-A--T---- | | SEQ ID NO 80 |
|  |  | 54 |  |  |

FIG. 4A-1

| Isolate | Type | -240 | -230 | -220 -180 | -170 | -160 | -150 | -140 | Accession number ref. | |
|---|---|---|---|---|---|---|---|---|---|---|
| GB48 | 4a | -----T- | --A-- | ......* | ----- | -C---G---T-- | ----- | ---A.- | | SEQ ID NO 67 |
| GB116 | 4a | -----T- | --A-- | ......* | ----- | -C---G---T-- | ----- | ---T.- | | SEQ ID NO 68 |
| GB569 | 4a | -----T- | --A-- | ......* | ----- | -C---G---T-- | ----- | ---A.- | | SEQ ID NO 69 |
| GB358 | 4a | -----T- | --A-- | ......* | ----- | -C---G---T-- | 38 | ---A.- | | SEQ ID NO 70 |
|  |  |  | 37 |  |  |  |  |  |  |  |
| Z1 | 4b | -----T- | --A--C | ......* | ----- | -C---G---T-- | ----- | ----.- | |  |
| CAM600 | 4c | -----T- | --A-- | ......* | ----- | -C---GA--T-- | ----- | ----.- | | SEQ ID NO 72 |
| CAM736 | 4c | -----T- | --A-- | ......* | ----- | -C---GA--T-- | ----- | ----.- | | SEQ ID NO 73 |
| GB809 | 4c | -----T- | --A-- | ......* | ----- | -C---GA--T-- | 42 | ----.- | | SEQ ID NO 74 |
| Z4 | 4c | -----T- | --A-- | ......* | ----- | -C-------- | ----- | ---A.- | |  |
| DK13 | 4d | -----T- | ----- | ......* | ----- | -C---G---T-- | ----- | ----.- | | SEQ ID NO 71 |
|  |  | 39 |  |  |  |  |  |  |  |  |
| GB549 | 4e | -----T- | ----- | ......* | --T-- | -C---G---T-- | 40 | -A-A-- | | SEQ ID NO 81 |
| GB438 | 4f | ----- | --A-- | ......* | --T-- | -C---G---T-- | ----- | --ATC-- | |  |
| GB724 | 4g | ----- | --A-- | ......* | --T-- | -C------- | ----- | ---T.- | | SEQ ID NO 76 |
|  |  |  | 51 |  |  | 52 |  |  |  |  |
| BE97 | 4g | -----T- | --A-- | ......* | ----- | -C------- | 53 | ---T.- | | SEQ ID NO 77 |
| GB487 | 4h | -----T- | --A-- | ......* | ----- | -C---T-- | 49 | ---T.- | | SEQ ID NO 75 |

FIG. 4A-2

| Iso-late | Type | -240 | -230 | -220 -180 | -170 | -160 | -150 | -140 | Accession number ref. | |
|---|---|---|---|---|---|---|---|---|---|---|
| SA1 | 5a | ----- | --AA- | -----*----- | ----- | --G--T- | ----- | --A.- | 7 | SEQ ID NO 78 |
| BE95 | 5a | ----- | --AA- | -----*----- | ----- | --G--T- | ----- | --T.- | | |
| BE96 | 5a | ----- | --AA- | -----*----- | ----- | --G--- | 45 47 | --A.- | | |
|   |   |   | 44 |   |   |   |   |   |   |   |
| HK1 | 6a | ----- | --A-- | -----C----- | ----- | -----T- | ----- | --CA-- | 8 | SEQ ID NO 79 |
| HK2 | 6? | ----- | --A-- | -----C----- | ----- | -----T- | ----- | --CA-- | | |
|   |   |   |   |   |   |   |   | 48 |   |   |

| Isolate | Type | -130　　-120　　-110　　-100　　-90　　-80　　-70 | Accession number reference |
|---|---|---|---|
| HCV-1 | 1a | CCCGCTCAATGCCTGGAGATTTGGGCGTGCCCCCGCAAGACTGCTAGCCGAGTAGTGTTGGGTCGCGA<br>　　　　　　　　　　　　　　　　　　　　　31 | 1 |
| HCV-J | 1b | ------------------------------------G--------------------------------- | 2 |
| BE82 | 1b | -----------------------------------G-------G-C----------------------- | 2 |
| BE90 | 1b | ------G--------------------------G-------G-C----------------------- <br>　　　　　　　　　　　　　　　　　　　　　30 | 2 |
| HC-J6 | 2a | ---A------T------TC----------------------C----------C-----T--------- | 3 |
| HC-J8 | 2b | ---A---T-C------TC----------------AC--------C-T----T----------- | 4 |
| BE91 | 2b | ---A---T-C------TC------------------------T-C----T----------- | 4 |
| BE92 | 2c | ---A------T------TC-----------------------C----------T----------- <br>　　　　　　　　　　　　　　　　34 | 4 |
| BR56 | 3a | ---A--CA--A----------------G-----TCA----------------------- | 5 |
| BE93 | 3a | ---A--CA--C----------------G-----TCA----------------------- | 5 |
| BE94 | 3a | ---A--CA--C----------------G-----TCA----------------------- <br>　　　　　　　35　　　　　　　　　　　36 | 5 |
| HCV-TR | 3b | ------------C-----A--------------G-----TCA----------------------- | 6 |

| Isolate | Type | -130 | -120 | -110 | -100 | -90 | -80 | -70 | Accession number reference |
|---|---|---|---|---|---|---|---|---|---|
| GB48 | 4a | ------ | --C-- | ---A-- | ------ | ------ | ------ | ------ | |
| GB116 | 4a | ------ | --C-- | ---A-- | ------ | ------ | ------ | ------ | |
| GB569 | 4a | ------ | --C-- | ---A-- | ------ | ------ | ------ | ------ | |
| GB358 | 4a | ------ | --C-- | ---A-- | ------ | ------ | ------ | ------ | |
| GB549 | 4e | ------ | --C--CA-- 41 | ------ | ------ | ------ | ------ | ------ | |
| CAM600 | 4c | ------ | --TC--A-- | ------ | ------ | ------ | ------ | ------ | |
| CAM736 | 4c | ------ | --TC--A-- | ------ | ------ | ------ | ------ | ------ | |
| GB809 | 4c | ------ | --TC--A-- 43 | ------ | ----C- | ------ | ------ | ------ | |
| GB487 | 4h | ------ | ------A-- 50 | ------ | ------ | ------ | ------ | ------ | |
| GB724 | 4g | ------ | ------A-- | ------ | ------ | ------ | ------ | ------ | |
| BE97 | 4g | ------ | ------A-- | ------ | ------ | ------ | ------ | ------ | |
| SA1 | 5a | ------ | ---C--- | ------ | ---G-- | ------ | ------ | ------ | |
| BE96 | 5a | ------ | ---C--- | ------ | ---G-- | ------ | ------ | ------ | |
| BE95 | 5a | ------ | ---C--- 46 | ------ | ---G-- | ------ | ------ | ------ | |
| HK1 | 6a | ------ | ------ | ------ | ------ | ------ | ------ | ------ | 7 |
| BE98 | 3c | ------ | ---C--A-- | ------ | ---G-- | ------ | ------ | ------ | 8 |
| GB438 | 4f | ------ | ---C--A-- | ------ | ---G-- | ------ | ------ | ------ | |

|          | 101            | SEQ ID NO |
|----------|----------------|-----------|
| HCV-1    | SAGVQEDAASLRA  |           |
| HC-J1    | -------------  |           |
| HCV-H    | -------------  |           |
| HCV-J    | ---T-----A---  |           |
| HCV-JK1  | ---T--------V  |           |
| HCV-CHINA| ---T--------V  |           |
| HCV-T    | ---T--------V  |           |
| HC-J4.91 | ---T-----A---  |           |
| HCV-TA   | ---T--------V  |           |
| HCV-JT   | ---T--------V  |           |
| HCV-BK   | ---T--------V  |           |
| BE90     | ---T--------V  | 82        |
| HC-J6    | -Q-TE--ERN---  |           |
| HC-J8    | -Q-NE--ERN---  |           |
| BE91     | -Q-NE--ERN---  | 83        |
| BE92     | -Q-TE--ERN---  | 84        |
| T1       | -D--D--R-A---  |           |
| T7       | -D--D--RTA---  |           |
| BE93     | -D--D--R-A---  | 85        |
| T9       | -C--E--R-A---  |           |
| T10      | -C--E--R-A---  |           |
| GB48     | -D--E--KRP-G-  | 86        |
| GB116    | -D--E--KRA-G-  | 87        |
| GB215    | -D--E--KRA-GV  | 88        |
| GB358    | -D--E--KRA-G-  | 89        |
| GB549    | -G--E---RA---  | 90        |
| GB809    | -G--E--KRA-G-  | 91        |
| BE95     | -Q-TH--E-----  | 92        |
| CHR18    | -Q-TH--K-----  |           |

FIG. 5B

PROCESS FOR TYPING OF HCV ISOLATES

This application is a divisional of Application No. 10/412,290, filed Apr. 14, 2003 (which issued as U.S. Pat. No. 7,258,977 on Aug. 21, 2007), which is a continuation of Application No. 09/899,044, filed Jul. 6, 2001 (which issued as U.S. Pat. No. 6,548,244), which is a divisional of Application No. 09/378,900, filed Aug. 23, 1999 (which issued as U.S. Pat. No. 6,495,670), which is a divisional of Application No. 09/044,665, filed Mar. 19, 1998 (which issued as U.S. Pat. No. 6,051,696), which is a divisional of Application No. 08/256,568, filed Jul. 18, 1994, which issued as U.S. Pat. No. 5,846,704, which is a 371 U.S. National Phase of PCT/EP93/03325, filed Nov. 26, 1993, which claims benefit of EP 92 403 222.0, filed Nov. 27, 1992 and EP 93 402 129.6, filed Aug. 31, 1993, the entire content of each of which is hereby incorporated by reference in this application The invention relates to the use of probes targeting sequences from the 5' untranslated region of HCV for genotyping of HCV isolates.

The invention also relates to a process for genotyping of HCV isolates.

The invention also relates to a kit for genotyping of HCV isolates.

Hepatitis C viruses (HCV) are a family of positive-stranded, enveloped RNA viruses causing the majority of non-A, non-B (NANB) hepatitis: Their genomic organization indicates a close relationship to the Pestiviridae and Flaviviridae. The sequences of cDNA clones covering the complete genome of several prototype isolates have already been completely determined (Kato et al., 1990; Choo et al., 1991; Okamoto et al., 1991; Takamizawa et al., 1991; Okamoto et al., 1992b). These genomes are about 9500 base pairs long. The isolates reported by Kato, Takamizawa, and Choo contain an open reading frame (ORF) of 3010 or 3011 amino acids, and those reported by Okamoto encode 3033 amino acids. Comparison of these isolates shows a considerable variability in the envelope (E) and non-structural (NS) regions, while the 5' untranslated region (UR) and, to a lesser extent, the core region are highly conserved.

Using cloned sequences of the NS3 region, Kubo et al. (1989) compared a Japanese and an American isolate and found nearly 80% nucleotide and 92% amino acid homology. The existence of sequence variability was further documented when sequences of the 5' UR, core, and E1 regions became available (HC-J1 and HC-J4; Okamoto et al., 1990). After the isolation of several NS5 fragments in Japanese laboratories, two groups, K1 and K2, were described (Enomoto et al., 1990). A comparison of the "American-like" isolate PT-1 with K1, which was more prevalent in Japan, showed that they represent closely related but different subtypes with an intergroup nucleotide identity of about 80%. The K2 sequence was more distantly related to both K1 and PT-1, because homologies of only 67% at the nucleic acid level, and 72% at the amino acid level were observed. Moreover, K2 could be divided into two groups, K2a and K2b, also showing intergroup nucleotide homologies of about 80%. Nucleotide sequence analysis in the 5' UR showed 99% identity between K1 and PT-1, and at most 94% identity between K1 and K2, enabling the use of the 5' UR for restriction fragment length polymorphism (RFLP) and classification of HCV into groups K1 and K2 (Nakao et al., 1991). Further evidence for a second group was given by the complete sequence of HC-J6 and HC-J8, two sequences related to the K2 group (Okamoto et al., 1991; Okamoto et al., 1992b). A phylogenetic tree of HCV containing four branches (i.e., Type I: HCV-1 and HCV-H; Type HCV-J, -BK, HC-J4; Type III: HC-J6; Type IV: HC-J8) was proposed by Okamoto et al. (1992b). However, nucleic acid sequence homologies of 79% can be observed between Type I and Type II, and also between Type III and IV. A lesser degree of relatedness between the first group (Type I and II) and the second group (Types III and IV) of only 67-68% exists. Moreover, a new type of HCV, HCV-T, was detected in Thailand after studying NS5 regions (Mori et al., 1992). HCV-T had a sequence homology of about 65% with all other known NS5 sequences, and two groups could be detected, HCV-Ta and HCV-Tb, which again exhibited nucleic acid sequence homologies of about 80%. Elucidation of the phylogenetic relationship of a similar new group found in British isolates with Type I to IV was possible by analyzing the conserved parts of the 5' UR, core, NS3, and NS5 regions (Chan et al., 1992a). A new phylogenetic tree was proposed, whereby 'type 1' corresponds with Type I and II, 'type 2' with Type III and IV, and 'type 3' with their own isolates E-b1 to E-b8 and HCV-T. Some sequences of the 5' UR of isolates from 'type 3' were also reported by others (Bukh et al., 1992; Cha et al., 1992; Lee et al., 1992).

Several patent applications have addressed the problem of detecting the presence of HCV by means of probes derived from the genome of type 1 HCV isolates (WO 92/02642, EP 419 182, EP 398 748, EP 469 438 and EP 461 863). Furthermore, the 5' UR of HCV isolates has been proven to be a good candidate for designing probes and primers for general HCV detection (Cha et al., 1991; Inchaupse et al., 1991). However, none of these patent applications presents a method for identifying the type and/or subtype of HCV present in the sample to be analyzed.

The demonstration that different HCV genotype infections resulted in different serological reactivities (Chan et al., 1991) and responses to interferon IFN-γ treatment (Pozatto et al., 1991; Kanai et al., 1992; Yoshioka et al., 1992) stresses the importance of HCV genotyping. Until now, this could only be achieved by large sequencing efforts in the coding region or in the 5' UR, or by polymerase chain reactions (PCR) on HCV cDNA with type-specific sets of core primers (Okamoto et al. 1992a), or by (RFLP) analysis in the 5' UR or in the NS5 region (Nakao et al., 1991; Chan et al., 1992b). However, none of these above-mentioned patent applications or publications offers a reliable method for identifying the type or subtype of HCV present in the sample to be analyzed, especially since typing is laborious and subtyping seems to be even more laborious or impossible by means of these methods. In this respect, it can be noted that Lee et al. (1992) attempt to distinguish between the HCV isolates HCV 324 and HCV 324X by means of PCR fragments from the 5' UR of the genomes of these isolates. The results demonstrate that these 5' UR probes do not show a specific reactivity with the genome of the respective isolate from which they were derived.

Consequently, the aim of the present invention is to provide a method for the rapid and indisputable determination of the presence of one or several genotypes of HCV present in a biological sample and indisputably classifying the determined isolate(s).

Another aim of the invention is to provide a process for identifying yet unknown HCV types or subtypes.

Another aim of the invention is to provide a process enabling the classification of infected biological fluids into different serological groups unambiguiously linked to types and subtypes at the genomic level.

Another aim of the invention is to provide a kit for rapid detection of the presence or absence of different types or subtypes of HCV.

The invention relates to the use of at least one probe, with said probe being (i) capable of hybridizing to a genotype specific target region, present in an analyte strand, in the domain extending from the nucleotides at positions −291 to −66 of the 5' untranslated region (UR) of one of the HCV isolates, or with said probe being (ii) complementary to any of the above-defined probes, for genotyping HCV isolates present in a biological sample.

The invention relates to the use of at least one probe preferably containing from about 5 to about 50 nucleotides, more preferably from about 10 to about 40 nucleotides, and most preferably containing from about 15 to about 30 nucleotides, with said probe being (i) capable of liable to hybridizing to a genotype specific target region present in an analyte strand in the domain extending from the nucleotides at positions −291 to −66 of the 5' UR of one of the HCV isolates represented by their cDNA sequences, for example represented by their cDNA sequences in FIG. 2, with said negative numbering of the nucleotide positions starting at the nucleotide preceding the first ATG codon of the open reading frame encoding the HCV polyprotein, or with said probe being (ii) complementary to the above-defined probes, for (in vitro) genotyping HCV isolates present in a biological sample, with said sample being possibly previously identified as being HCV positive.

The above mentioned process may be used for classifying said isolate according to the percentage of homology with other HCV isolates, according to the fact that isolates belonging to the same type:

exhibit homology of more than 74% at the nucleic acid level in the complete genome;

or exhibit homology of more than 74% at the nucleic acid level in the NS5 region between nucleotide positions 7935 and 8274;

or of which the complete polyprotein shows more than 78% homology at the amino acid level;

or of which the NS5 region between amino acids at positions 2646 and 2758 shows more than 80% homology at the amino acid level;

and according to the fact that HCV isolates belonging to the same subtype exhibit homology of more than 90% at the nucleic acid level in the complete genome and of more than 90% at the amino acid level in the complete polyprotein.

More preferably the above mentioned process relates to the classification of HCV isolates according to the fact that, (1) based on phylogenetic analysis of nucleic acid sequences in the NS5b region between nucleotides 7935 and 8274 (Choo et al., 1991) or 8261 and 8600 (Kato et al., 1990) or 8342 and 8681 (Okamoto et al, 1991), isolates belonging to the same HCV type show nucleotide distances of less than 0.34, usually less than 0.33, and more usually of less than 0.32, and isolates belonging to the same subtype show nucleotide distances of less than 0.135, usually of less than 0.13, and more usually of less than 0.125, and consequently isolates belonging to the same type but different subtypes show nucleotide distances ranging from 0.135 to 0.34, usually ranging from 0.14 to 0.33, and more usually ranging from 0.15 to 0.32, and isolates belonging to different HCV types show nucleotide distances greater than 0.34, usually greater than 0.35, and more usually of greater than 0.36, (2) based on phylogenetic analysis of nucleic acid sequences in the core/E1 region between nucleotides 378 and 957, isolates belonging to the same HCV type show nucleotide distances of less than 0.38, usually of less than 0.37, and more usually of less than 0.36, and isolates belonging to the same subtype show nucleotide distances of less than 0.17, usually of less than 0.16, and more usually of less than 0.15, and consequently isolates belonging to the same type but different subtypes show nucleotide distances ranging from 0.15 to 0.38, usually ranging from 0.16 to 0.37, and more usually ranging from 0.17 to 0.36, and isolates belonging to different HCV types show nucleotide distances greater than 0.36, usually more than 0.365, and more usually of greater than 0.37, (3) based on phylogenetic analysis of nucleic acid sequences in the NS3/NS4 region between nucleotides 4664 and 5292 (Choo et al., 1991) or between nucleotides 4993 and 5621 (Kato et al., 1990) or between nucleotides 5017 and 5645 (Okamoto et al., 1991), isolates belonging to the same HCV type show nucleotide distances of less than 0.35, usually of less than 0.34, and more usually of less than 0.33, and isolates belonging to the same subtype show nucleotide distances of less than 0.19, usually of less than 0.18, and more usually of less than 0.17, and consequently isolates belonging to the same type but different subtypes show nucleotide distances ranging from 0.17 to 0.35, usually ranging from 0.18 to 0.34, and more usually ranging from 0.19 to 0.33, and isolates belonging to different HCV types show nucleotide distances greater than 0.33, usually greater than 0.34, and more usually of greater than 0.35.

The term "genotyping" refers to either typing and/or subtyping. A method for 'genotyping' HCV isolates is considered to, at least partly, classify HCV isolates into genotypes. A HCV 'genotype' is a group of HCV isolates with related sequences. Said related sequences are defined as showing nucleotide distances as indicated above and as illustrated in example 9. Both larger groups (HCV types) and smaller groups (HCV subtypes) have been shown to be related. A HCV type always includes one or more HCV subtypes. Consequently, a method for genotyping can aim at typing (classification into HCV types) of HCV isolates without the need for subtyping (classification into HCV subtypes), or, in a preferred embodiment, subtyping can be aimed at. It should be understood that classification into subtypes inherently yields data for classification into types.

The expression "genotype specific target region" refers at least one nucleotide variation observed between different HCV genotypes in the 5' untranslated region (UR) as can be readily deduced from FIGS. 2 and 4.

The term "HCV polyprotein" refers to the HCV polyprotein of the HCV-J isolate (Kato et al., 1990), which belongs to subtype 1b.

The expression "probe" corresponds to any polynucleotide which forms a hybrid with a target sequence present in a certain HCV isolate on the basis of complementarity. Such a probe may be composed of DNA, RNA, or synthetic nucleotide analogs. The probes of the invention can be incubated with an analyte strand immobilized to a solid substrate. In a preferred embodiment of the invention, the probes themselves can be immobilized to a solid substrate. These probes may further include capture probes, characterized as being coupled to a binding molecule which in turn is directly or indirectly bound to a solid substrate, or may also include label probes, characterized in that they carry a detectable label.

The invention relates to a process for genotyping HCV isolates present in a biological sample; comprising the steps of:

contacting said sample in which the ribonucleotides or deoxyribonucleotides have been made accessible, if need be, under suitable denaturation, with at least one probe, with said probe being (i) capable of hybridizing to a region in the domain extending from nucleotides at positions −291 to −66 of the 5' untranslated region of one of the HCV isolates, or with said probe being (ii) complementary to any of the above-defined probes, and, detecting the complexes possibly formed between said probe and the nucleotide sequence of the HCV isolate to be identified.

The invention relates also to a process for genotyping an HCV isolate present in a biological sample, comprising the steps of:

contacting said sample in which the ribonucleotides and deoxyribonucleotides have been made accessible, if need be, under suitable denaturation, with at least one probe from preferably from about 5 to 50, more preferably from about 10 to about 40 nucleotides most preferably from about 15 to about 30 nucleotides, with said probe being (i) capable of hybridizing to a region in the domain extending from nucleotides at positions −291 to −66 of the 5' UR of one of the HCV isolates represented by their cDNA sequences, for example represented by their cDNA sequences in FIG. 2, with said negative numbering of position starting at the nucleotide preceding the first ATG codon of the open reading frame encoding the HCV polyprotein, or with said probe being complementary to the above-defined probes, detecting the complexes possibly formed between said probe and the nucleotide sequence of the HCV isolate to be identified, and, inferring the type(s) of HCV isolates present from the hybridization pattern.

The above mentioned method can be considered as a method for classifying said isolate according to the percentage of homology with other HCV isolates, according to the fact that isolates belonging to the same type:

exhibit homology of more than 74% at the nucleic acid level in the complete genome, or exhibit homology of more than 74% at the nucleic acid level in the NS5 region between nucleotide positions 7935 and 8274, or of which the complete polyprotein shows more than 78% homology at the amino acid level, or of which the NS5 region between amino acids at positions 2646 and 2758 shows more than 80% homology at the amino acid level, and according to the fact that HCV isolates belonging to the same subtype exhibit homology of more than 90% at the nucleic acid level in the complete genome and of more than 90% at the amino acid level in the complete polyprotein.

More preferably, said method relates to the classification of HCV isolates according to the fact that, (1) based on phylogenetic analysis of nucleic acid sequences in the NS5b region between nucleotides 7935 and 8274 (Choo et al., 1991) or 8261 and 8600 (Kato et al., 1990) or 8342 and 8681 (Okamoto et al, 1991), isolates belonging to the same HCV type show nucleotide distances of less than 0.34, usually less than 0.33, and more usually of less than 0.32, and isolates belonging to the same subtype show nucleotide distances of less than 0.135, usually of less than 0.13, and more usually of less than 0.125, and consequently isolates belonging to the same type but different subtypes show nucleotide distances ranging from 0.135 to 0.34, usually ranging from 0.14 to 0.33, and more usually ranging from 0.15 to 0.32, and isolates belonging to different HCV types show nucleotide distances greater than 0.34, usually greater than 0.35, and more usually of greater than 0.36, (2) based on phylogenetic analysis of nucleic acid sequences in the core/E1 region between nucleotides 378 and 957, isolates belonging to the same HCV type show nucleotide distances of less than 0.38, usually of less than 0.37, and more usually of less than 0.36, and isolates belonging to the same subtype show nucleotide distances of less than 0.17, usually of less than 0.16, and more usually of less than 0.15, and consequently isolates belonging to the same type but different subtypes show nucleotide distances ranging from 0.15 to 0.38, usually ranging from 0.16 to 0.37, and more usually ranging from 0.17 to 0.36, and isolates belonging to different HCV types show nucleotide distances greater than 0.36, usually more than 0.365, and more usually of greater than 0.37, (3) based on phylogenetic analysis of nucleic acid sequences in the NS3/NS4 region between nucleotides 4664 and 5292 (Choo et al., 1991) or between nucleotides 4993 and 5621 (Kato et al., 1990) or between nucleotides 5017 and 5645 (Okamoto et al., 1991), isolates belonging to the same HCV type show nucleotide distances of less than 0.35, usually of less than 0.34, and more usually of less than 0.33, and isolates belonging to the same subtype show nucleotide distances of less than 0.19, usually of less than 0.18, and more usually of less than 0.17, and consequently isolates belonging to the same type but different subtypes show nucleotide distances ranging from 0.17 to 0.35, usually ranging from 0.18 to 0.34, and more usually ranging from 0.19 to 0.33, and isolates belonging to different HCV types show nucleotide distances greater than 0.33, usually greater than 0.34, and more usually of greater than 0.35.

The term "analyte strand" corresponds to a single- or double-stranded nucleic acid molecule which is suspected to contain sequences which may be present in a biological sample, with said analyte strand being directly detected or detected after amplification. This analyte strand is preferentially positive- or negative-stranded RNA, cDNA, or amplified cDNA.

The expression "biological sample" may refer to any biological sample (tissue or fluid) containing HCV sequences and refers more particularly to blood serum or plasma samples.

The detection of hybrids formed between the type- or subtype-specific target region, if present, and the probes as mentioned above depends on the nature of the reporter molecule used (either present on the probe or on the analyte strand to be targeted) and may be determined by means of colorimetric, fluorescent, radiometric detection or any other method comprised in the state of the art.

The term "(HCV) isolates" refers to any biological fluid containing hepatitis C virus genetic material obtained from naturally infected humans or experimentally infected animals, and also refers to fluids containing hepatitis C virus genetic material which has been obtained from in vitro experiments. For instance, from in vitro cultivation experiments, both cells and growth medium can be employed as a source of HCV genomes material.

The expression "hybridize" or "target" refers to a hybridization experiment carried out according to any method known in the art, and allowing the detection of homologous targets (including one or few mismatches) or preferably completely homologous targets (no mismatches allowed).

In the present invention, a sensitive PCR protocol has been used for the highly conserved 5' UR with sets of nested, universal primers. Positions and sequences of these primers were derived from the sequences of previously reported type 1 and 2 sequences, and the type 3 sequence BR56 (FIG. 2). The obtained amplification product was hybridized to oligonucleotides directed against the variable regions of the 5' UR, immobilized as parallel lines on membrane strips (reverse-hybridization principle). This hybridization assay, called line probe assay (LiPA), is a rapid assay, by means of which previously poorly described isolates similar to Z4, Z6, and Z7 (Bukh et al., 1992) were detected. A new type 4 classification is proposed for these strains of HCV. Other isolates similar to BE95 and BE96, and to SA1 (Cha et al., 1992) can be distinguished and it is proposed to classify such isolates as type 5a. Isolates similar to HK2 (Bukh et al., 1992) can be distinguished and a new type 6a classification is proposed. A new genotype was detected in isolate BE98, and it is proposed to classify this isolate into HCV type 3, subtype 3c. Another new sequence was detected in GB438, which could be classified as 4f. This LiPA technology allows an easy and fast determination of HCV types and their subtypes present in patient serum.

According to a preferred embodiment of the invention, a set of probes comprising at least two probes is used.

According to a preferred embodiment, in the process of the invention the probe used targets a region of at least 5 nucleotides in one of the following domains:
a) the one extending from nucleotide at position −293 to nucleotide at position −278 in FIG. 2,
b) the one extending from nucleotide at position −275 to nucleotide at position −260 in FIG. 2,
c) the one extending from nucleotide at position −253 to nucleotide at position −238 in FIG. 2,
d) the one extending from nucleotide at position −244 to nucleotide at position −229 in FIG. 2,
e) the on extending from nucleotide at position −238 to nucleotide at position −223 in FIG. 2,
f) the one extending from nucleotide at position −170 to nucleotide at position −155 in FIG. 2,
g) the one extending from nucleotide at position −141 to nucleotide at position −117 in FIG. 2,
h) the one extending from nucleotide at position −83 to nucleotide at position −68 in FIG. 2,
i) the one extending from nucleotide at position −103 to nucleotide at position −88 in FIG. 2,
j) the one extending from nucleotide at position −146 to nucleotide at position −130.

Regions −170 to −155 and −141 to −117 represent variable regions in the linear sequence which may be part of the same stem in the viral RNA. Consequently mutations in one region may be complemented by another mutation in another region to allow or disallow RNA duplex formation. Variation is expected to occur at the same positions in other new types of HCV as well and, therefore, these variable regions might remain instrumental for the discrimination between all current and yet-to-be discovered types of HCV.

According to yet another embodiment the present invention relates to a probe comprising a sequence such that it targets at least one of the following sequences:

```
AAT TGC CAG GAC GAC C       (SEQ ID NO 5)
TCT CCA GGC ATT GAG C       (SEQ ID NO 6)
CCG CGA GAC TGC TAG C       (SEQ ID NO 7)
TAG CGT TGG GTT GCG A       (SEQ ID NO 8)
TTR CCG GRA AGA CTG G       (SEQ ID NO 9)
TGR CCG GGC ATA GAG T       (SEQ ID NO 10)
TTA CCG GGA AGA CTG G       (SEQ ID NO 11)
TGA CCG GAC ATA GAG T       (SEQ ID NO 12)
AAT CGC TGG GGT GAC C       (SEQ ID NO 13)
TTT CTG GGT ATT GAG C       (SEQ ID NO 14)
TCT TGG AGC AAC CCG C       (SEQ ID NO 15)
TCT TGG AAC AAC CCG C       (SEQ ID NO 16)
AAT YGC CGG GAT GAC C       (SEQ ID NO 17)
TTC TTG GAA CTA ACC C       (SEQ ID NO 18)
TTT CCG GGC ATT GAG C       (SEQ ID NO 19)
TTG GGC GYG CCC CCG C       (SEQ ID NO 20)
CCG CGA GAT CAC TAG C       (SEQ ID NO 21)
CCG GGA AGA CTG GGT C       (SEQ ID NO 22)
CCG GAA AGA CTG GGT C       (SEQ ID NO 23)
ACC CAC TCT ATG CCC G       (SEQ ID NO 24)
ACC CAC TCT ATG TCC G       (SEQ ID NO 25)
ATA GAG TGG GTT TAT C       (SEQ ID NO 26)
TCT GCG GAA CCG GTG A       (SEQ ID NO 27)
AAT TGC CAG GAY GAC C       (SEQ ID NO 28)
GCT CAG TGC CTG GAG A       (SEQ ID NO 29)
CCG CGA GAC YGC TAG C       (SEQ ID NO 30)
CCC CGC AAG ACT GCT A       (SEQ ID NO 31)
CGT ACA GCC TCC AGG C       (SEQ ID NO 32)
GGA CCC AGT CTT CCT G       (SEQ ID NO 33)
TGC CTG GTC ATT TGG G       (SEQ ID NO 34)
TKT CTG GGT ATT GAG C       (SEQ ID NO 35)
CCG CAA GAT CAC TAG C       (SEQ ID NO 36)
GAG TGT TGT ACA GCC T       (SEQ ID NO 37)
AAT CGC CGG GAT GAC C       (SEQ ID NO 38)
GAG TGT TGT GCA GCC T       (SEQ ID NO 39)
AAT CGC CGG GAC GAC C       (SEQ ID NO 40)
AAT GCC CGG CAA TTT G       (SEQ ID NO 41)
AAT CGC CGA GAT GAC C       (SEQ ID NO 42)
AAT GCT CGG AAA TTT G       (SEQ ID NO 43)
GAG TGT CGA ACA GCC T       (SEQ ID NO 44)
AAT TGC CGG GAT GAC C       (SEQ ID NO 45)
TCT CCG GGC ATT GAG C       (SEQ ID NO 46)
AAT TGC CGG GAC GAC C       (SEQ ID NO 47)
GGG TCC TTT CCA TTG G       (SEQ ID NO 48)
AAT CGC CAG GAT GAC C       (SEQ ID NO 49)
TGC CTG GAA ATT TGG G       (SEQ ID NO 50)
GAG TGT CGT ACA GCC T       (SEQ ID NO 51)
AGT YCA CCG GAA TCG C       (SEQ ID NO 52)
GGA ATC GCC AGG ACG A       (SEQ ID NO 53)
GA TCG CCG GGT TGA C        (SEQ ID NO 54)
GAG TGT TGT ACA GCC TCC     (SEQ ID NO 93)
TGC CCG GAA ATT TGG GC      (SEQ ID NO 94)
```

-continued

TGC CCG GAG ATT TGG G        (SEQ ID NO 95)

GAG TGT CGA ACA GCC TC       (SEQ ID NO 96)

wherein Y represents T or C
K represents G or T
and R represents G or A
or the corresponding sequence wherein T has been replaced by U,
or the sequences which are complementary to the above-defined sequences.

According to another advantageous embodiment of the invention, at least two of the above-mentioned probes or a mixture of two of these probes is used to discriminate between various HCV types or subtypes as defined below.

According to a preferred embodiment of the process of the invention, for each type or subtype of HCV to be determined, a set of two different probes or a mixture of two different probes is used, with each probe of the set or of the mixture respectively targeting a different region chosen among the regions as defined above, and more particularly wherein the two probes, in said set or in said mixture, consist of 10 to 40 contiguous nucleotides respectively targeting two regions respectively chosen from among the following pairs of domains:

the one extending from nucleotide at position −170 to nucleotide at position −155 in FIG. 2 and the one extending from nucleotide at position −141 to nucleotide at position −117 in FIG. 2, the one extending from nucleotide at position −170 to nucleotide at position −155 in FIG. 2 and the one extending from nucleotide at position −103 to nucleotide at position −88 in FIG. 2, the one extending from nucleotide at position −141 to nucleotide at position −117 in FIG. 2 and the one extending from nucleotide at position −103 to nucleotide at position −88 in FIG. 2, the one extending from nucleotide at position −170 to nucleotide at position −155 in FIG. 2 and the one extending from nucleotide at position −83 to nucleotide at position −68 in FIG. 2, the one extending from nucleotide at position −141 to nucleotide at position −117 in FIG. 2 and the one extending from nucleotide at position −83 to nucleotide at position −68 in FIG. 2, the one extending from nucleotide at position −170 to nucleotide at position −155 in FIG. 2 and the one extending from nucleotide at position −146 to nucleotide at position −130 in FIG. 2, the one extending from nucleotide at position −132 to nucleotide at position −117 in FIG. 2 and the one extending from nucleotide at position −146 to nucleotide at position −130 in FIG. 2, the one extending from nucleotide at position −146 to nucleotide at position −130 in FIG. 2 and the one extending from nucleotide at position −103 to nucleotide at position −88 in FIG. 2.

The invention also relates to a probe having a sequence such that it targets:
the following sequence: TTC TTG GAA CTA ACC C,
or the corresponding sequence wherein T has been replaced by U,
or the sequences which are complementary to the above-defined sequences.

The invention also relates to a set of two probes or mixtures of two probes wherein each of the two probes consists of 10 to 40 contiguous nucleotides, and wherein the two probes respectively target two regions respectively chosen from among the following pairs of domains:

the one extending from nucleotide at position −170 to nucleotide at position −155 in FIG. 2 and the one extending from nucleotide at position −141 to nucleotide at position −117 in FIG. 2, one extending from nucleotide at position −170 to nucleotide at position −155 in FIG. 2 and the one extending from nucleotide at position −103 to nucleotide at position −88 in FIG. 2, the one extending from nucleotide at position −141 to nucleotide at position −117 in FIG. 2 and the one extending from nucleotide at position −103 to nucleotide at position −88 in FIG. 2, the one extending from nucleotide at position −170 to nucleotide at position −155 in FIG. 2 and the one extending from nucleotide at position −83 to nucleotide at position −68 in FIG. 2, the one extending from nucleotide at position −141 to nucleotide at position −117 in FIG. 2 and the one extending from nucleotide at position −83 to nucleotide at position −68 in FIG. 2, the one extending from nucleotide at position −170 to nucleotide at position −155 in FIG. 2 and the one extending from nucleotide at position −146 to nucleotide at position −130 in FIG. 2, the one extending from nucleotide at position −132 to nucleotide at position −117 in FIG. 2 and the one extending from nucleotide at position −146 to nucleotide at position −130 in FIG. 2, the one extending from nucleotide at position −146 to nucleotide at position −130 in FIG. 2 and the one extending from nucleotide at position −103 to nucleotide at position −88 in FIG. 2.

According to a preferred embodiment, the invention relates to a process for typing HCV isolates as belonging to at least one of the following HCV types: HCV type 1, HCV type 2, HCV type 3, HCV type 4, HCV type 5, HCV type 6 from a biological sample liable to contain it, and comprises the steps of:

contacting said sample in which the ribonucleotides or deoxyribonucleotides have been made accessible, if need be under suitable denaturation, with at least one probe being capable of hybridizing to a region in the domain extending from nucleotide at position −291 to nucleotide at position −66 of the 5' UR of HCV isolates represented by their cDNA sequences in FIGS. 2 and 4, with said negative numbering of the nucleotide position starting at the nucleotide preceding the first ATG codon in the open reading frame encoding the HCV polyprotein or with said probe being complementary to the above-defined probes;

detecting the complexes possibly formed between said probe and the target region, and, inferring the HCV types present from the observed hybridization pattern.

According to a preferred embodiment, the invention relates to a process for typing HCV isolates as belonging to at least one of the following HCV types: HCV type 1, HCV type 2, HCV type 3, HCV type 4, HCV type 5, and HCV type 6, and is such that the probes used are able to target one of the following target regions or said regions wherein T has been replaced by U, or the regions which are complementary to the above-said regions:

```
for HCV type 1 and 6: AAT TGC CAG GAC GAC C (No. 5)
                      TCT CCA GGC ATT GAG C (No. 6)
                      AAT TGC CAG GAY GAC C (No. 28)

for HCV type 1:       GCT CAG TGC CTG GAG A (No. 29)

for HCV type 2:       TAG CGT TGG GTT GCG A (No. 8)
                      TTR CCG GRA AGA CTG G (No. 9)
                      TGR CCG GGC ATA GAG T (No. 10)
                      TTA CCG GGA AGA CTG G (No. 11)
                      TGA CCG GAC ATA GAG T (No. 12)
                      CGT ACA GCC TCC AGG C (No. 32)
                      CCG GGA AGA CTG GGT C (No. 22)
                      CCG GAA AGA CTG GGT C (No. 23)
                      ACC CAC TCT ATG CCC G (No. 24)
                      ACC CAC TCT ATG TCC G (No. 25)
                      ATA GAG TGG GTT TAT C (No. 26)
                      GGA CCC AGT CTT CCT G (No. 33)
                      TGC CTG GTC ATT TGG G (No. 34)

for HCV type 3:       AAT CGC TGG GGT GAC C (No. 13)
                      TTT CTG GGT ATT GAG C (No. 14)
                      CCG CGA GAT CAC TAG C (No. 21)
                      CCG CAA GAT CAC TAG C (No. 36)
                      GAA TCG CCG GGT TGA C (No. 54)

for HCV type 4 and 5: AAT YGC CGG GAT GAC C (No. 17)

for HCV type 4:       TTC TTG GAA CTA ACC C (No. 18)

for HCV type 4, 3c    TTT CCG GGC ATT GAG C (No. 19)
and 3b:

for HCV type 4 and    AAT CGC CGG GAT GAC C (No. 38)
3b:

for HCV type 4:       GAG TGT TGT ACA GCC T (No. 37)
                      GAG TGT TGT GCA GCC T (No. 39)
                      AAT CGC CGG GAC GAC C (No. 40)
                      AAT GCC CGG CAA TTT G (No. 41)
                      AAT CGC CGA GAT GAC C (No. 42)
                      AAT GCT CGG AAA TTT G (No. 43)
                      AAT CGC CAG GAT GAC C (No. 49)
                      TGC CTG GAA ATT TGG G (No. 50)
                      GGA ATC GCC AGG ACG A (No. 53)

for HCV type 5:       AAT TGC CGG GAT GAC C (No. 45)
                      AAT TGC CGG GAC GAC C (No. 47)
                      TCT CCG GGC ATT GAG C (No. 46)
                      GAG TGT CGA ACA GCC T (No. 44)

for HCV type 6:       GGG TCC TTT CCA TTG G (No. 48)
``` wherein Y represents C or T, and K represents G or T, or the probes used are a set of two probes chosen from among the above-defined probes.

The invention also relates to the use of the above-defined method for determining the type(s) of HCV isolates present in a biological sample.

The term "type" corresponds to a group of HCV isolates of which the complete genome shows more than 74% homology at the nucleic acid level, or of which the NS5 region between nucleotide positions 7935 and 8274 shows more than 74% homology at the nucleic acid level, or of which the complete HCV polyprotein shows more than 78% homology at the amino acid level, or of which the NS5 region between amino acids at positions 2646 and 2758 shows more than 80% homology at the amino acid level, to genomes of the other isolates of the group, with said numbering beginning with the first ATG codon or methionine of the HCV polyprotein of the HCV-1 isolate (Kato et al., 1990). Isolates belonging to different types of HCV exhibit homologies of less than 74% at the nucleic acid level and less than 78% at the amino acid level. Isolates belonging to the same type usually show homologies of about 92 to 95% at the nucleic acid level and 95 to 96% at the amino acid level when belonging to the same subtype, and those belonging to the same type but different subtypes preferably show homologies of about 79% at the nucleic acid level and 85-86% at the amino acid level. More preferably, classification of HCV isolates should be performed according to the fact that, (1) based on phylogenetic analysis of nucleic acid sequences in the NS5b region between nucleotides 7935 and 8274 (Choo et al., 1991) or 8261 and 8600 (Kato et al., 1990) or 8342 and 8681 (Okamoto et al, 1991), isolates belonging to the same HCV type show nucleotide distances of less than 0.34, usually less than 0.33, and more usually of less than 0.32, and isolates belonging to the same subtype show nucleotide distances of less than 0.135, usually of less than 0.13, and more usually of less than 0.125, and consequently isolates belonging to the same type but different subtypes show nucleotide distances ranging from 0.135 to 0.34, usually ranging from 0.14 to 0.33, and more usually ranging from 0.15 to 0.32, and isolates belonging to different HCV types show nucleotide distances greater than 0.34, usually greater than 0.35, and more usually of greater than 0.36, (2) based on phylogenetic analysis of nucleic acid sequences in the core/E1 region between nucleotides 378 and 957, isolates belonging to the same HCV type show nucleotide distances of less than 0.38, usually of less than 0.37, and more usually of less than 0.36, and isolates belonging to the same subtype show nucleotide distances of less than 0.17, usually of less than 0.16, and more usually of less than 0.15, and consequently isolates belonging to the same type but different subtypes show nucleotide distances ranging from 0.15 to 0.38, usually ranging from 0.16 to 0.37, and more usually ranging from 0.17 to 0.36, and isolates belonging to different HCV types show nucleotide distances greater than 0.36, usually more than 0.365, and more usually of greater than 0.37, (3) based on phylogenetic analysis of nucleic acid sequences in the NS3/NS4 region between nucleotides 4664 and 5292 (Choo et al., 1991) or between nucleotides 4993 and 5621 (Kato et al., 1990) or between nucleotides 5017 and 5645 (Okamoto et al., 1991), isolates belonging to the same HCV type show nucleotide distances of less than 0.35, usually of less than 0.34, and more usually of less than 0.33, and isolates belonging to the same subtype show nucleotide distances of less than 0.19, usually of less than 0.18, and more usually of less than 0.17, and consequently isolates belonging to the same type but different subtypes show nucleotide distances ranging from 0.17 to 0.35, usually ranging from 0.18 to 0.34, and more usually ranging from 0.19 to 0.33, and isolates belonging to different HCV types show nucleotide distances greater than 0.33, usually greater than 0.34, and more usually of greater than 0.35.

According to a preferred embodiment of this invention any of the probes designated with SEQ ID NO 5, 28 and 6 may be used to identify the type 1; any of the probes with SEQ ID NO 8 to 12 or 22 to 26 and 32 to 34 may be used to identify type 2; and any of the probes with SEQ ID NO 13, 14, 36, 21, or 54 to identify type 3; and any of the probes with SEQ ID NO 17, 18 or 19 and 37 to 43 and probes of SEQ ID NO 49, 50 and 53 to identify type 4.

Probes 44 to 47 may be used to identify type 5, probe 48 may be used to identify type 6.

The following regions might also be used for discrimination of certain types: the region between positions −238 to −223 for type 2, the region between positions −244 to −229 for type 4, the regions between positions −253 to −238, or between positions −275 to −260, or between positions −293 to −278 for type 3.

The nucleotide at position −2 can also be employed to further discriminate between certain types or subtypes.

The process of the invention also comprises the discrimination and classification of subtypes of HCV, wherein besides the above-mentioned probes also probes hybridizing to the following target regions are used, or said regions wherein T is replaced by U or said regions which are complementary to the above-defined regions,

```
for HCV type 1,     CCC CGC AAG ACT GCT A   (No. 31)
subtype 1a:

for HCV type 1,     CCG CGA GAC TGC TAG C   (No. 7)
subtype 1b:         CCG CGA GAC YGC TAG C   (No. 30)
``` wherein Y represents C or T,

```
for HCV type 2,     TTR CCG GTA AGA CTG G   (No. 9)
subtype 2a:         TGR CCG GGC ATA GAG T   (No. 10)
                    CCG GGA AGA CTG GGT C   (No. 22)
                    ACC CAC TCT ATG CCC G   (No. 24)
``` wherein R represents A or G,

```
for HCV type 2,     TTA CCG GGA AGA CTG G   (No. 11)
subtype 2b:         TGA CCG GAC ATA GAG T   (No. 12)
                    CCG GAA AGA CTG GGT C   (No. 23)
                    ACC CAC TCT ATG TCC G   (No. 25)

for HCV type 2,     GGA CCC AGT CTT CCT G   (No. 33)
subtype 2c:         TGC CTG GTC ATT TGG G   (No. 34)

for HCV type 3,     AAT CGC TGG GGT GAC C   (No. 13)
subtype 3a:         TTT CTG GGT ATT GAG C   (No. 14)
                    TKT CTG GGT ATT GAG C   (No. 35)
``` wherein K represents G or T,

```
for HCV type 3,     TTT CCG GGC ATT GAG C   (No. 19)
subtype 3b:         AAT CGC CGG GAT GAC C   (No. 38)
                    CCG CGA GAT CAC TAG C   (No. 21)

for HCV type 3,     GAG TGT CGT ACA GCC T   (No. 51)
subtype 3c:         GAA TCG CCG GGT TGA C   (No. 54)
                    TTT CCG GGC ATT GAG C   (No. 19)
                    CCG CGA GAC TGC TAG C   (No. 7)

for HCV type 4,     AAT CGC CGG GAT GAC C   (No. 38)
subtype 4a or 4d:   TTT CCG GGC ATT GAG C   (No. 19)

for type 4,         AAT CGC CGG GAT GAC C   (No. 38)
subtype 4b:         AAT GCC CGG CAA TTT G   (No. 41)
                    AAT CGC CGG GAC GAC C   (No. 40)

for type 4,         AAT CGC CGA GAT GAC C   (No. 42)
subtype 4c:         AAT GCT CGG AAA TTT G   (No. 43)
                    TGC CTG GAA ATT TGG G   (No. 50)
                    GGA ATC GCC AGG ACG A   (No. 53)
                    CCG CGA GAC TGC TAG C   (No. 7)

for type 4,         AAT CGC CGG GAC GAC C   (No. 40)
subtype 4e:         GAG TGT TGT GCA GCC T   (No. 39)
                    AAT GCC CGG CAA TTT G   (No. 41)

for type 4, subtype TTT CCG GGC ATT GAG C   (No. 19)
4f:                 AAT CGC CGG GAT GAC C   (No. 38)
                    GAG TGT CGT ACA GCC T   (No. 51)
                    CCG CGA GAC TGC TAG C   (No. 7)

for type 4, subtype TGC CTG GAA ATT TGG G   (No. 50)
4g (provisional):   GGA ATC GCC AGG ACG A   (No. 53)

for type 4, subtype AAT CGC CAG GAT GAC C   (No. 49)
4h (provisional):   TGC CTG GAA ATT TGG G   (No. 50)
``` or the probes used are a set of two probes chosen from among the defined probes.

The invention also relates to the use of the above-defined method for determining the HCV subtype(s) present in a biological sample to be analyzed.

The term "subtype" corresponds to a group of HCV isolates of which the complete genome or complete polyprotein shows a homology of more than 90% both at the nucleic acid and amino acid levels, or of which the region in NS5 between nucleotide positions 7935 and 8274 shows a homology of more than 88% at the nucleic acid level to the corresponding parts of the genomes of the other isolates of the same group, with said numbering beginning with the adenine residue of the initiation coding of the long ORF. Isolates belonging to different subtypes of HCV and belonging to the same type of HCV show homologies of more than 74% at the nucleic acid level and of more than 78% at the amino acid level.

More preferably the above mentioned process relates to classification of HCV isolates into type and subtypes should be performed according to the fact that, (1) based on phylogenetic analysis of nucleic acid sequences in the NS5b region between nucleotides 7935 and 8274 (Choo et al., 1991) or 8261 and 3600 (Kato et al., 1990) or 8342 and 8681 (Okamoto et al, 1991), isolates belonging to the same HCV type show nucleotide distances of less than 0.34, usually less than 0.33, and more usually of less than 0.32, and isolates belonging to the same subtype show nucleotide distances of less than 0.135, usually of less than 0.13, and more usually of less than 0.125, and consequently isolates belonging to the same type but different subtypes show nucleotide distances ranging from 0.135 to 0.34, usually ranging from 0.14 to 0.33, and more usually ranging from 0.15 to 0.32, and isolates belonging to different HCV types show nucleotide distances greater than 0.34, usually greater than 0.35, and more usually of greater than 0.36, (2) based on phylogenetic analysis of nucleic acid sequences in the core/E1 region between nucleotides 378 and 957, isolates belonging to the same HCV type show nucleotide distances of less than 0.38, usually of less than 0.37, and more usually of less than 0.36, and isolates belonging to the same subtype show nucleotide distances of less than 0.17, usually of less than 0.16, and more usually of less than 0.15, and consequently isolates belonging to the same type but different subtypes show nucleotide distances ranging from 0.15 to 0.38, usually ranging from 0.16 to 0.37, and more usually ranging from 0.17 to 0.36, and isolates belonging to different HCV types show nucleotide distances greater than 0.36, usually more than 0.365, and more usually of greater than 0.37, (3) based on phylogenetic analysis of nucleic acid sequences in the NS3/NS4 region between nucleotides 4664 and 5292 (Choo et al., 1991) or between nucleotides 4993 and 5621 (Kato et al., 1990) or between nucleotides 5017 and 5645 (Okamoto et al., 1991), isolates belonging to the same HCV type show nucleotide distances of less than 0.35, usually of less than 0.34, and more usually of less than 0.33, and isolates belonging to the same subtype show nucleotide distances of less than 0.19, usually of less than 0.18, and more usually of less than 0.17, and consequently isolates belonging to the same type but different subtypes show nucleotide distances ranging from 0.17 to 0.35, usually ranging from 0.18 to 0.34, and more usually ranging from 0.19 to 0.33, and isolates belonging to different HCV types show nucleotide distances greater than 0.33, usually greater than 0.34, and more usually of greater than 0.35.

Using these criteria, HCV isolates can be classified into at least 6 types.

Several subtypes can clearly be distinguished in types 1, 2, 3 and 4 (1a, 1b, 2a, 2b, 2c, 3a, 3b, 3c, 4a, 4b, 4c, 4d, 4e and 40 based on homologies of the 5' UR and coding regions including the part of NS5 between positions 7935 and 8274 and the C/E1 region between nucleotides 317 and 957, and based on comparisons with isolates Z1 and DK13 as described in Bukh et al. (1993).

Further subdivision of type 4 into subtypes 4g and 4h is tentative and only based on differences in the 5' UR. An overview of most of the reported isolates and their proposed classification according to the typing system of the present invention is given in Table 1.

According to a preferred embodiment of the present invention, the probe with SEQ ID NO 31 may be used to identify subtype 1a; the probes with SEQ ID NO 7 and 30 may be used to identify subtype 1b; any of the probes with SEQ ID NO 9, 10, 22, or 24 may be used to identify subtype 2a; any of the probes with SEQ ID NO 11, 12, 23, or 25 may be used to identify subtype 2b; any of the probes with SEQ ID NO 33 or 34 may be used to identify subtype 2c; any of the probes with SEQ ID NO 13, 14, or 35 may be used to identify subtype 3a; any of the probes with SEQ ID NO 38, 19 and 21 may be used to identify subtype 3b, 4a or 4d; any of the probes with SEQ ID NO 38 or 41 may be used to identify subtype 4b; any of the probes with SEQ ID NO 42 or 43 may be used to identify subtype 4c; any of the probes in SEQ ID NO 39, 40, or 41 may be used to identify: 4e, 51, 38, 19, or 7; 4f; any of the probes with SEQ ID NO 49 or 50 may be used to identify the putative subtype 4h; any of the probes with SEQ ID NO 50 or 53 may be used to identify the putative subtype 4g.

According to a preferred embodiment of the process of the invention, the HCV types or subtypes to be discriminated are also identified by means of universal probes for HCV, such as the ones targeting one of the following regions:

```
TTG GGC GYG CCC CCG C       (No. 20)

TCT GCG GAA CCG GTG A       (No. 27)
```

According to another advantageous embodiment of the process of the invention, the hybridization step is preceeded by an amplification step of the deoxyribonucleotide or ribonucleotide containing the region to target, advantageously comprising the following steps:

contacting the biological sample liable to contain the isolate to be typed or subtyped with a set of primers, flanking the region to target, with said primers being complementary to conserved regions of the HCV genome, and preferably primers being complementary to the 5' untranslated conserved regions of the HCV genome, with said primers preferably having at least 8 contiguous nucleotides more preferably about 15, and even more preferably more than 15 contiguous nucleotides, with said contiguous nucleotides being respectively complementary to sequences chosen from the region extending from nucleotide −341 to nucleotide −171 and from the region extending from nucleotide −67 to nucleotide −1, of FIGS. 2 and 4.

Alternatively, the antisense primers could also extend into the core region or the set of primers may or/be aimed at amplifying both the 5'UR and the core region, either in 1 PCR fragment or with a set of primers for each of the two regions. Consequently, probes from the core region, able to hybrize to (sub)type specific regions in core PCR products, may be included in the line probe assay to further discriminate between types and/or subtypes, amplifying the target region, for instance via a polymerase chain reaction by means of the above-mentioned set of primers and possibly incorporating a label such as digoxigenin or biotin into the amplified target sequence, with said amplifying being repeated between 20 and 80 times, advantageously between 30 and 50 times.

According to a preferred embodiment of the invention, the analyte strand may be enzymatically or chemically modified either in vivo or in vitro prior to hybridization. Many systems for coupling reporter groups to nucleic acid compounds have been described, based on the use of such labels as biotin or digoxigenin. In still another embodiment of the invention sandwich hybridization may be used. In a preferred embodiment, the target sequence present in the analyte strand is converted into cDNA, with said cDNA being amplified by any technique known in the art such as by the polymerase chain reaction (PCR; Saiki et al., 1988), ligase chain reaction (LCR; Landegren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qb replicase (Lizardi et al., 1988; Lomeli et al., 1989).

The cDNA amplification step is preferably achieved by means of PCR technology and may consist of steps:

(a) providing a set of primers for a polymerase chain reaction method which flank the target sequence to be detected;

(b) amplifying the target region via a polymerase chain reaction method by means of the primers of (a); and in the same step an appropriate label molecule can be incorporated into the amplified target said label molecule being preferably digoxigenin or biotin.

The term "primers" corresponds to oligonucleotide sequences being complementary to conserved regions of sense or antisense strands of cDNA or RNA derived from the HCV genome; preferably of the 5' untranslated conserved regions of the HCV genome and more preferably selected from conserved regions of the 5' untranslated region of the HCV genome comprising positions −341 to −171 and −67 to −1, or the core region.

In an advantageous embodiment of the invention, the process is such that amplification consists of a double PCR step, each step involving a specific set of primers, with the said first step involving outer primers selected from the region extending from nucleotide −341 to nucleotide −186 and from the region extending from nucleotide 0.52 to nucleotide −1, and more particularly the following set:

```
CCC TGT GAG GAA CTW CTG TCT TCA CGC    (No. 1)

GGT GCA CGG TCT ACG AGA CCT            (No. 2)
``` or their complements, wherein W represents A or T, and with the second step involving nested primers selected from the region extending from nucleotide −326 to nucleotide −171 and from the region extending from nucleotide −68 to nucleotide −1 and, more particularly the following set:

```
TCT AGC CAT GGC GTT AGT RYG AGT GT    (No. 3)

CAC TCG CAA GCA CCC TAT CAG GCA GT    (No. 4)
``` wherein R represents A or G and Y represents T or C or their complements.

According to this embodiment of the invention, a double PCR is performed with outer primers in the first round including sequences as shown in SEQ ID NO 1 and 2, or their complementary sequences and with nested primers for the second round including sequences as shown in SEQ ID NO 3 and 4, or their complementary sequences.

The term "appropriate label molecule" may include the use of labeled nucleotides incorporated during the polymerase step of the amplification such as illustrated in Saiki et al. (1988) and Bej et al. (1990) and or any other method known to the person skilled in the art.

The assays as described in this invention may be improved in several ways obvious for the person skilled in the art. For example the cPCR reactions can be preceded by an RNA-capture step.

According to yet another embodiment, the present invention relates to a composition comprising at least one oligonucleotide primer, with said primers preferably having at least 15 contiguous nucleotides, with said contiguous nucleotides being respectively complementary to sequences chosen from the region extending from nucleotide −341 to nucleotide −171 and from the region extending from nucleotide −67 to nucleotide −1 (, of FIG. 2), or their complement.

According to yet another embodiment, the present invention relates to a composition comprising at least one oligonucleotide primer preferably having at least 15 contiguous nucleotides, with said contiguous nucleotides being chosen from any of the following sequences:

```
CCC TGT GAG GAA CTW CTG TCT TCA CGC     (No. 1)

GGT GCA CGG TCT ACG AGA CCT             (No. 2)

TCT AGC CAT GGC GTT AGT RYG AGT GT      (No. 3)

CAC TCG CAA GCA CCC TAT CAG GCA GT      (No. 4)
``` wherein W represents A or T, R represents A or G, and Y represents T or C,
or their complements.

According to an advantageous embodiment, the process of the invention for the simultaneous typing of all HCV isolates contained in a biological sample comprises the step of contacting one of the following elements:
either said biological sample in which the genetic material is made available for hybridization,
or the purified genetic material contained in said biological sample,
or single copies derived from the purified genetic material,
or amplified copies derived from the purified genetic material,
with a solid support on which probes as defined above, have been previously immobilized.

According to this preferred embodiment of the invention, the probes as defined above are immobilized to a solid substrate.

The term "solid substrate" can refer to any substrate to which an oligonucleotide probe can be coupled, provided that it retains its hybridization characteristics and provided that the background level of hybridization remains low. Usually the solid substrate will be a microtiter plate or a membrane (e.g. nylon or nitrocellulose).

Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin or haptens.

According to an advantageous embodiment of the invention, the process comprises the step of contacting anyone of the probes as defined above, with one of the following elements:
either a biological sample in which the genetic material is made available for hybridization,
or the purified genetic material contained in said biological sample,
or a single copy derived from the purified genetic material,
or an amplified copy derived from the purified genetic material, with said elements being previously immobilized on a support.

The invention also relates to the typing of new isolates.

More particularly the invention relates to a process for the detection and identification of novel HCV types or subtypes different from the known types or subtypes and comprising the steps of:
determining to which known types or subtypes the HCV isolate present in the biological sample belongs to, according to the process as defined above, possibly with said biological sample being previously determined as containing HCV, possibly by means of HCV antigen or antibody assays or with a universal probe for HCV, such as those defined above,
in the case of observing a sample which does not hybridize positively with at least one of the probes able to target the regions chosen from any of the two domains as defined above, sequencing the complete genome of the HCV type present in the sample, or alternatively sequencing that (the) portion(s) of the 5' untranslated region of the sample corresponding to a new type and/or subtype to be determined.

Advantageously the process for the detection and identification of novel HCV types and/or subtypes, present in a biological sample, which are different from type 1, type 2, type 3, type 4, type 5, type 6, in the case of identifying a novel type; and which are different from subtypes 1a and 1b for a type 1 HCV isolate, from subtypes 2a, 2b, and 2c for a type 2 isolate, from subtypes 3a, 3b and 3c for a type 3 isolate, from subtypes 4a, 4b, 4c, 4d, 4e, 4f, 4g and 4h for a type 4 isolate; from subtype 5a for a type 5 isolate; from subtype 6a for a type 6 isolate, in the case of identifying a novel subtype, and comprising the steps of:
determining to which known type(s) or subtype(s) the HCV isolate(s) present in the biological sample to be analyzed belongs, according to the process of the invention, possibly with said biological sample being previously determined as containing HCV, possibly by means of HCV antigen or antibody assays or with a universal probe for HCV such as the one defined above,
in the case of observing a sample which does not hybridize to at least one of the probes able to target the regions chosen from any of the type specific or subtype specific domains as defined above, more particularly not hybridizing with SEQ ID NO 5, 28 and 6 for type 1, with SEQ ID NO 8 to 12 or 22 to 26 and 32 to 34 for type 2, with SEQ ID NO 13, 14, 36, 21 or 54 for type 3, and with SEQ ID NO 17, 18, 19, 37 to 43, 49, 50 and 53 for type 4; and with SEQ ID NO 7 and 30 for subtype 1b, with SEQ ID NO 31 for subtype 1a, with SEQ ID NO 9, 10, 22 or 24 for subtype 2a, with SEQ ID NO 11, 12, 23 or 25 for subtype 2b, with SEQ ID NO 33 or 34 for subtype 2c, with SEQ ID NO 13, 14 or 35 for subtype 3a, with SEQ ID NO 38, 21 and 19 for subtype 3b, 4a or 4d, with SEQ ID NO 38 or 41 for subtype 4b; with SEQ ID NO 42 or 43 for subtype 4c; with SEQ ID NO 39, 40, or 41 for subtype 4e, with SEQ ID NO 51, 38, 19 or 7; for subtype 4f; with SEQ ID NO 49 or 50 for the putative subtype 4h; with SEQ ID NO 50 or 53 for the putative subtype 4g, sequencing the complete genome of the HCV type present in the sample, or, alternatively sequencing that (the) portion(s) of the 5' untranslated region of the sample corresponding to a new type and/or subtype to be determined.

The term "new isolates" corresponds to isolates which are not able to hybridize to any of the 9 above-mentioned regions or show reactivities which cannot be correctly interpreted as matching one of the currently known HCV types or subtypes. This special embodiment of the invention may also be performed by the steps of:

(a) screening HCV antibody-positive sera, or clinical NANB hepatitis samples, or a population of random samples, by cPCR (cDNA PCR), (b) performing a HCV LiPA with those samples from which a cPCR product has been obtained, and (c) cloning and sequencing these PCR fragments showing aberrant reactivities.

The invention also relates to a method for determining the type(s) as well as the subtypes(s) of HCV, and/or HIV, and/or HBV and/or HTLV present in a biological sample, which comprises the steps of:

providing:
  at least one of the probes as defined above, preferably the probes as defined above, enabling the genotyping (typing and/or subtyping) of HCV, and at least one of the following probes:
  probes capable of detecting oligonucleotides of HIV types 1 and/or 2 which can be present in said biological sample, and/or
  probes capable of detecting oligonucleotides of HBV subtypes, and/or sAg mutants, and/or cAg mutants which can be present in said biological sample, and/or
  probes capable of detecting oligonucleotides of HTLV-I and/or HTLV-II suspected to be in the biological sample,
possibly providing a set of primers as defined above, as well at least one of the following primers: sets of primers to respectively amplify human immunodeficiency virus (HIV), and/or HBV and/or human T-cell lymphotropic virus (HTLV) oligonucleotides, by means of PCR reaction and amplifying the oligonucleotides of HCV, and either HBV and/or HIV and/or HTLV possibly present in the biological sample,
contacting
  the biological sample in which the genetic material is made available for hybridization,
  or the purified genetic material contained in said biological sample,
  or single copies derived from the purified genetic material,
  or amplified copies derived from the purified genetic material,
  with the above-mentioned probes defined above under conditions which allow hybridization between the probes and the target sequences of isolates of HCV and at least one of the following viruses: HBV, and/or HIV, and/or HTLV,
  detecting the complexes possibly formed between the probes used and the target regions possibly present in the biological sample.

According to this embodiment, in addition to the type or subtype of HCV present in a biological sample, the invention also relates to a method for determining the type or subtype of any other parenterally transmitted viral isolate such as HTLV, HIV, HBV characterized by incorporating on one and the same strip, probes hybridizing specifically to:

the different types and/or subtypes of HCV as defined above,
human immunodeficiency viruses HIV-1 and HIV-2,
human T-cell lymphotrophic viruses HTLV-1 and HTLV-2,
the different HB surface antigen (HBsAg) mutants or HB core antigen (HBcAg) or HB precore Ag mutants.

In some test samples, different target sequences of which the specific detection is of clinical relevance are present simultaneously. For each of these target sequences a separate hybridization test with the corresponding probe should be performed. The combination of different type/subtype specific probes comprised in the art, in combination with the new and inventive HCV type/subtype-specific probes as explained in the present invention on one membrane strip could provide an easy and reliable general typing system for parenterally transmitted human viral diseases. If analyte strand amplification is necessary, a set of primers can be provided per viral organism to be differentiated and classified.

The invention also relates to a solid support, particularly a membrane strip containing, on known locations of its surface, a selection of the following probes, or their complements, or the above-mentioned probes wherein T has been replaced by U:

NO 5, NO 6, NO 7, NO 8, NO 9, NO 10, NO 11, NO 12, NO 13, NO 14, NO 15, NO 16, NO 17, NO 18, NO 19, NO 20, NO 21, NO 22, NO 23, NO 24, NO 25, NO 26, NO 27, NO 28 to 54 and NO 93 to 96, as defined above, as well as a control to determine if there is hybridization between these probes and the ribo or deoxyribonucleotide strands of HCV, liable to be contained in a biological sample in which HCV isolates are to be differentiated.

According to a specially preferred embodiment of the invention, the probes are immobilized in a line-wise fashion to a membrane strip.

In this preferred embodiment of the invention, a set of probes each applied to a known location onto the membrane strip include probes selected from the sequences with SEQ ID NO 5, 6, 7, 8, 9, 10, 11, 12, 13, 14, 15, 16, 17, 18, 19, 20, 21, 22, 23, 24, 25, 26, 27, SEQ ID NO 28 to 54, and NO 93 to 96 as well as a control line for conjugate binding.

The method of this preferred embodiment of the invention makes it possible to quickly determine the type of HCV infection. This assay provides the ability to discriminate between at least 6 different HCV types and might discriminate between at least 18 subtypes, and is a good instrument for searching for new types or (sub)types of HCV. For example, new subtypes 1c, 1d and type 7, and other new (sub)types may contain specific mutations in the regions mentioned above, which can be employed for specific detection by means of type-specific probes derived from such new sequences.

The invention also relates to a kit for the in vitro discrimination of at least one HCV isolate from a biological sample liable to contain it, and for its classification it according to the HCV type and subtype, with said kit containing a least one probe selected among any of those defined above;
a buffer or components necessary for producing the buffer enabling hybridization reaction between these probes and the cDNAs and/or RNAs of HCV isolates to be carried out;
when appropriate, means for detecting the hybrids resulting from the preceding hybridization.

The invention also relates to a kit for typing at least one HCV isolate from a biological sample liable to contain it and for classifying it according to the HCV type and subtype, with said kit containing
- possibly one universal probe as defined above,
- at least one probe selected among any of those of the invention,
- a buffer or components necessary for producing the buffer enabling hybridization reaction between these probes and the DNAs and/or RNAs of HCV isolates to be carried out;
- when appropriate, means for detecting the hybrids resulting from the preceding hybridization.

According to this embodiment, the invention also relates to a kit for genotyping (typing and/or subtyping) of HCV isolates comprising:
- a set of probes as defined above, preferentially immobilized on a solid substrate, and more preferentially on one and the same membrane, and
- possibly a set of primers as defined above,
- a set of buffers necessary to carry out the hybridization as well as the detection of the hybrids formed.

The invention also relates to a kit for typing HCV isolates belonging to at least one of the following HCV types: HCV type 1, HCV type 2, HCV type 3, HCV type 4, HCV type 5, HCV type 6 with said kit containing at least one of the probes as above defined,
- the buffer or components necessary for producing the buffer enabling hybridization reaction between these probes and the cDNAs and/or RNAs of the above-mentioned HCV isolates to be carried out;
- when appropriate, means for detecting the hybrids resulting from the preceding hybridization.

The invention advantageously relates to a kit for the discrimination and classification of HCV types and subtypes, with said kit containing:
- at least one of the probes as defined above,
- the buffer or components necessary for producing the buffer enabling hybridization reaction between these probes and the DNAs and/or RNAs of the above-mentioned HCV isolates to be carried out;
- when appropriate, means for detecting the hybrids resulting from the preceding hybridization.

It is to be mentioned that all the probes from SEQ ID NO 1 to SEQ ID NO 54 and SEQ ID NO 93 to 96 are new.

Furthermore, probes of SEQ ID NO 18, 29, 33, 34, 35, 40, 42, 43, 47, 49 and 54 are derived from new sequences.

Ethidium bromide-stained agarose gel showing the length of the nested PCR fragments. Lane A of each pair shows the PCR fragment with incorporation of Bio-11-dUTP. Lane B is the PCR fragment without Bio-11-dUTP. 1: Serum BR28, 2: Serum BR24, 3: Serum BR29, 4: Serum BR33, 5: Serum BR36, 6 and 7: negative control sera, 8: Serum JP62, 9: Serum BR23, 10: cPCR control without template, M: molecular weight markers.

FIG. 2

Alignment of the 5' UR nucleotide sequences of isolates from four different types of HCV. Boxed nucleotides indicate the positions of probes used for typing of the four different groups. The underlined nucleotides are used for subtyping within each group. The period between nucleotide –140 and –139 in most sequences corresponds to the insertion in some of the type 4 isolates. The numbering of the probes corresponds with the numbers used in Table 4.

FIG. 3

HCV LiPA Typing results of some representative sera. The strip contains 19 parallel probe lines:
A: Probe 5 (SEQ ID NO 5); B: Probe 6 (SEQ ID NO 6); C: Probe 7 (SEQ ID NO 7); D: Probe 8 (SEQ ID NO 8); E: Probe 26 (SEQ ID NO 26); F: Probe 22 (SEQ ID NO 22) and Probe 24 (SEQ ID NO 24); G: Probe 10 (SEQ ID NO 10); H: Probe 13 (SEQ ID NO 13); I: Probe 14 (SEQ ID NO 14); J: Probe 21 (SEQ ID NO 21); K: Probe 15 (SEQ ID NO 15); L: Probe 16 (SEQ ID NO 16); M: Probe 17 (SEQ ID NO 17); N: Probe 19 (SEQ ID NO 19); 0: Probe 18 (SEQ ID NO 18); P: Probe 155 (antisense probe: 5'-GGGGGCCTGGAGGCTG-3') (SEQ ID NO 97); Q: Probe 27 (SEQ ID NO 27); R: Probe 20 (SEQ ID NO 20); S: control line for conjugate binding.

The strips were hybridized with cPCR products of the following sera: Strip 1: serum BR5, Strip 2: serum BR12, Strip 3: serum BR18, Strip 4: serum BR22, Strip 5: serum BR19, Strip 6: serum BE95, Strip 7: serum BU79, Strip 8: serum BR23, Strip 9: serum JP63.

FIG. 4

Figure 2A:
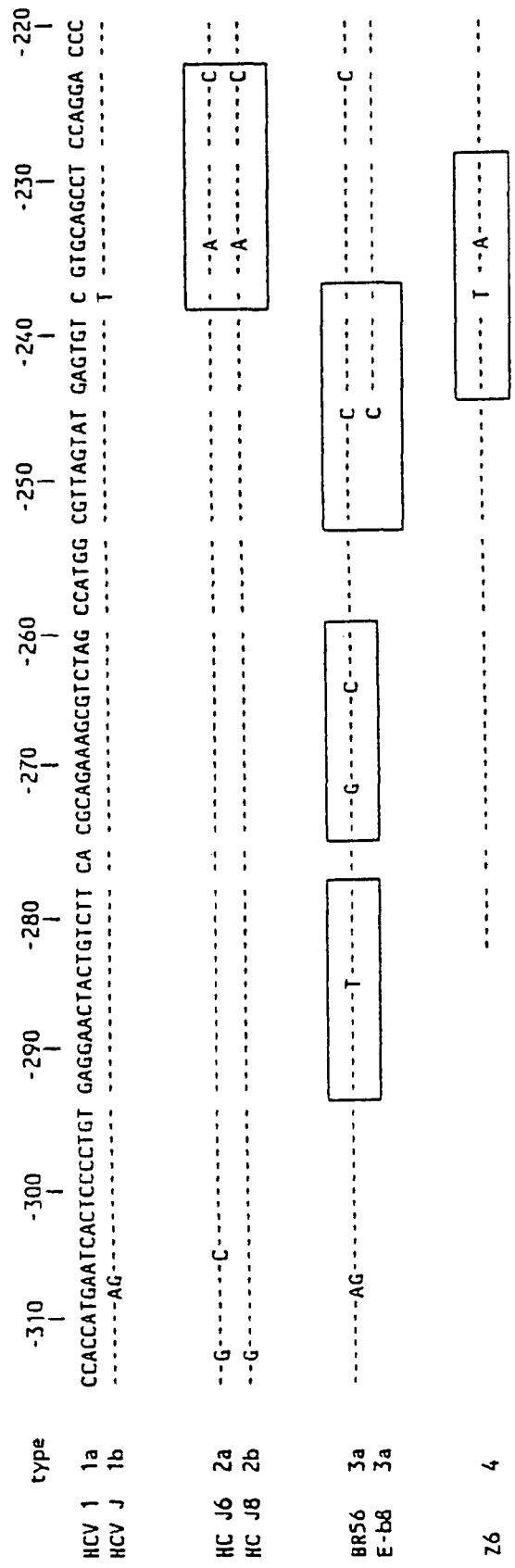
Figure 2B:
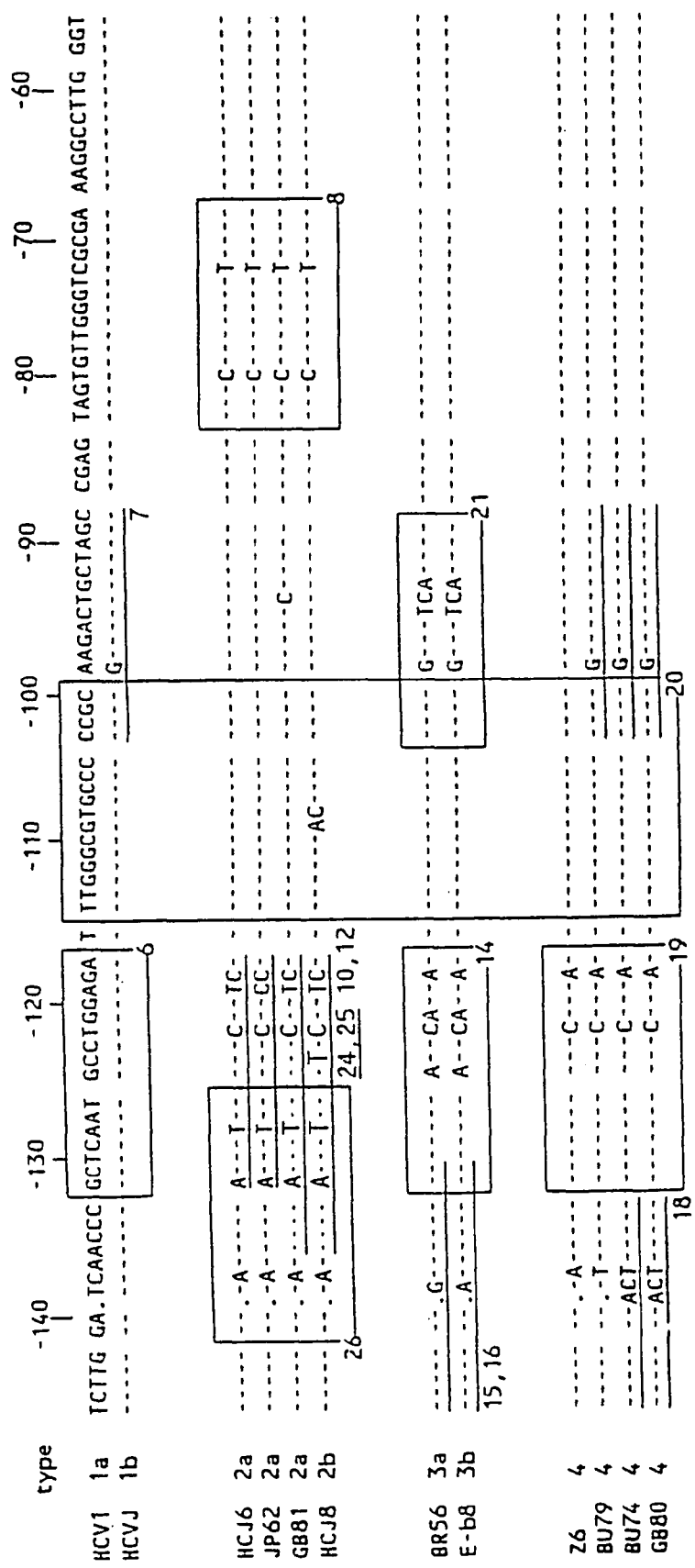

Nucleotide sequence alignment of the HCV 5' untranslated regions of new isolates BE90, BE91, BE92, BE93, BE94, BE95, BE96, BE97, BE98, BE99, GB48, GB116, GB358, GB569, GB549, GB809, CAM600, CAM736, GB478, GB724, and GB438, with sequences of HCV type 1a (HCV-1), 1b (HCV-J), 2a (HC-J6), 2b (HC-J8), 3a (BR56), 3b (HCV-TR), 5 (SA1), 6 (HK1). The sequences used to construct this alignment are taken from the EMBL database and have the following accession number: [1] M62321, [2] D10749, [3] D00944, [4] D01221, [5] D13448, [6] D11443, [7] M84838, and 8 L08156. The sequences between nucleotides –220 and –180 are not shown, they are identical to HCV-I in all isolates. '-', nucleotide is identical to the corresponding nucleotide in HCV-1; '..', gap created between –145 and –144 to allow alignment with type 6 sequences which have a CA insertion; '.', gap created between –138 and –137 in most of the sequences to preserve alignment with sequences which have an extra nucleotide at that position. * refers to the conserved HCV sequence between residues –220 and –180 as shown in FIG. 2.

FIG. 5

Amino acid sequence alignment of the NS5 sequences of isolates BE90, BE91, BE92, BE93, BE95, GB358, GB549, and GB809 with known sequences as described in Table 6.

FIG. 6

Line probe assays including probe with SEQ ID NO 32, tested with type 1 and 2 sera. 1, type 1b serum BE82, 2, type 2a serum JP62, 3, type 2b serum BE91, A, conjugate control, B, probes 20 and 27, C, probe 8, D, probe 26, E, probe 32 (SEQ ID NO 32).

FIG. 7

Line probe assays including probes with SEQ ID NO 33 and 34, tested with type 2a, 2b, and 2c sera. 1, type 2a serum JP62, 2, type 2b serum BE91, 3, type 2c serum BE92, A, conjugate control, B, probes 20 and 27, C, probe 8, D, probe 26, E, probe 32, F, probe 22, G, probe 24, H, probe 23, I, probe 25, J, probe 33 (SEQ ID NO 33), K, probe 34 (SEQ ID NO 34).

FIG. 8

Line probe assays including probes with SEQ ID NO 31, 37 and 38, tested with type 4 sera. 1, type 4a serum GB116, 2, serum GB113, 3, type 4f serum GB438, A, conjugate control, B, probes 20 and 27, C, probe 37 (SEQ ID NO 37), D, probe 38 (SEQ ID NO 38), E, probe 19, F, probe 31 (SEQ ID NO 31), G, probe 7.

FIG. 9

Line probe assays including probes with SEQ ID NO 44, 45 and 46, tested with type 4a and 5a sera. 1, type 5a serum 3E95, 2, type 4a serum GB116, A, conjugate control, B, probes 20 and 27, C, probe 44 (SEQ ID NO 44), D, probe 45 (SEQ ID NO 45), E, probe 46 (SEQ ID NO 46), F, probe 31 (SEQ ID NO 31), G, probe 7.

FIG. 10

Line probe assays including probes with SEQ ID NO 93, 94, 95, and 96, tested with type 4a and 5a sera. 1, type 4a serum GB116, 2, type 5a serum BE95, A, conjugate control, B, probes 20 and 27, C, probe 93 (SEQ ID NO 93) applied at a concentration of 0.4 pmol/µl, D, probe 94 (SEQ ID NO 94) applied at a concentration of 2.5 pmol/µl, E, probe 94 (SEQ ID NO 94) applied at a concentration of 1.0 pmol/µl, F, probe 94 (SEQ ID NO 94) applied at a concentration of 0.4 pmol/µl, G, probe 95 (SEQ ID NO 95) applied at a concentration of 2.5 pmol/µl, H, probe 95 (SEQ ID NO 95) applied at a concentration of 1.0 pmol/µl, I, probe 95 (SEQ ID NO 95) applied at a concentration of 0.4 pmol/µl, J, probe 96 (SEQ ID NO 96) applied at a concentration of 0.4 pmol/µl.

TABLE 1

Overview of the different classification systems.

Table 2

Figure 3:
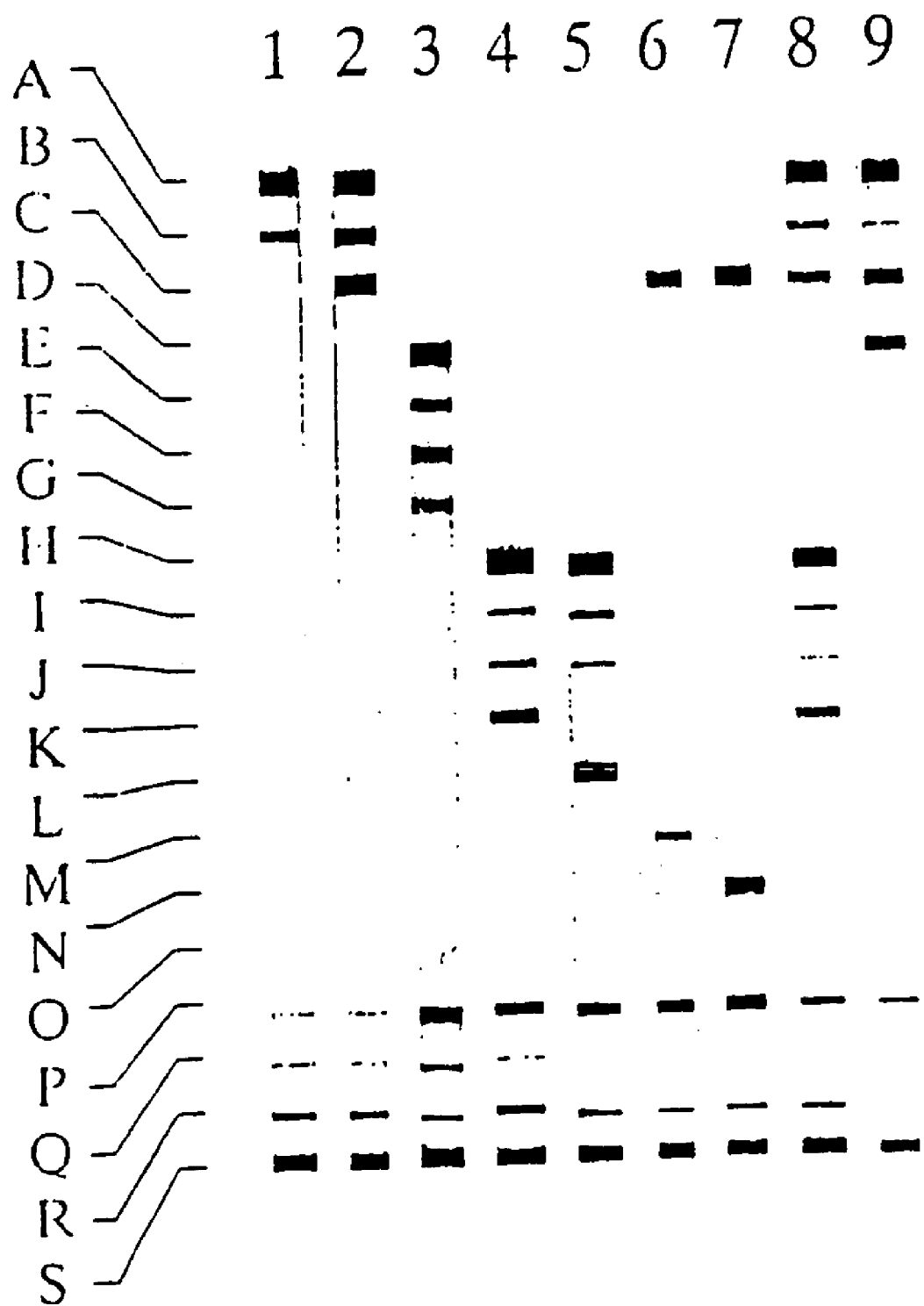

Interpretation of the results shown in FIG. 3.

Table 3

Final results of HCV LiPA typing and HCV antibody assays.

A summary of the typing in relation to the serology is presented. The INNO-LIA HCV Ab assay contains one line with NS4 epitopes, one line with NS5 epitopes, and 4 lines with core epitopes. Only the highest score for the core lines is given. The intensity of the signal is given by a number: 0=negative; 9=indeterminate; 1 to 3=positive. The final interpretation of the antibody test is given in the LIA column: 1=positive; 0=negative; 9=indeterminate.

The signal-to-noise ratio of the sera tested in the Innotest HCV Ab is also given for some of the sera.

Table 4

Nucleotide sequence, position, and orientation of the primers and probes.

Table 5

Overview of new probes designed from new types and subtypes of HCV. The type or subtype for which classification is possible or improved, the sequence, and the SEQ ID NO. are shown.

* represents a probe which does not type or subtype all isolates found representing said type or subtype. The underlined letters indicate provisional divisions into subtypes.

Table 6

Sequence homology between BE90, BE91, BE92, BE93, BE95, GB358, GB549, and GB809 and published sequences in the HCV NS5 region from nucleotide 7935 to 8274, according to the numbering used in the present invention. Homology scores within the same subtype are in bold. Published sequences used to perform homology calculations were taken from the EMBL database and have the following accession numbers: M62321, [2] D10749, [3] M67463, [4] D90208, [5] x61596, [6] L02836, [7] M84754, [8] D10750, [9] D11168; D01171, [10] S38204, [11] M58335, [12] D10078, [13] D10079, [14] D10080, [15] D10081, [16] D00944, and [17] D01221. All of them represent complete genomes, except [12], [13], [14], [15] and [18] for which NS5 sequences were published. [18] was published in the Chiron patent WO 92/19743, SEQ ID NO 18.

EXAMPLES

In order to study the natural variation of HCV isolates obtained from different geographical areas throughout the world, a rapid means for typing and subtyping of HCV isolates in the form of a Line Probe Assay (LiPA) was developed.

Essentially, a cPCR fragment containing incorporated biotinylated dUTP is hybridized to oligonucleotides which are immobilized on a nitrocellulose membrane. The stable hybridization duplex is then revealed by streptavidin-labelled alkaline phosphatase, and subsequent color development with NBT (nitro 42 blue tetrazolium) and BCIP (bromo-chloro-indolyl phosphate). The cPCR fragment is synthesized from the 5' UR of any HCV RNA using highly conserved sets of primers. The oligonucleotides used for typing are directed against the internal type-specific variable parts of the cPCR fragment. In fact, the 2 variable regions between positions −170 and −155, and between −132 and −117 in the linear sequence may be part of a stem in the folded viral RNA, and mutations in the first region may be complemented by another mutation in the second region to allow or disallow RNA duplex formation. Variation and conservation is expected to occur at the same positions in other new types of HCV as well and, therefore, this variable region might remain instrumental for the discrimination between all current and yet-to-be discovered types of HCV. Moreover, since higher variabilities compared to the 5' UR are observed in the core, NS3, and NS5 regions, typing in these regions employing universal sets of primers might no longer be tenable.

The proposed nomenclature of this invention is provisional and could still be subject to amendments according to new guidelines that may be set forward by international committees. For example, subtype 4a might be changed into another type 4 subtype, like 4c or 4e, and type 4 might be changed into type 5 or 6, in which case type 4a might become 6c, for example. However, new classification systems will not hamper classification of a certain group of isolates classified into a type or subtype by means of the proposed probes of the invention.

1. Serum Samples Used for Typing and Subtyping

Sixty-one Brazilian samples (BR1 to BR61) were tested in the HCV Antibody ELISA assay (Innotest HCV Ab, Innogenetics) as well as in the Inno-LIA HCV Ab test (Innogenetics). The first 23 serum samples (BR1 to BR23, Table 3) were taken from hemodialysis patients with either high ALT levels or positive Inno-LIA results, or from blood donors from which the recipient developed NANB hepatitis liver disease. Fourteen (BR24 to BR37) of the other serum samples were randomly chosen; the 24 remaining sera (BR38 to BR61) were selected on the basis of their LIA pattern. Most of the latter showed weakly positive, indeterminate, or negative reactivity with the NS4 and NS5 synthetic peptides on the LIA. The following sera were also included in this typing effort: two pools of Japanese sera (JP62 and J63), six Belgian sera (BE64 to BE69), four sera from the Netherlands (NE70 to NE73), six sera from Burundi (BU74 to BU79) and two sera from Gabon (GB80 and GB81). They were all tested with the Inno-LIA HCV Ab assay system. The sera BU74 to BU78 were only positive for anti-core antibodies, while the serum BU79 reacted only with the NS5 line. Both Gabonese sera were LIA HCV negative (Inno-LIA HCV), HIV negative (Innotest HIV), but HTLV positive (Innotest HTLV). One serum from Belgium (BE69) and one from the Netherlands (NE73) were completely negative. Three of the NF-sera (NE71 to NE73) were selected because they were negative in the second generation RIBA test (Ortho Diagnostics Inc.).

2. cPCR, Analysis of the PCR Product, and Cloning

The primers used for the PCR reactions were complementary to the conserved areas of the 5' UR of the different HCV types. Degeneration was included to allow annealing to type 1 and type 2 sequences (Kato et al, 1990; Nakao et al, 1991; Okamoto et al., 1991) and to the sequence of our type 3 clone (BR56; accession number D13448, DDJJB/EMBL/GenBank DNA data base deposited on 21/10/1992). The sequences of the outer PCR primers (HcPr98, SEQ ID NO 1 and HcPr29, SEQ ID NO 2) and of the nested PCR primers (HcPr95, SEQ ID NO 3 and HcPr96, SEQ ID NO 4) are listed in Table 4. The probes used for the detection of the different serum types are also listed in Table 4. All oligonucleotides were synthesized on a 392 DNA/RNA Synthesizer (Applied Biosystems).

Viral RNA was extracted from serum essentially as described by Chomczynski and Sacchi (1987) with minor modifications. The RNA was coprecipitated with 20 µg Dextran T500 (Pharmacia). The RNA pellet was briefly dried and resuspended in 10 µl DEPC-treated $H_2O$. After adding 2 µl 150 ng/µl random primers (Pharmacia) and denaturatine for 10 minutes at 65° C., the first strand cDNA synthesis was carried out in 20 µl at 42° C. in the presence of 25 U HPRI (Amersham), 500 µM dATP, dCTP, dTTP and dGTP, 1×AMV buffer (Stratagene) and 2.5 U AMV-RT (Stratagene). Seven µl of the resulting cDNA was amplified in an outer PCR over 40 cycles each consisting of 1 min 95° C., 1 min 55° C. and 1 min 72° C. in a total volume of 50 µl. The solution was adjusted to a final concentration of 200 µM of dATP, dCTP, dTTP and dGTP, 1×Taq buffer (Stratagene), 0.2 µM of each primer, and 1 U Taq polymerase (Stratagene). One p. 1 of the first round amplification product was amplified with the nested primers again for 40 cycles in a buffer with the same composition. For HCV typing, the nested PCR contained 40 µM Bio-11-dUTP (Sigma) and 160 µM of dTTP. Both the outer and the nested PCR product were then subjected to electrophoresis in a 2% low melting point (NuSieve GTG, FMC)/1% Ultra Pure (Gibco BRL) agarose gel. After ethidium bromide staining, PCR fragments were cut out from the agarose gel, the DNA was recovered by centrifugation through a 0.45 µm HV membrane (Millipore), purified by two phenol/chloroform and two ether extractions, precipitated, and subsequently polished with T4 DNA polymerase (Boehringer), kinated with T4 kinase (Boehringer), and finally ligated in the dephosphorylated Eco RV site of pBluescript KS(−) (Stratagene). Plasmid DNA preparation was as described in the alkaline lysis method (Maniatis et al., 1982). Sequencing reactions were carried out on double-stranded plasmid DNA with T7 and T3 primers by using the Deaza G/A T7 sequencing mixes (Pharmacia).

The results of these sequencing reactions are shown in FIG. 2. The following sequences were deposited in DNA databases (BR56: DDBJ/EMBL/Genbank accession number D13448; BU74: DDBJ/EML/GenBank, accession number D13449; BU79: accession number D13450; GB80: accession number D13451; GB81: accession number D13452; GP62: accession number D13453).

Figure 1:
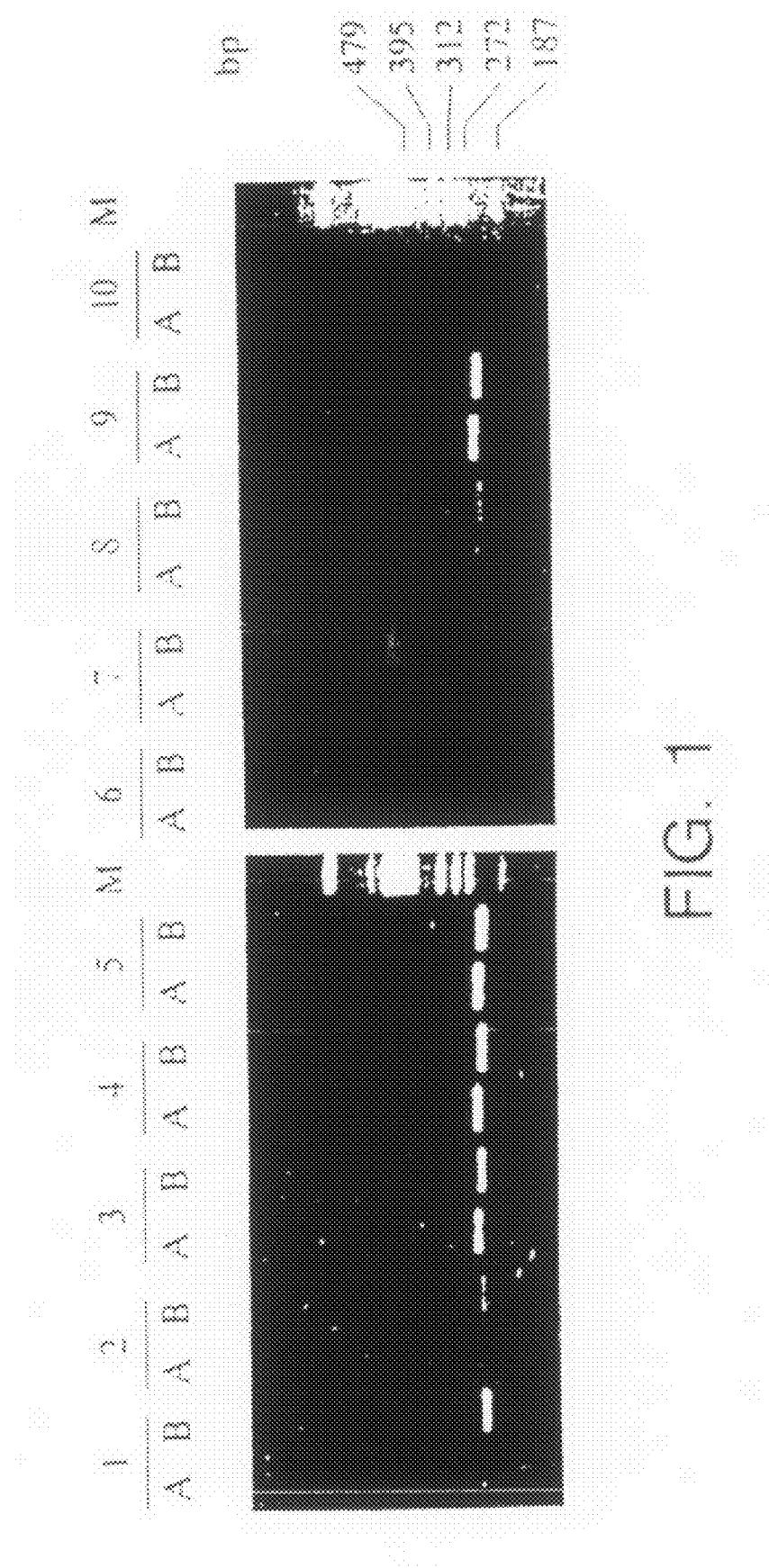
FIG. 1

Serum RNA from HCV-infected patients was used as template for cDNA synthesis, which in turn was a template for nested PCR. Two sets of PCR primers were designed: HcPr98 (SEQ ID NO 1) and HcPr29 (SEQ ID NO 2) for the outer reaction, HcPr95 (SEQ ID NO 3) and HcPr96 (SEQ ID NO 4) for the nested reaction (Table 4). These four primers were chosen to match the published sequences (Kato et al., 1990; Nakao et al., 1991; Okamoto et al., 1991) and the sequence of a clone obtained from the untranslated region of isolate BR56. (see FIG. 2). The resulting amplification product of the nested PCR is 235 base pairs (bp) long. Due to the incorporation of Bio-11-dUTP, there is a decrease in mobility which is clearly visible after agarose gel electrophoresis (FIG. 1). The size of the DNA fragments is the same for all the different HCV types, suggesting that a second experiment, like restriction enzyme digestion or hybridization, is necessary for classification. A membrane strip containing immobilized HCV-specific oligonucleotide probes applied as parallel lines was therefore developed. These strips are hybridized with PCR amplified DNA fragments of the 5' UR into which biotinylated nucleotides were incorporated during synthesis. After hybridization, streptavidin labelled with alkaline phosphatase is added and becomes bound to the biotinylated hybrids formed during the hybridization. After incubation with NBT/BCIP, a purple precipitate appears.

3. Preparation of the Line Probe Assay (LiPA) Strips

The 16-mer oligonucleotides, specific for the different types or subtypes of HCV (Table 4, number 5 to 27), were provided with a poly-(dT) tail at their 3' end as follows: 20 pmol of primer was incubated in 25 µl buffer containing 3.2 mM dTTP, 25 mM Tris.HCl (pH 7.5), 0.1 M sodium cacodylate, 1 mM $CoCl_2$, 0.1 mM dithiothreitol, and 60 U Terminal deoxynucleotidyl Transferase (Pharmacia) for 1 hour at 37° C. The reaction was stopped by adding 2.5 µl 0.5 M EDTA (pH 8.0) and diluted with 20×SSC (Maniatis et al., 1982) until a final concentration of 6×SSC and 2.5 pmol oligonucleotide/µl was reached.

One pmol of this solution was applied over a distance of 4 mm on a nitrocellulose membrane. As control for the conjugate, biotinylated DNA was applied alongside. The oligonucleotides were fixed to the membrane by baking at 80° C. for two hours. The membrane was then sliced in 4-mm strips.

4. LiPA Test Hybridization and Color Development

Ten µl of the nested PCR amplification product, containing incorporated Bio-11-dUTP, is mixed with 10 µl of 400 mM NaOH/10 mM EDTA and incubated at room temperature (RT) for 10 minutes. Then, 1 ml prewarmed (37° C.) hybridization buffer containing 3 M tetramethylammonium chloride (TMACl, Merck), 50 mM sodium phosphate (pH 6.8), 1 mM EDTA, 5×Denhardts (Maniatis et al., 1982), 0.6% (w/v) SDS and 100 µg/ml sheared salmon sperm DNA is added and the hybridization is carried out in a shaking water bath at 42° C. for 2 hours (Jacobs et al., 1988). The strips are washed 2 times at RT for 5 minutes with 1 ml prewarmed (37° C.) wash buffer (3 M TMACl, 0.2% SDS, 50 mM Tris.HCl, pH 8.0), followed by a stringent wash at 51° C. for 30 minutes and two brief washing steps at RT. At this moment, the wash buffer is replaced by Rinse Solution (phosphate buffer containing NaCl, Triton, 0.5% $NaN_3$; Inno-Lipa, Innogenetics, Antwerp, Belgium) and the strips are rinsed twice with 1 ml at RT. Finally, the strips are rinsed with Conjugate Diluent (phosphate buffer containing NaCl, Triton, protein stabilizers, 0.1% $NaN_3$; Inno-Lia, Innogenetics, Antwerp, Belgium) and incubated with Conjugate Diluent containing 4000× diluted streptavidin, labelled with alkaline phosphatase (Gibco BRL) for another 30 minutes at RT. The strips are washed again 3 times with Rinse Solution and once with Substrate Diluent (Tris buffer containing NaCl and $MgCl_2$; Inno-Lia, Innogenetics, Antwerp, Belgium). Color development is achieved by adding BCIP and NBT to the Substrate diluent and incubation of the strips for 30 minutes at RT. The color development is stopped by replacing the buffer with distilled water.

5. A LiPA for Discrimination Between HCV Types 1, 2 and 3

The sequences for the probes against type 3 were derived from a cPCR clone from serum BR56 (accession number D13448). When comparing the published type 1 sequences with BR56, two regions of 16 nucleotides containing 4 to 6 mutations could be observed each time. Surprisingly, when type 2 sequences became available, variation was again maintained in these two regions. Therefore, the position of the typing probes was chosen in those regions with a relatively low degree of homology between types, but good conservation within one type. In a first version of the strips, a total of eight separately immobilized oligonucleotides were applied. Two of them were directed against type 1 (HcPr124, SEQ ID NO 5 and HcPr125, SEQ ID NO 6), four against type 2 (HcPr136, SEQ ID NO 9 and HcPr137 (SEQ ID NO 10) for type 2a, HcPr126 (SEQ ID NO 11) and HcPr127 (SEQ ID NO 12) for type 2b) and two against type 3 (HcPr128, SEQ ID NO 13 and HcPr129, SEQ ID NO 14) HCV (Table 4).

cPCR products were synthesized from 23 Brazilian sera (BR1 to BR23) and, after hybridization, 17 of them recognized the 16-mers of type 1. Four type 3 sera were found, as well as one type 2a serum. Serum BR23 was co-infected with type 1 and type 3. Two pools of Japanese sera were subsequently tested: JP63 reacted with the type 1 and type 2a probes, and the majority of the JP62 pool contained type 2a sequences. After cPCR cloning and sequencing the region between the primers HcPr95 (SEQ ID NO 3) and HcPr96 (SEQ ID NO 4), the sequence of JP62 (FIG. 2) was confirmed as type 2a. The type 2b probes HcPr126 (SEQ ID NO 11) and HcPr127 (SEQ ID NO 12), to which JP62 did not react, differed by only one and two nucleotides, respectively, from the sequence of JP62 (accession number D13453). Therefore, the chosen hybridization and washing conditions were very stringent and that even single mismatches abolish hybridization in this assay.

6. Discrimination Between Subtypes

After careful comparison of all available type 1 coding sequences, two subtypes (1a and 1b) can clearly be distinguished, with an average genome homology of 79%. In the 5' UR, only 2 mutations were observed between HCV-J and HCV-1 in the region of the nested PCR product, resulting in 98.8% homology. Although only 2 mutations were present between HCV-1 (1a) and HCV-J (1b), the A-to-G transition observed at position −99 occurs in all type 1b isolates studied so far. Therefore, hybridization to probe HcPr138 (SEQ ID NO 7), which spans the region of the G substitution, is indicative of a type 1b isolate.

When comparing all available 5' UR sequences of type 3 (present invention; Bukh et al., 1992; Chan et al., 1992; Lee et al., 1992), the isolates could be divided into two groups according to the presence of a common G (type 3a; HcPr140, SEQ ID NO 15) or a more rare A (type 3b; HcPr139, SEQ ID NO 16) at position −139. Discrimination between types 2a and type 2b (or K2a and K2b) could be made in the variable regions as reported above.

The combination of all these type- and subtype-specific probes for type 1 and 3 (Table 4) allowed us to separate the 17 Brazilian sera which previously had been characterized as type 1 into 8 type 1a and 9 type 1b sera. Three of the four type 3 sera formed hybrids with the type 3a line. Different molecules in the cPCR fragment of the co-infected serum BR23 hybridized with the lines for type 1b and type 3a (FIG. 3, strip 8).

Another 38 Brazilian sera (BR24 to BR61) were tested in this new LiPA. The most dominant criterium for the selection of these sera was the absence of antibodies for NS4 and NS5 epitopes, since earlier reports showed that there was a low degree of cross-reactivity between type 2 and type 3 anti-NS4 antibodies with type 1 NS4 antigens (Chan et al., 1991). Of the 38 Brazilian sera, 12 could be typed as type 1a, 14 as type 1b, 9 as type 3a, 2 as type 3b and a coinfection of type 1b and 3a. It was concluded that all the tested Brazilian sera could be typed. It remains to be determined whether the discrimination between type 3 subtypes is relevant. As no sequence data from the 5' UR of the Ta and Tb isolates (Mori et al., 1992) has been published, our division into type 3a and 3b is still tentative. More data about the serology and the sequences of the open reading frame are needed to confirm type 3 and type 4 subtyping.

7. Identification of Type 4 Isolates and Incorporation of Type 4-Specific Probes in the LiPA PCR fragments amplified from 6 Burundian sera (BU74 to BU79) failed to react with any of the 16-mers on the strips. Three PCR fragments from these Burundian samples (BU74: accession number D13449, which was identical to BU76, and BU79: accession number D13450; FIG. 2) were cloned and sequenced. Sequences that were clearly different from most of the previously described types were obtained. The Burundian samples are related to each other, and to Z6 (Bukh et al., 1992) and show higher homologies to type 1 than to type 3 or type 2. However, most of the differences with type 1 were again located in the variable regions. The most surprising finding was the presence of one extra nucleotide in BU74 and BU76 between the positions −139 and −140. These results argue in favor of the existence of new HCV type(s) or subtype(s), which will be provisionally called type 4. The sequences of the 5' UR of the virus that could be amplified from these African sera were strongly divergent from the previously described types. Therefore, these isolates have been tentatively designated as type 4. Similar sequences communicated in the study of Bukh et al. (1992), also originated from Africa, although one was from Denmark. FIG. 2 shows that in the region between nucleotides −291 and −55, as many as 8 nucleotide variations are possible within this group. It is likely that type 4 is further composed of several subtypes, or that these subtypes are divergent subtypes of type 1.

After obtaining these data, the LiPA was improved in three ways. First, oligonucleotide HcPr142 (SEQ ID NO 20), carrying one degeneration, was chosen from a highly conserved region as universal HCV probe for the confirmation of the presence of the PCR product (Table 4). Secondly, three oligonucleotides were synthesized for identification of the type 4 sequences (HcPr144, SEQ ID NO 17 with one degeneration, HcPr145, SEQ ID NO 18 and HcPr146, SEQ ID NO 19; Table 4). Thirdly, a universal type 2 probe was selected outside the variable regions (HcPr147, SEQ ID NO 8, Table 4), since a universal probe for the detection of type 2 could not be chosen from the regions between positions −170 and −155 and between positions −132 to −117.

With this version of the LiPA, the 6 PCR fragments from the Burundian sera (Table 3) were classified as type 4 as expected (FIG. 3, strip 6 and 7). Two Gabonese sera, 4 sera from the Netherlands and 6 Belgian sera were also included in the screening. From GB80 a type 4 HCV 5' UR could be amplified, which was cloned and sequenced (FIG. 2). The other Gabonese serum GB81 showed a coinfection of a variant of type 2 (cloned and sequenced, FIG. 2) and type 4. The latter gave the same typing pattern as BU79 (FIG. 3, strip 7). To establish whether reaction of GB81 with the type 2 and type 4 probes was caused by unexpected cross-reactivity between typing probes, or merely the result of a coinfection, the cPCR product was cloned and 17 individual colonies were subjected to PCR and HCV LiPA. Ten (59%) colonies contained type 4 inserts and seven were type 2 (41%), clearly indicating the co-circulation of 2 types of HCV in the same serum. For the three NE-sera which were negative in the Ortho RIBA test and positive (NE71), indeterminate (NE72)

or negative (NE73) in the Inno-LIA HCV Ab test, it could be shown that type 3a isolates were present. The fourth NE serum, which showed good reactivities in both Ortho RIBA and INNO-LIA, contained a type 1a isolate. Finally, from the 6 Belgian sera analyzed, BE64 to BE67 were infected with type 1b strains. One patient of Italian origin (BE68) had a type 2a infection, and BE69 contained type 3a sequences. The latter was obtained from a case of chronic, viral-like NANB hepatitis, but was negative in all second generation assays and anti-NS3, anti-E1, and anti-E2 research assays. This serum had a very low virus titer and became weakly positive only after the second round of PCR in four different samples taken during 2 years, showing the need for nested cPCR in HCV diagnosis. The sequence of the nested PCR fragment was identical with BR56. This was not surprising, since type 3 strains show very little sequence variation.

In total, 19 different oligonucleotides were used for this version of the LiPA strips as shown in FIG. 3. Because some of the oligonucleotides are directed against the same HCV subtype, probe HcPr156 (SEQ ID NO 22) was pooled with HcPr158 (SEQ ID NO 24) for type 2a. The oligonucleotides against type 4 were applied separately because too little sequence information from the coding region is known at this moment and hence, no division into subtypes (if any) can be made as yet. The presence of an extra base in some of the type 4 sequences can form the basis for further attempts to subtype this group. The results obtained with some representative sera are shown in FIG. 3. The interpretation of these strips is given in Table 2.

In this study, 61 PCR-positive Brazilian HCV sera were typed. Twenty (33%) sera had a type 1a HCV infection, 23 (38%) were type 1b, one (1.5%) type 2a, 15 (24.5%) type 3, and two (3%) sera with coinfections were found. The recognition of coinfected sera is illustrated by BR23 (FIG. 1, lane 9; FIG. 3, strip 8). The remaining 20 sera were collected from 5 different countries; 8 of the sera originated from two African countries.

In a minority of the cases such as was the case for BE67, a type 1b PCR fragment recognized the 3b subtype probe HcPr139 (SEQ ID NO 16). This can be explained by assuming that the 1b sequence of serum BE67 has an A instead of a T at position −139. The results obtained with the JP62 (accession number D 13453) sequence, where one mismatch in the oligonucleotide abolishes the hybridization signal, further supports this assumption. Since isolate-specific mutations are scattered throughout the 5' UR, it is possible that an isolate of a given type also hybridizes to a subtyping probe of another type (see FIG. 3, strips 6 and 7). Such reactivities merely indicate the presence of the sequence of the subtyping probe in the isolate studied. However, reactivities with multiple typing probes were never observed, unless a serum was coinfected, as investigated for GB81.

In general, when a type 1a cPCR product hybridized on the LiPA, the sequence of the probes HcPr124 (SEQ ID NO 5), HcPr125 (SEQ ID NO 6) and HcPr142 (SEQ ID NO 20) must be present in the nested cPCR fragment. Consequently, 48 (26%) by of 184 by (FIG. 2) are immediately known. Following the same reasoning, it can be calculated that for isolates similar to the HCV J type 33%, to the HC J6 type 35%, to the BR56 type 34%, to the Z6 and BU77 type 26%, to the BU74 type 41% and to the BU79 type 32% of the sequence is known. However, it must be taken into account that due to the degeneration of some of the 16-mers, some information is lost and, hence, these percentages are maximum scores. Nevertheless, this approach supports the idea of the sequencing by the hybridization principle (Strezoska et al., 1991).

When comparing LiPA with antibody reactivity of these sera in our Inno-LIA HCV Ab assay (Table 3) some correlations between genotypes and their phenotypes (serotype) emerge. The type 3 and 4 sera from Belgium, the Netherlands, Gabon, and Burundi all react very weakly positive, indeterminate, or negative in the second generation antibody assays. The weakly positive reaction is mostly caused by anti-core antibodies, whereas antibodies against the IAA NS4 and NS5 epitopes are usually absent. This is in agreement with the high conservation of core sequences encoding only slightly different epitopes which allow immunological cross-reaction. Epitopes for the NS4 and NS5 region are located in highly variable regions, disabling most of the immunological cross-reaction. As the current antibody assays contain type 1 epitopes, it is possible that a few percent of type 2, type 3, and type 4 infected sera will show a negative result. However, the conclusion of lack of cross-reaction of the type 3 Brazilian sera with type 1 NS4 and NS5 antigens cannot be drawn from our results (Table 3). For the 14 randomly chosen sera (BR24 to BR37; Table 3), there was 100% correlation between the LIA reactivity and the 9 type 1 viruses. From four type 3 sera, two (BR34 and BR36) reacted with NS4 and three (BR33, BR34 and BR35) with NS5. BR37 was not taken into account because of the coinfection. When all serological data of the 77 sera infected by a single type were analyzed, 58% and 44% of the type 1 sera recognized the NS4, and NS5 epitopes, respectively. These percentages are rather low and due to the selection criteria. For the type 3 sera, 37% and 53% were reactive with the NS4 and NS5 epitopes, respectively. It is possible that higher cross-reactivities are observed in high-risk groups, such as in those samples obtained from Brazil, as compared with results in European blood donors (present invention and Chan et al., 1992). Such cross-reacting sera could be induced by multiple infections, some of which occur simultaneously, but others might occur after one another. A previous anti-HCV memory could be boosted by new HCV infections and result in co-circulation of viruses of one type with antibodies mainly directed against another type. Such an explanation is plausible for serum BR56, which has been typed as HCV type 3, but contained antibodies to type 1 core, E1, E2, NS3, NS4, and NS5 (data not shown). It remains to be determined whether anti-type 3 antibodies are present in this serum.

Besides the differences in immune response, different HCV types could also show different progression to long-term liver disease, as has already been reported (Okamoto et al., 1992a).

In conclusion, the LiPA allows a rapid determination of the type of HCV infection. This assay has the ability to discriminate between 4 different HCV types and 8 subtypes, and is a good means for determining new types.

Moreover, this assay can be further improved by, for example, replacing the cPCR reactions by the RNA-capture PCR. Finally, this assay could prove to be instrumental in further establishing the relation between genotypes, future serotypes, and the clinical status or outcome of the disease.

8. Identification of New Types and Subtypes and Probes Useful for their Classification.

Figure 5A:
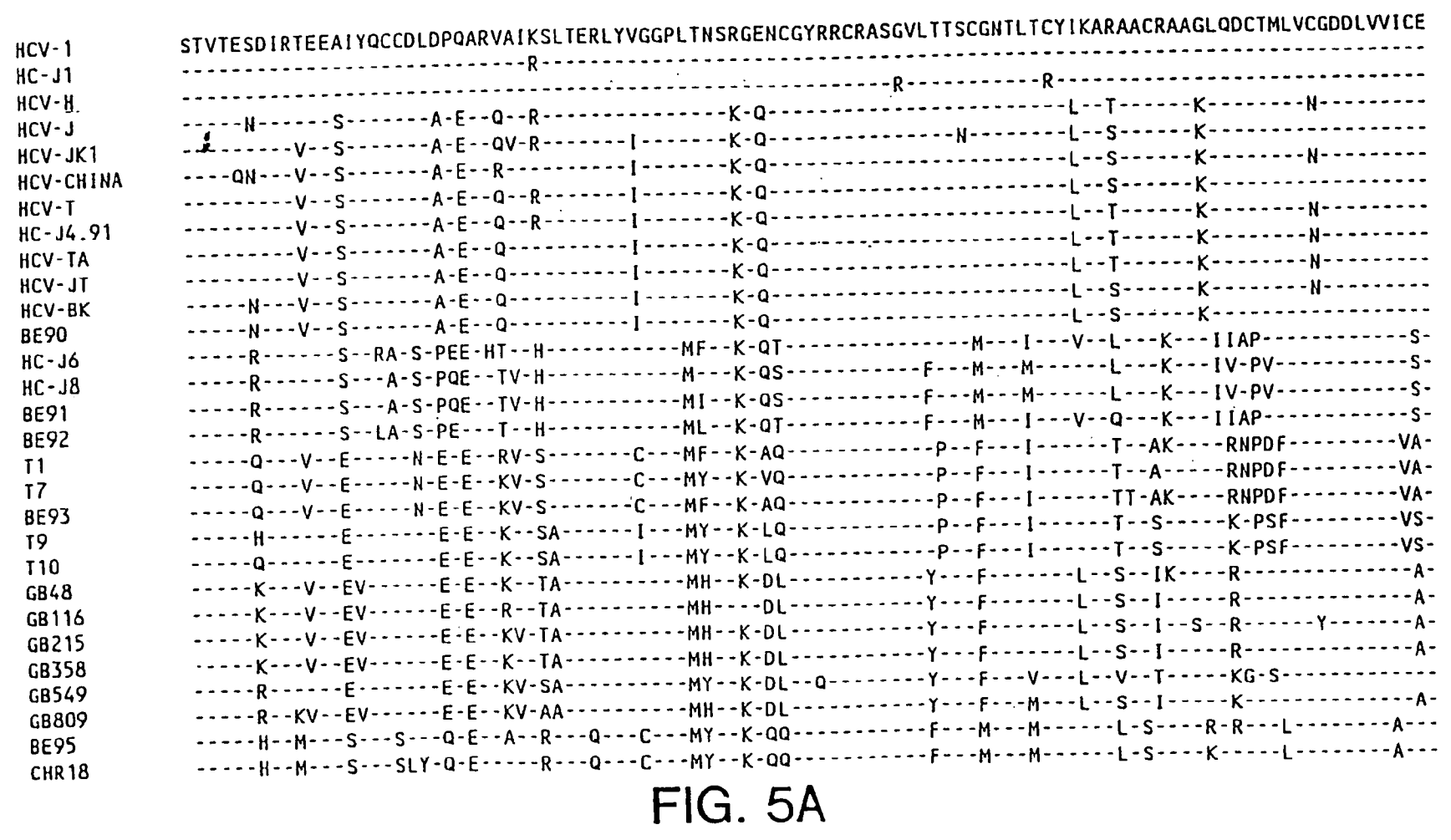

Isolates BE82, BE90, BE91, BE92, BE93, BE94, BE95, BE96, BE97, BE98, obtained from Belgium; GB48, GB116, GB358, GB569, GB549, GB809, GB487, GB724, and GB438, obtained from Gabon; CAM600 and CAM736, obtained from Cameroun; were retained for further study because aberrant reactivities were observed after genotyping by means of a LiPA including probes 5 to 27 according to examples 3 and 4. The sequences of the 5' untranslated region were obtained after nested PCR by means of primers with SEQ ID NO. 1, 2, 3 and 4, cloning, and sequencing as described in example 2. Sequence information was obtained in the NS5 coding region for most of these isolates, and an alignment with known sequences is presented in FIG. 5. The homologies of NS5 nucleic acid and amino acid sequences of representative isolates for each subtype with the sequences of published isolates is presented in Table 6. This calculation allows classification into types and subtypes, as presented in FIG. 4. Nucleotide sequence alignment of the 5' untranslated regions of these new isolates with some prototype sequences is also presented in FIG. 4. Several mutations can be observed compared to the HCV-1 sequence. As identical mutations in the 5' untranslated region correlate with similar sequences in the coding region, such mutations are employed in the present invention to design new type and subtype-specific probes.

BE82, a subtype 1b isolate, showed a C mutation at position −94, and therefore could not react with probe 7. After sequencing of the NS5 region, it could be concluded that this isolate belonged to subtype 1b. Therefore, probe 30, including a degeneration of T and C at position −94, should enable better genotyping of subtype 1b.

BE90, another subtype 1b isolate, showed a T mutation at position −159 and a G mutation at position −126, and therefore only reacted with the universal probes 20 and 27 and the subtyping probe 7. Sequencing of the NS5 region taught that the isolate belonged to subtype 1b. Probe 28, including a degeneration of T and C at position −126 should enable better genotyping of types 1 and 6.

Isolate BE92 reacted only with probes 8 and 26 in addition to the universal probes 20 and 27. Thus, this isolate could be classified as type 2, but could not be subtyped because no reactivity with probes 23, 24, 25, or 26 could be observed. After sequencing, two new motifs could indeed be observed: GGACCCAGTCTTCCTG, covered by probe 33, and TGC-CTGGTCATTTGGG, covered by probe 34. Sequencing of the NS5 region indeed revealed homologies with type 2a and 2b isolates compatible with classification within the same type, but in another subtype which is the proposed subtype 2c.

Isolates BE93 and BE94 did not show any reactivity with the subtyping probe 14. After sequencing the 5' untranslated region and the NS5 region, it was concluded that these isolates belonged to the 3a subtype. Therefore, a probe containing a C and A degeneration at position −118 like probe 35, should allow better genotyping of subtype 3a.

Isolates GB48, GB116, GB358, and GB569 showed positive hybridization signals on probe 17 and 19 in LiPA, indicating similarity to the previously reported type 4 isolates, but isolates GB549 and GB809 only reacted with the universal probes. The sequences of parts of the 5' untranslated region and NS5 were obtained. From FIGS. 5 and 6 and Table 6, it can be concluded that the isolates represented by GB358 belong to the same subtype of type 4, which is the proposed subtype 4a. However, both GB549 and GB809 show lower homologies to the subtype 4a, 4b and 4d isolates, and also to each other, but GB809 seems to belong to the same subtype as Z4. These homologies are compatible with classification into the same type 4, but into a different subtype of type 4: subtype 4e for GB549 and subtype 4c for GB809 are proposed. Sequences obtained from isolates GB116, GB358, and GB569 all showed the motifs AATCGCCGGGATGACC, detectable with probe 38 and TTTCCGGGCATTGAGC, detectable with probe 19. Thus, probes 38 and 19 are useful for detection and classification of subtype 4a. Probe 38 is specific for subtype 4a, 4b, 4d, 4f and 3b, while probe 19 recognizes subtypes 3b, 4a and 4d, but also hybridizes to the new types 3c and 4f. Interestingly, the new subtype 3b sequence HCV-TR should cross-react with these probes. However, 3b can still be classified as type 3 because of the reactivity with the type 3-specific probe 21.

GB549 also shows characteristic motifs. Motif AATCGC-CGGGACGACC can be detected by probe 40 and the sequence AATGCCCGGCAATTTG is detectable with probe 41. Thus, probes 40 and 41 are useful for subtyping of subtype 4b.

Reactivities identical to GB809 were obtained on LiPA with two samples obtained from Cameroun: CAM600 and CAM736. After sequencing the NS5 region, it could be concluded that these samples belong to the same subtype as GB809, and after sequencing the 5' untranslated region, two identical motifs were again detected as those already present in GB809. Thus, it appears that the motif AATCGC-CGAGATGACC, detectable with probe 42, and AAT-GCTCGGAAATTTG, detectable with probe 43, are characteristic for subtype 4c, and that probes 42 and 43 are useful for detection and classification of subtype 4c. However Z4, which shows homology in the E1 region compatible with classification into the same subtype 4c, shows 511R sequences which are again unique and may be detected by probes 7, 50 and 53.

New sequences were detected in the 5' untranslated region of isolates GB487, GB724 and BE97. A new subtype classification, not based on sequence information of the coding region, is tentatively proposed for these isolates. All three isolates show the sequence TGCCTGGAAATTTGGG, detectable with probe 50. GB487 shows the unique sequence AATCGCCAGGATGACC, detectable with probe 49, and is tentatively classified as subtype 4h. GB724 and BE97 both contain the sequence GGAATCGCCAGGACGA, detectable with probe 53, and are tentatively classified as subtype 4g.

Type 4 isolates usually show a T at position −238 and a A at −235. Therefore, probes 37, 38, and 51 should enable better genotyping of type 4.

In another example, BE95, which only hybridized to probes 7 and 17 in the LiPA shows low homologies in the coding region of about 68% with all other isolates, except BE96 which shows an homology to BE95 compatible with classification into the same subtype, which is the proposed subtype 5a. BE95, BE96, and SA1 all show the same motifs GAGTGTCGAACAGCCT, detected with probe 44; AAT-TGCCAGGAYGACC, detectable with probes 45 and 47; and TCTCCGGGCATTGAGC, detectable with probe 46. Thus, probes 44, 45, 46 and 47 are useful for genotyping of type 5a.

Sequences have been published by Bukh et al. (1992), which contain a unique CA insertion between positions −144 and −145. These isolates are tentatively classified as type 6 and can be detected by means of probe 48.

A new type of hepatitis C virus was discovered in isolate BE98, which only reacted with probe 19 on LiPA. The sequence of the 5' untranslated region contains the new motif GAATCGCCGGGTTGAC that can be detected by means of probe 54. Sequencing of the core region revealed sequences showing about equally distant homologies to genotypes 3a and 3b, and a new type 3c is proposed for this prototype sequence.

Isolate GB438 contains sequence motifs which are typical for subtype 4a, detectable with probes 38 and 19, but still shows a different sequence in the E1 region, representing a new subtype within type 4, which was designated subtype 4f. Discrimination from subtype 4a may be performed by means of probes with SEQ ID NO 51 and 7.

Probes 29, derived from the sequence of BE90, and probes 51 and 52, derived from the sequence of GB724, may be useful to improve genotyping of certain HCV types or subtypes.

Example 9

Calculation of Nucleotide Distances

Phylogenetic Analysis.

Previously published sequences were taken from the EMBL database, release 35. Other sequences were analysed by the inventors and have been deposited in the DDBJ database. Sequences were presented in a sequential format to the Phylogeny Inference Package Version 3.5c (Felsenstein, March 1993). Only sequences with identical lengths were included in the similarity calculations. The programs employed were DNADIST, PROTDIST, DNAPARS, PROTPARS, NEIGHBOR, SEQBOOT, CONSENSE and DRAWTREE. DNA maximum likelihood distance matrices were produced by DNADIST using the Kimura 2-parameter setting. A bootstrapping analysis was run using SEQBOOT, with 2000 repetitions. All these matrices were further analyzed in NEIGHBOR, using the Neighbor-Joining settings and in CONSENSE to calculate the consensus tree. The SEQBOOT dataset was also analyzed in the DNAPARS program on 1130 repetitions. Deduced protein sequences were analyzed in PROTDIST followed by NEIGHBOR. Finally, the program DRAWTREE was used to create a' graphic output of the phylogenetic tree. All analyses were done on a SUN SPARC IPX computer station.

The NS5 Region.

By using the primer set described by Enomoto et al. (1990), we amplified, cloned and sequenced 340 by long NS5b PCR fragments from 13 different isolates. The nucleotide sequences were used to create a phylogenetic tree using the DNADIST program of the PHYLIP 3.5c package (Felsentstein, 1993). A diversity of 6 major groups or 'types' is evident for this unrooted tree. Each group could be further subdivided into two ore more subgroups or 'subtypes'. The following clusters (groups consisting of closely related isolates) were created: 1a, 1b, 2b, 3a, 3b, 4a and 5a. This clustering appeared in 100% of the bootstrap resampled data sets using the programs SEQBOOT/DNADIST/NEIGHBOR/CONSENSE on 2000 repetitions. The bootstrapped DNAPARS analysis yielded a similar clustering. From the DNADIST matrix, the molecular evolution distances between isolates, subtypes and types could be calculated. Only the above indicated separated clusters were included in these calculations. Between isolates in one subtype, this distance ranged from 0.0148 to 0.1064 (mean 0.0623; SD 0.0181). The distance between subtypes ranged from 0.1654 to 0.2675 (mean 0.2312; SD 0.0182) and that between types from 0.3581 to 0.6549 (mean 0.4942; SD 0.0485). However, some exceptional cases appeared.

The distance between HC-J6 and isolate BE92 was 0.1539, a low value for distances between distances, but far above any value obtained between isolates belonging to the same subtype. NS5 nucleotide sequence homology between HC-J6 and BE92 was 86.2%. The bootstrapped DNA datasets clustered both sequences in 98.8% of the cases, which is an argumentation for a subtype 2a classification, but the molecular evolutionary distance and the sequence of the 5' UR of BE92 allowed us to tentatively classify this isolate as subtype 2c. GB809 could be positioned at a mean distance of 0.1509 (min./max.=0.1384/0.1597) from the type 4a cluster. A maximum homology of 87.4% exists between GB809 and GB358 (type 4a). However, these data, together with the observed variations in the 5'UR allowed us to create a new type 4 subtype, 4c. GB549 represents the new subtype 4e and has distances of 0.2426 from cluster 4a; 0.2403 from subtype 4c and 0.1738 from GB438 at the nucleotide level. Isolate GB438 possibly represents another new type 4 subtype, tentatively designated 4f.

The Core/E1 Region.

Calculation of the phylogenetic tree for the core/E1 region between nucleotides 378 and 957 using the DNASDIST program resulted in the recognition of six major branches, representing the 6 different genotypes. The following clusters could be delineated with a 100% certainty from the bootstrap resampling analysis on 2000 repetitions: subtype 1a, 1b, 2a, 2b, 3a and 4a. The clustering is irrelevant for subtype 4c, 4e, 4f and 5a because they are only represented by one isolate. Based on the DNADIST matrix, the molecular evolutionary distance for isolates belonging to the same subtype ranged from 0.0402 to 0.111 (mean 0.0772, SD 0.0197), between subtypes from 0.1864 to 0.3535 (mean 0.2833, SD 0.0350) and between types from 0.3824 to 0.6230 (mean 0.4894, SD 0.0554).

The distances from the DNADIST matrix provided further evidence for the existence of at least 4 different subtypes in type 4. Type 4a has a mean mutual distance of 0.0083; while the mean with type 4c, 4e and 4f was 0.2602. Subtype 4c and 4f were separated from 4e by respectively, 0.2047 and 0.1864, while the distance between 4c and 4f was 0.2316.

The NS3/4 Region.

DNA sequences containing the previously described type 3a epitope region (Stuyver et al., 1993a) and other sequences of the EMBL databank were used to calculate the nucleotide distances using DNADIST and NEIGHBOR. From the DNADIST matrix, the molecular evolutionary distances between isolates ranged from 0.0407 to 0.1181 (mean 0.0855, SD 0.0190), between subtypes from 0.2281 to 0.2603 (mean 0.2416, SD 0.0098) and between types from 0.4052 to 0.6247 (mean 0.4889, SD 0.0531).

Example 10

As described in the introduction to the examples and in previous examples, variable regions in the 5'UR are expected to contain genotype-specific sequences also in newly discovered genotypes, as examplified in example 8, and consequently, such new genotype-specific motifs should again be detectable by means of the genotype-specific probes as described in example 8. Therefore, probes 32, and as described in example 8, probes 31, 33, 34, 37, 38, 44, 45, and 46 were synthesized and applied to nitrocellulose membranes and line probe assays with biotin-labelled PCR fragments was performed as described in example 3 and 4, except for the labelling of the PCR product with biotin which was not incorporated from bio-11-dUTP, but from of 5'-biotinylated primers with SEQ ID NO 3 and 4 or 5'-biotinylated primers with SEQ ID NO 1 and 2, during the synthesis of the PCR fragment.

Figure 6:
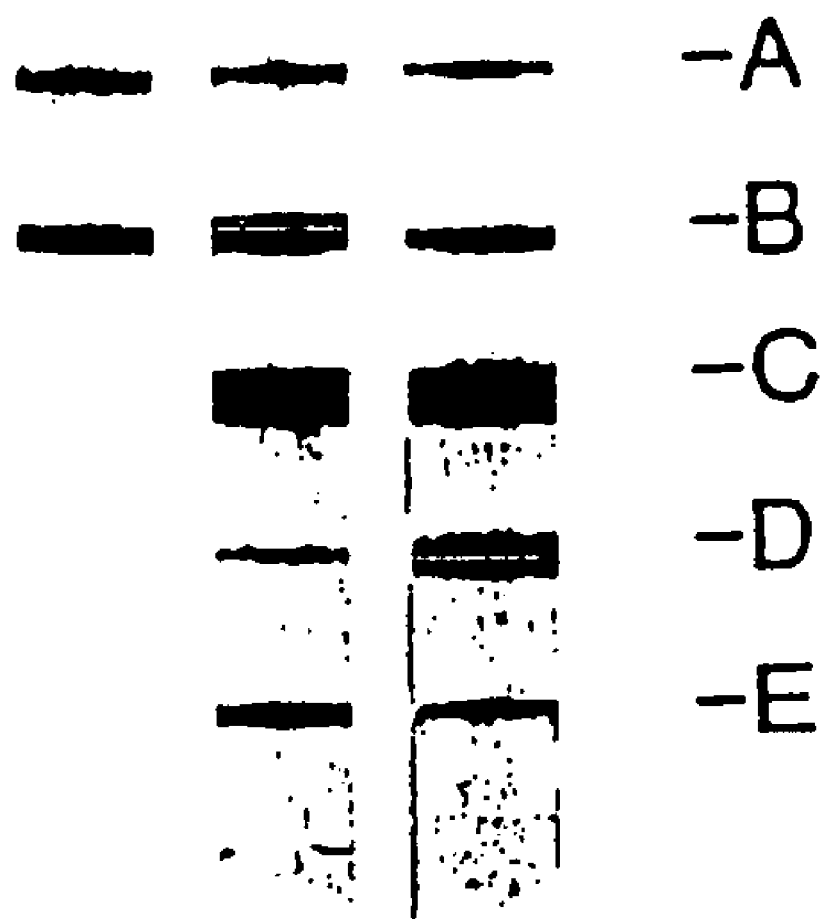

FIG. 6 shows the type-specific hybridization of HCV type 2, but not type 1, 5'UR fragments to the probe with SEQ ID NO 32. Both subtype 2a and 2b isolates hybridized specifically to probe 32.

Figure 7:
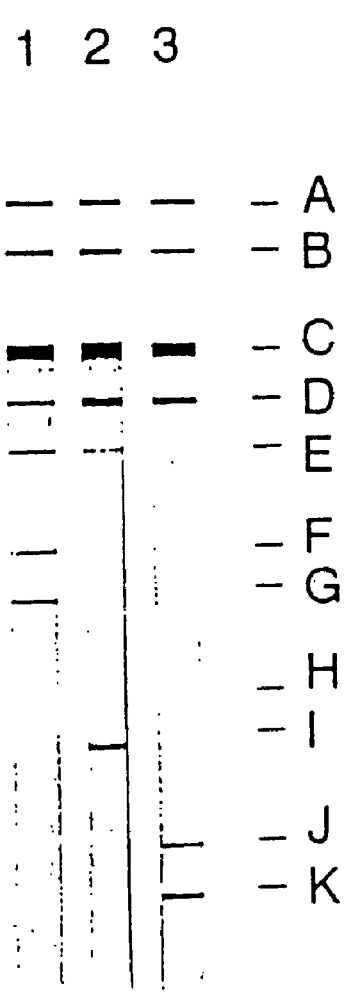

In FIG. 7, the probes with SEQ ID NO 33 and 34 could be shown to hybridize specifically to the genotype 2c PCR product derived from serum BE92, while genotype 2a and 2b sera did not react to these probes although a specific hybridization with the respective 2a and 2b genotype-specific probes could be observed. It is to be understood that the new genotype 2c may differ from other genotype 2c subtypes discovered recently, and therefore, the alternative names may be proposed for denomination of this subtype.

Figure 8:
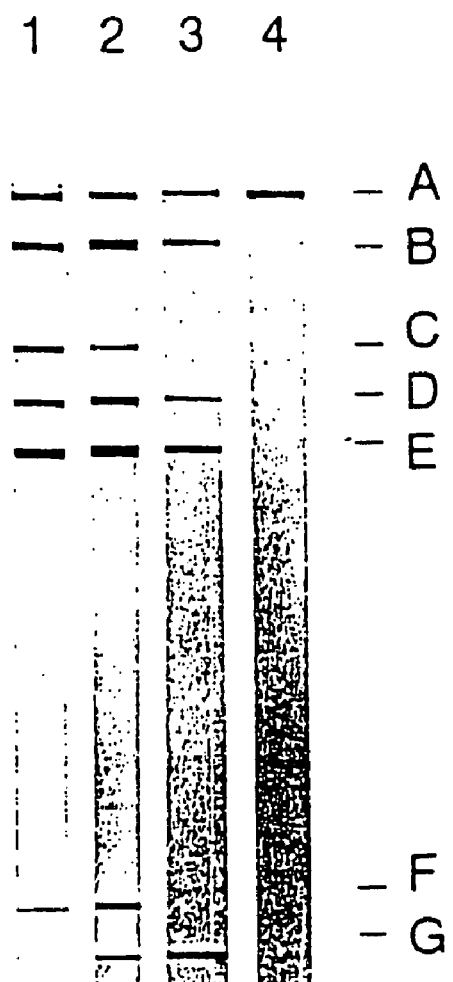

FIG. 8 shows line probe assays performed with type 4 sera to show specific hybridization of the most common type 4 sera to probes 37 and 38.

Figures 9, 10:

FIG. 9 depicts specific hybridization of type 5a sera to probes 44, 45, 46, and probe 7, while reactivity of type 4 sera is usually confined to probe 31 and absent on probes 44 to 46. Therefore, the promiscuity of the probe with SEQ ID NO 18 for both type 4 and type 5 isolates, can now conveniently be overcome by employing, in addition to the probe with SEQ ID NO 19, probes with SEQ ID NO 37, 38, 44, 45, 46, 7, 30, and 31 for discrimination of genotypes 4 and 5.

Example 11

It may be preferable to use other hybridization conditions (temperature, buffers) as those outlined in examples 3 and 4. Therefore, probes with SEQ ID NO 93, 94, 95, and 96 were applied to nitrocellulose membranes. FIG. 10 shows line probe assays with the type 4a serum GB116 and the type 5a serum BE95, as described in example 4, except for the following: After denaturation of the PCR fragment in NaOH/SDS, 1.0 ml hybridization solution (prewarmed at 50° C.) consisting of 3×SSC (Maniatis et al., (1982) and 1% sodium dodecyl sulphate (SDS), was added to the denatured PCR product and hybridization was performed in a shaking water bath at 50° C. for 2 hours. The strips were washed with the same hybridization solution at 50° C. for 30 min, after which the strips were washed and color development was performed as described in example 4. In FIG. 10, a clear type-specific reaction can be observed. Therefore, type-specific hybridization has been obtained in other hybridization conditions as described in examples 4 and 10 after having introduced minor modifications to the hybridization probes. For example, the position of the probes can be changed in order to achieve more specific hybridization in a certain hybridization condition, for example, the probe can be positioned in such a way that the type-specific nucleotides are located in the middle part of the probe. For certain probes to retain specificity in other hybridization conditions, it may also be preferable to elongate or shorten the contiguous HCV sequence and/or to reverse the sense of the probes to allow genotype-specific hybridization at a certain preferred temperature or salt concentration. However, in some cases, it may be preferable to include inosines or mismatching nucleotides to allow genotype-specific hybridization at a certain preferred temperature or salt concentration. For example, the probe with SEQ ID NO 37, which was able to discriminate between type 4 and 5 isolates in tertramethylammoniumchloride buffer as described in example 10, was now changed into probe with SEQ ID NO 93 (5'-GAGTGTTGTACAGCCTCC-3') by elongation of the contiguous HCV sequence at the 3' end with 2 nucleotides, and probe 93 showed a specific reactivity in SSC/SDS hybridization buffer (FIG. 10). The probe with SEQ ID NO 44, which was able to discriminate between type 4 and 5 isolates in tertramethylammoniumchloride buffer as described in example 10, was now changed into probe with SEQ ID NO 96 (5'-GAGTGTC-GAACAGCCTC-3') by elongation of the contiguous HCV sequence at the 3' end with 1 nucleotide, and probe 96 showed a specific reactivity in SSC/SDS hybridization buffer (FIG. 10). The antisense probe with SEQ ID NO 46, which targets positions −132 to −117 was able to discriminate between type 4 and 5 isolates in tertramethylammoniumchloride buffer as described in example 10, was now changed into probe with SEQ IS NO 95 (5'-TGCCCGGAGATTTGGG-3'), a sense probe which targets positions −126 to −111, and probe 95 showed a specific reactivity in SSC/SDS hybridization buffer (FIG. 10).

This example illustrates the numerous possibilities of developing probes to those skilled in the art for targeting the genotype-specific mutations as presented in FIG. 4, or for targeting the genotype-specific mutations that are present in other new or still to be discovered genotypes.

TABLE 1

|  | 1a | 1b | 2a | 2b | 2c | 3a | 3b | 3c | 4a |
|---|---|---|---|---|---|---|---|---|---|
| Cha et al. | I | I | II | III | — | IV | — | — | — |
| Naka o et al. | Pt | K1 | K2a | K2b | — | K3 | — | — | — |
| Chan et al. | 1 | 1 | 2 | 2 | — | 3 | — | — | 4 |
| Mori et al. | I | II | III | IV | — | V | VI | — | — |
| Oka moto et al. | I | II | III | IV | — | V | VI | — | — |
| Proto type isolate | HCV-1 | HCV-J | HC-J6 | HC-J8 | BE92 | BR56 | HCV-TR | BE98 | GB358 |
| Isolates of the present invention | — | BE90 BE82 | — | BE91 | BE92 | BR56 BE93 BE94 | — | BE98 | GB48 GB116 GB569 GB215 |

|  | 4b | 4c | 4d | 4e | 4f | 4g* | 4h* | 5a | 6a | 6? |
|---|---|---|---|---|---|---|---|---|---|---|
| Cha et al. | — | — | — | — | — | — | — | V | — |  |
| Naka o et al. | — | — | — | — | — | — | — | — | — |  |
| Chan et al. | — | — | — | — | — | — | — | 5 | 6 |  |
| Mori et al. | — | — | — | — | — | — | — | — | — |  |
| Oka moto et al. | — | — | — | — | — | — | — | — | — |  |
| Proto type isolate | Z1 | GB809 Z4 | DK13 | GB549 | GB438 | BE97 | GB487 | SA1 | HK1 | HK2 |
| Isolates of the present invention | — | GB809 CAM600 CAM736 | — | GB549 | GB438 | GB724 BE97 | GB487 | BE95 BE96 | — | HK2 |

TABLE 2

Interpretation of the results shown in FIG. 3

| Type | Probe | BR5 | BR12 | BR18 | BR22 | BR19 | BE95 | BU79 | BR23 | JP63 |
|---|---|---|---|---|---|---|---|---|---|---|
| 1 | 5 | + | + | − | − | − | − | − | + | + |
| 1 | 6 | + | + | − | − | − | − | − | + | + |
| 1b | 7 | − | + | − | − | − | + | + | + | + |
| 2 | 8 | − | − | + | − | − | − | − | − | + |
| 2 | 26 | − | − | + | − | − | − | − | − | + |
| 2a | 22/24 | − | − | + | − | − | − | − | − | + |
| 2a | 10 | − | − | + | − | − | − | − | − | + |
| 3 | 13 | − | − | − | + | + | − | − | + | − |
| 3 | 14 | − | − | − | + | + | − | − | + | − |
| 3 | 21 | − | − | − | + | + | − | − | + | − |
| 3a | 15 | − | − | − | + | − | − | − | + | + |
| 3b | 16 | − | − | − | − | + | − | − | − | − |
| 4 | 17 | − | − | − | − | − | + | − | − | − |
| 4 | 19 | − | − | − | − | − | + | + | − | − |
| 4 | 18 | − | − | − | − | − | − | − | − | − |
| Universal | 155 | + | + | + | + | + | + | + | + | + |
|  | 27 | + | + | + | + | + | + | + | + | + |
|  | 20 | + | + | + | + | + | + | + | + | + |
| Conjugate Control |  | + | + | + | + | + | + | + | + | + |
| RESULT |  | 1a | 1b | 2a | 3a | 3b | 4 | 4 | 1b + 3a | 1b + 2a |

TABLE 3

Final results of HCV LIPA typing and HCV antibody assays

| Isolate | NS4 | NS5 | Core | LIA | EIA | type |
|---|---|---|---|---|---|---|
| BR1 | 3 | 3 | 3 | 1 |  | 1a |
| BR2 | 3 | 1 | 2 | 1 |  | 1a |
| BR3 | 0 | 0 | 0 | 0 |  | 1a |
| BR4 | 1 | 0 | 0 | 9 |  | 1a |
| BR5 | 3 | 3 | 2 | 1 |  | 1a |
| BR6 | 3 | 3 | 2 | 1 |  | 1a |
| BR7 | 9 | 0 | 1 | 1 |  | 1a |
| BR8 | 0 | 9 | 1 | 9 |  | 1a |
| BR9 | 0 | 0 | 0 | 0 |  | 1b |
| BR10 | 0 | 0 | 0 | 0 |  | 1b |
| BR11 | 3 | 0 | 3 | 1 |  | 1b |
| BR12 | 1 | 1 | 0 | 1 |  | 1b |
| BR13 | 1 | 0 | 0 | 9 |  | 1b |
| BR14 | 1 | 0 | 0 | 9 |  | 1b |
| BR15 | 0 | 0 | 1 | 1 |  | 1b |
| BR16 | 1 | 0 | 0 | 9 |  | 1b |
| BR17 | 1 | 0 | 0 | 9 |  | 1b |
| BR18 | 0 | 0 | 3 | 1 |  | 2a |
| BR19 | 3 | 3 | 2 | 1 |  | 3b |
| BR20 | 9 | 0 | 1 | 9 |  | 3a |
| BR21 | 2 | 3 | 2 | 1 |  | 3a |
| BR22 | 0 | 0 | 0 | 0 |  | 3a |
| BR23 | 3 | 3 | 3 | 1 |  | 1b + 3a |
| BR24 | 2 | 2 | 2 | 1 | 6.7 | 1a |
| BR25 | 3 | 2 | 3 | 1 | 6.9 | 1a |
| BR26 | 1 | 2 | 3 | 1 | 6.4 | 1a |
| BR27 | 9 | 0 | 2 | 1 | 7.1 | 1b |
| BR28 | 2 | 3 | 2 | 1 | 6.9 | 1b |
| BR29 | 3 | 3 | 9 | 1 | 6.1 | 1b |
| BR30 | 3 | 3 | 2 | 1 | 6.6 | 1b |
| BR31 | 1 | 0 | 2 | 1 | 6.8 | 1b |
| BR32 | 2 | 3 | 2 | 1 | 6.8 | 1b |
| BR33 | 0 | 2 | 0 | 1 | 1.1 | 3b |
| BR34 | 1 | 3 | 3 | 1 | 6.6 | 3a |
| BR35 | 9 | 1 | 1 | 1 | 5.2 | 3a |
| BR36 | 2 | 0 | 2 | 1 | 6.2 | 3a |
| BR37 | 1 | 0 | 3 | 1 | 6.8 | 1b + 3a |
| BR38 | 1 | 3 | 0 | 1 | 7.1 | 1a |
| BR39 | 9 | 0 | 1 | 9 | 2.9 | 1a |
| BR40 | 0 | 0 | 2 | 1 | 0.9 | 1a |
| BR41 | 0 | 0 | 3 | 1 | 0.3 | 1a |
| BR42 | 0 | 0 | 1 | 9 | 6.0 | 1a |
| BR43 | 0 | 0 | 2 | 1 | 4.7 | 1a |
| BR44 | 0 | 0 | 2 | 1 | 6.7 | 1a |
| BR45 | 0 | 0 | 1 | 1 | 4.7 | 1a |
| BR46 | 0 | 0 | 9 | 9 | 2.2 | 1a |
| BR47 | 3 | 3 | 2 | 1 | 0.5 | 1b |
| BR48 | 0 | 1 | 2 | 1 | 0.2 | 1b |
| BR49 | 0 | 1 | 1 | 1 | 5.4 | 1b |
| BR50 | 1 | 0 | 1 | 1 | 7.4 | 1b |
| BR51 | 0 | 0 | 3 | 1 | 7.4 | 1b |
| BR52 | 2 | 3 | 2 | 1 | 4.7 | 1b |
| BR53 | 0 | 0 | 1 | 1 | 7.9 | 1b |
| BR54 | 2 | 3 | 2 | 1 |  | 1b |
| BR55 | 0 | 9 | 1 | 9 | 1.4 | 3b |
| BR56 | 2 | 1 | 2 | 1 | 2.9 | 3a |
| BR57 | 1 | 3 | 2 | 1 | 1.5 | 3a |
| BR58 | 1 | 1 | 2 | 1 | 7.3 | 3a |
| BR59 | 0 | 1 | 0 | 9 | 0.4 | 3a |
| BR60 | 0 | 3 | 1 | 1 | 1.6 | 3a |
| BR61 | 0 | 0 | 3 | 1 | 2.6 | 3a |
| JP62 | 1 | 2 | 2 | 1 |  | 2a |
| JP63 | 3 | 3 | 2 | 1 |  | 1b + 2a |
| BE64 | 3 | 3 | 3 | 1 |  | 1b |
| BE65 | 0 | 0 | 3 | 1 |  | 1b |
| BE66 | 1 | 0 | 2 | 1 |  | 1b |
| BE67 | 3 | 3 | 2 | 1 |  | 1b |
| BE68 | 2 | 1 | 3 | 1 |  | 2a |
| BE69 | 0 | 0 | 0 | 0 |  | 3a |
| NE70 | 3 | 1 | 3 | 1 |  | 1a |
| NE71 | 9 | 9 | 1 | 1 |  | 3a |
| NE72 | 0 | 0 | 1 | 9 |  | 3a |
| NE73 | 0 | 0 | 0 | 0 |  | 3a |
| BU74 | 0 | 0 | 1 | 1 |  | 4 |
| BU75 | 0 | 0 | 1 | 1 |  | 4 |
| BU76 | 0 | 0 | 1 | 1 |  | 4 |
| BU77 | 0 | 0 | 2 | 1 |  | 4 |
| BU78 | 0 | 0 | 1 | 1 |  | 4 |
| BU79 | 0 | 1 | 0 | 9 |  | 4 |
| GB80 | 0 | 0 | 0 | 0 | 0.4 | 4 |
| GB81 | 0 | 0 | 0 | 0 | 3.4 | 2a + 4 |

TABLE 4

Nucleotide sequence, position and orientation of the primers and probes.

| SEQ ID NO. | Type | Name | Position | Polarity | Sequence from 5' to 3' (1) | Reference |
|---|---|---|---|---|---|---|
| 1 | Universal | HcPr98 | −299 | + | CCCTGTGAGGAACTWCTGTCTTCACGC | Kato et al., 1992 |
| 2 | Universal | HcPr29 | −1 | − | GGTGCACGGTCTACGAGACCT | Okamoto et al., 1991 |
| 3 | Universal | HcPr92 | −264 | + | TCTAGCCATGGCGTTAGTRYGAGTGT | Present invention |
| 4 | Universal | HcPr96 | −29 | − | CACTCGCAAGCACCCTATCAGGCAGT | |
| 5 | 1 | HcPr124 | −170 | + | AATTGCCAGGACGACC | Kato et al., 1990 |
| 6 | 1 | HcPr125 | −117 | − | TCTCCAGGCATTGAGC | Kato et al., 1990 |
| 7 | 1b | HcPr138 | −103 | + | CCGCGAGACTGCTAGC | Kato et al., 1990 |
| 8 | 2 | HcPr147 | −83 | + | TAGCGTTGGGTTGCGA | Nakao et al., 1991 |
| 26 | 2 | HcPr160 | −126 | − | ATAGAGTGGGTTTATC | Okamoto et al., 1991 |
| 9 | 2a | HcPr136 | −168 | + | TTRCCGGRAAGACTGG | Chan et al., 1992 |
| 10 | 2a | HcPr137 | −117 | − | TGRCCGGGCATAGAGT | Chan et al., 1992 |
| 22 | 2a | HcPr156 | −165 | + | CCGGGAAGACTGGGTC | Okamoto et al., 1991 |
| 24 | 2a | HcPr158 | −136 | + | ACCCACTCTATGCCCG | Okamoto et al., 1991 |
| 11 | 2b | HcPr126 | −168 | + | TTACCGGAAGACTGG | Nakao et al., 1991 |
| 12 | 2b | HcPr127 | −117 | − | TGACCGGACATAGAGT | Nakao et al., 1991 |
| 23 | 2b | HcPr157 | −165 | + | CCGGAAAGACTGGGTC | Okamoto et al., 1992 |
| 25 | 2b | HcPr159 | −136 | + | ACCCACTCTATGTCCG | Okamoto et al., 1992 |
| 13 | 3 | HcPr128 | −170 | + | AATCGCTGGGGTGACC | Present invention |
| 14 | 3 | HcPr129 | −117 | − | TTTCTGGGTATTGAGC | Present invention |
| 21 | 3 | HcPr154 | −103 | + | CCGCGAGATCACTAGC | Present invention |
| 15 | 3a | HcPr140 | −146 | + | TCTTGGAGCAACCCGC | Chan et al., 1992 |
| 16 | 3b | HcPr139 | −146 | + | TCTTGGAACAACCCGC | Chan et al., 1992 |
| 17 | 4 | HcPr144 | −170 | + | AATYCCGGGATGACC | Bukh et al., 1992 |
| 18 | 4 | HcPr145 | −147 | + | TTCTTGGAACTAACCC | Present invention |
| 19 | 4 | HcPr146 | −117 | − | TTTCCGGGCATTGAGC | Present invention |
| 20 | Universal | HcPr142 | −115 | + | TTGGGCGYGCCCCCGC | Kato et al., 1990 |
| 27 | Universal | HcPr153 | −195 | + | TCTGCGGAACCGGTGA | Kato et al., 1990 |

TABLE 5

| Type | Sequence 5' to 3' | SEQ ID NO |
|---|---|---|
| 1 | AATTGCCAGGACGACC | 5 |
| 1*/6 | TCTCCAGGCATTGAGC | 6 |
| 1/6 | AATTGCCAGGAYGACC | 28 |
| 1a/2 | CCCCGCAAGACTGCTA | 31 |
| 1b | GCTCAGTGCCTGGAGA | 29 |
| 1b/3c/5 | CCGCGAGACYGCTAGC | 30 |
| 2/6 | CGTACAGCCTCCAGGC | 32 |
| 2a | CCGGGAAGACTGGGTC | 22 |
| 2a | ACCCACTCTATGCCCG | 24 |
| 2b | ACCCACTCTATGTCCG | 25 |
| 2c | GGACCCAGTCTTCCTG | 33 |
| 2c | TGCCTGGTCATTTGGG | 34 |
| 3a* | CCGCAAGATCACTAGC | 36 |
| 3a | TKTCTGGGTATTGAGC | 35 |
| 3c | GAATCGCCGGGTTGAC | 54 |
| 4/5 | AATYCCGGGATGACC | 17 |
| 4a/4b/4c/4d/4g/4h | GAGTGTTGTACAGCCT | 37 |
| 4e | GAGTGTTGTGCAGCCT | 39 |
| 3b/4a/4b/4d/4f | AATCGCCGGGATGACC | 38 |
| 3b/4a/4d/3c/4f | TTTCCGGGCATTGAGC | 19 |
| 4e | AATCGCCGGGACGACC | 40 |
| 4e | AATGCCCGGCAATTTG | 41 |
| 4c* | AATCGCCGAGATGACC | 42 |
| 4c | AATGCTCGGAAATTTG | 43 |
| 4h | AATCGCCAGGATGACC | 49 |
| 4h/4g | TGCCTGGAAATTTGGG | 50 |
| 4g | GGAATCGCCAGGACGA | 53 |
| 4f/4e | AGTYCACCGGAATCGC | 52 |
| 4f/4g/6/2a/2b/2c | GAGTGTCGTACAGCCT | 51 |
| 5a/5 | GAGTGTCGAACAGCCT | 44 |
| 5a* | AATTGCCGGGATGACC | 45 |
| 5a/5 | AATTGCCGGGACGACC | 47 |
| 5a* | TCTCCGGGCATTGAGC | 46 |
| 6a/6 | GGGTCCTTTCCATTGG | 48 |

TABLE 6

| | Homology to the NS5 nucleotide (amino acid) sequence of type | | | | |
|---|---|---|---|---|---|
| HCV isolates | 1a<br>HCV-1 | 1b<br>BE90 | 2a<br>HC-J6 | 2b<br>BE91 | 2c<br>BE92 |
| HCV-1-1 | 100 (100) | 81.5 (87.5) | 67.4 (71.9) | 67.1 (72.6) | 65.9 (72.6) |
| HC-J1-2 | 97.1 (99.1) | 80.3 (86.7) | 66.8 (71.9) | 67.4 (72.6) | 65.6 (72.6) |
| HCV-H-3 | 97.1 (98.2) | 80.6 (85.8) | 66.8 (69.9) | 66.7 (70.8) | 66.8 (70.8) |
| HCV-J-4 | 80.9 (87.6) | 89.7 (93.8) | 67.6 (74.3) | 67.1 (73.5) | 67.7 (73.5) |
| HCV-JK1-5 | 81.8 (85.8) | 92.9 (96.5) | 67.7 (70.8) | 69.1 (71.7) | 68.2 (69.9) |
| HCV-CHINA-6 | 79.1 (85.8) | 94.1 (97.4) | 65.3 (70.8) | 66.5 (69.9) | 65.9 (69.9) |
| HCV-T-7 | 81.5 (87.6) | 94.1 (98.2) | 67.1 (72.6) | 68.2 (71.7) | 67.4 (71.7) |
| HC-J4.91-8 | 80.0 (86.7) | 91.2 (94.7) | 67.4 (72.6) | 67.9 (71.7) | 67.7 (71.7) |
| HCV-TA-9 | 82.7 (87.6) | 91.5 (97.4) | 67.9 (71.7) | 67.9 (70.8) | 67.4 (70.8) |
| HCV-JT-10 | 82.7 (87.6) | 91.5 (97.4) | 67.9 (71.7) | 67.9 (70.8) | 67.4 (70.8) |
| HCV-BK-11 | 82.4 (86.7) | 94.4 (99.1) | 66.5 (71.7) | 66.5 (70.8) | 67.4 (70.8) |
| BE90 | 81.5 (87.6) | 100 (100) | 66.2 (72.6) | 67.1 (71.7) | 66.8 (71.7) |
| HC-J6-16 | 67.4 (71.7) | 66.2 (72.6) | 100 (100) | 80.6 (88.5) | 86.2 (94.7) |
| HC-J8-17 | 64.6 (71.5) | 66.5 (72.6) | 80.6 (88.5) | 94.7 (99.1) | 79.7 (88.5) |
| BE91 | 67.1 (72.6) | 67.1 (71.7) | 80.6 (88.5) | 100 (100) | 80.0 (88.5) |
| BE92 | 65.9 (72.6) | 66.8 (71.7) | 86.2 (94.7) | 80.0 (88.5) | 100 (100) |
| T1-12 | 66.5 (71.7) | 63.8 (70.8) | 62.7 (70.8) | 65.0 (71.7) | 60.9 (69.0) |
| T7-13 | 66.5 (71.7) | 64.4 (70.8) | 62.4 (69.0) | 64.7 (70.8) | 62.7 (68.1) |
| BE93 | 65.0 (70.8) | 62.7 (69.9) | 62.4 (69.9) | 65.0 (70.8) | 61.2 (68.1) |
| T9-14 | 68.2 (75.2) | 68.8 (73.5) | 63.5 (71.7) | 64.4 (72.6) | 64.4 (70.8) |
| T10-15 | 67.9 (75.2) | 68.5 (73.5) | 63.8 (71.7) | 65.0 (72.6) | 64.4 (70.8) |
| GB48 | 67.4 (75.2) | 66.2 (76.1) | 67.4 (71.7) | 67.4 (72.6) | 63.8 (71.7) |
| GB116 | 67.4 (77.0) | 65.6 (76.1) | 66.8 (69.9) | 66.5 (70.8) | 62.7 (69.9) |
| GB215 | 66.8 (72.6) | 66.2 (75.2) | 66.5 (67.3) | 66.5 (69.9) | 62.4 (67.3) |
| GB358 | 67.7 (76.1) | 67.9 (77.0) | 66.5 (70.8) | 67.1 (71.7) | 62.9 (70.8) |
| GB549 | 68.8 (76.1) | 63.5 (74.3) | 65.9 (71.7) | 67.7 (74.3) | 62.7 (71.7) |
| GB809 | 68.8 (73.5) | 67.1 (74.3) | 67.9 (69.9) | 68.5 (73.4) | 65.3 (69.9) |
| BE95 | 69.1 (75.2) | 69.1 (77.0) | 68.5 (73.5) | 71.5 (76.1) | 67.9 (73.5) |
| CHR18-18 | 67.1 (75.2) | 68.2 (77.0) | 67.4 (71.7) | 67.9 (74.3) | 66.8 (71.7) |
| HCV isolates | 3a<br>BE93 | 3b<br>T10 | 4a<br>GB358 | 4b<br>GB549 | 4c<br>GB809 | 5a<br>BE95 |
| HCV-1-1 | 65.0 (70.8) | 67.9 (75.2) | 67.7 (76.1) | 68.8 (76.1) | 68.8 (73.5) | 69.1 (75.2) |
| HCV-J1-2 | 66.2 (70.8) | 67.7 (75.2) | 68.2 (76.1) | 69.7 (76.1) | 69.4 (73.5) | 67.9 (76.1) |
| HCV-H-3 | 65.0 (69.0) | 66.2 (73.5) | 66.8 (74.3) | 67.7 (74.3) | 67.7 (71.7) | 67.9 (73.5) |
| HCV-J-4 | 65.6 (70.8) | 69.1 (75.2) | 65.6 (77.0) | 67.1 (77.0) | 65.6 (74.3) | 68.8 (77.9) |
| HCV-JK1-5 | 63.8 (69.9) | 67.4 (71.7) | 64.1 (75.2) | 64.7 (74.3) | 66.5 (74.3) | 68.2 (76.1) |
| HCV-CHINA-6 | 62.1 (68.1) | 67.1 (71.7) | 65.9 (75.2) | 63.8 (72.6) | 65.0 (72.6) | 67.7 (75.2) |
| HCV-T-7 | 62.4 (69.9) | 68.5 (73.5) | 67.1 (77.0) | 65.3 (74.3) | 66.5 (74.3) | 69.4 (77.9) |
| HC-J4.91-8 | 65.3 (71.7) | 69.1 (75.2) | 65.0 (77.0) | 65.9 (75.2) | 66.2 (74.3) | 68.2 (77.0) |
| HCV-TA-9 | 63.5 (69.9) | 67.4 (73.5) | 64.4 (75.2) | 64.7 (73.5) | 66.5 (72.6) | 68.2 (76.1) |
| HCV-JT-10 | 63.5 (69.9) | 67.4 (73.5) | 64.4 (75.2) | 64.7 (73.5) | 66.5 (72.6) | 68.2 (76.1) |
| HCV-BK-11 | 62.7 (69.0) | 67.1 (72.6) | 65.6 (76.1) | 63.5 (73.5) | 65.3 (73.5) | 67.0 (76.1) |
| BE90 | 62.7 (69.9) | 68.5 (73.5) | 67.9 (77.0) | 63.5 (74.3) | 67.1 (74.3) | 69.1 (77.0) |
| HC-J6-16 | 62.4 (69.9) | 63.8 (71.7) | 66.5 (70.8) | 65.9 (71.7) | 67.9 (69.9) | 68.5 (73.5) |
| HC-J8-17 | 63.5 (70.8) | 64.7 (72.6) | 65.6 (71.7) | 65.9 (74.3) | 67.4 (73.5) | 68.2 (76.1) |
| BE91 | 65.0 (70.8) | 65.0 (72.6) | 67.1 (71.7) | 67.7 (74.3) | 68.5 (73.5) | 71.5 (76.1) |
| BE92 | 61.2 (68.1) | 64.4 (70.8) | 62.9 (70.8) | 62.7 (71.7) | 65.3 (69.9) | 67.9 (73.5) |
| T1-12 | 95.6 (98.2) | 79.7 (85.8) | 70.6 (76.1) | 68.2 (75.2) | 69.1 (74.3) | 67.1 (69.9) |
| T7-13 | 93.8 (95.6) | 80.3 (87.6) | 70.6 (77.9) | 67.9 (77.9) | 70.3 (76.1) | 67.7 (70.8) |
| BE93 | 100 (100) | 78.8 (95.8) | 70.0 (76.1) | 66.2 (75.2) | 69.4 (74.3) | 67.4 (69.0) |
| T9-14 | 77.9 (85.0) | 98.5 (99.1) | 72.4 (78.8) | 71.2 (82.3) | 70.6 (77.9) | 68.2 (73.5) |
| T10-15 | 78.8 (85.8) | 100 (100) | 72.9 (78.7) | 72.1 (82.3) | 70.6 (77.9) | 67.9 (72.6) |
| GB48 | 69.4 (76.1) | 72.7 (77.0) | 97.1 (98.2) | 80.0 (83.2) | 86.2 (92.0) | 69.1 (69.9) |
| GB116 | 70.0 (74.3) | 72.9 (77.0) | 96.2 (98.2) | 78.8 (83.2) | 85.2 (92.0) | 68.8 (69.9) |
| GB215 | 68.5 (74.3) | 71.5 (75.2) | 93.8 (96.5) | 80.0 (83.2) | 86.2 (92.0) | 68.2 (67.3) |
| GB358 | 70.0 (76.1) | 72.9 (78.8) | 100 (100) | 79.4 (85.0) | 87.4 (93.8) | 69.7 (70.8) |
| GB549 | 66.2 (75.2) | 72.1 (82.3) | 79.4 (85.0) | 100 (100) | 79.7 (87.6) | 67.1 (70.8) |
| GB809 | 69.4 (74.3) | 70.6 (77.9) | 87.4 (93.8) | 79.7 (87.6) | 100 (100) | 68.2 (69.9) |
| BE95 | 67.4 (69.0) | 67.9 (72.6) | 69.7 (70.8) | 67.1 (70.8) | 68.2 (69.9) | 100 (100) |
| CHR18-18 | 65.3 (67.3) | 66.2 (70.8) | 66.8 (69.0) | 63.8 (69.0) | 66.5 (69.0) | 92.9 (94.7) |

REFERENCES

Barany F (1991). Genetic disease detection and DNA amplification using cloned thermostable ligase. Proc Natl Acad Sci USA 88: 189-193.

Bej A, Mahbubani M, Miller R, Di Cesare J, Haff L, Atlas. R (1990) Mutiplex PCR amplification and immobilized capture probes for detection of bacterial pathogens and indicators in water. Mol Cell Probes 4: 353-365.

Bukh J, Purcell R, Miller R (1992). Sequence analysis of the 5' noncoding region of hepatitis C virus. Proc Natl Acad Sci USA 89: 4942-4946.

Bukh J, Purcell R, Miller R (1993) At least 12 genotypes of hepatitis C virus predicted by sequence analysis of the putative E1 gene of isolates collected worldwide. Proc. Natl. Acad. Sci. USA 90: 8234-8238.

Cha T, Beal E, Irvine B, Kolberg J, Chien D, Kuo G, Urdea M (1992) At least five related, but distinct, hepatitis C viral genotypes exist. Proc Natl Acad Sci USA 89: 7144-7148.

Chan S, Simmonds P, McOmish F, Yap P, Mitchell R, Dow B, Follett E (1991) Serological responses to infection with three different types of hepatitis C virus. Lancet 338: 1991.

Chan S, McOmish F, Holmes E, Dow B, Peutherer J, Follett E, Yap P, Simmonds P (1992a) Analysis of a new hepatitis C virus type and its phylogenetic relationship to existing variants. J Gen Virol 73: 1131-1141.

Chan S, Holmes E, McOmish F, Follett E, Yap P, Simmonds P (1992b) Phylogenetic analysis of a new, highly divergent HCV type (type 3): effect of sequence variability on serological responses to infection. In: Hepatitis C virus and related viruses, Molecular Virology and pathogenesis. First Annual Meeting, Venice, Italy. Abstract book D5, 73.

Chomczynski P, Sacchi N (1987) Single step method of RNA isolation by acid guanidinium thiocyanate-phenol-chloroform extraction. Anal Biochem 162: 156-159.

Choo Q, Richman K, Han J, Berger K, Lee C, Dong C, Gallegos C, Coit D, Medina-Selby A, Barr P, Weiner A, Bradley D, Kuo G, Houghton M (1991) Genetic organization and diversity of the hepatitis C virus. Proc Natl Acad Sci USA 88: 2451-2455.

Compton J (1991). Nucleic acid sequence-based amplification. Nature, 350: 91-92.

Duck P (1990). Probe amplifier system based on chimeric cycling oligonucleotides. Biotechniques 9, 142-147.

Enomoto. N, Takada A, Nakao T, Date T (1990) There are two types of hepatitis C virus in Japan. Biochem Biophys Res Comm 170: 1021-1025.

Guatelli J, Whitfield K, Kwoh D, Barringer K, Richman D, Gengeras T (1990) Isothermal, in vitro amplification of nucleic acids by a multienzyme reaction modeled after retroviral replication. Proc Natl Acad Sci USA 87: 1874-1878.

Inchaupse G, Abe K, Zebedee S, Nasoff M, Prince A (1991) Use of conserved sequences from hepatitis C virus for detection of viral RNA in infected sera by polymerase chain reaction. Hepatology, 14: 595-600.

Jacobs K, Rudersdorf R, Neill S, Dougherty J, Brown E, Fritsch E (1988) The thermal stability of oligonucleotide duplexes is sequence independent in tedraalkylammonium salt solutions: application to identifying recombinant DNA clones. Nucl Acids Res 16: 4637-4650.

Kanai K, Kako M, Okamoto H (1992) HCV genotypes in chronic hepatitis C and response to interferon. Lancet 339: 1543

Kato N, Hijikata M, Ootsuyama Y, Nakagawa M, Ohkoshi S, Sugimura T, Shimotohno K (1990) Molecular cloning of the human hepatitis C virus genome from Japanese patients with non-A, non-B hepatitis. Proc Natl Acad Sci USA 87: 9524-9528.

Kubo Y, Takeuchi K, Boonmar S, Katayama T, Choo Q, Kuo G, Weiner A, Bradley D, Houghton M, Saito I, Miyamura T (1989) A cDNA fragment of hepatitis C virus isolated from an implicated donor of post-transfusion non-A, non-B hepatitis in Japan. Nucl Acids Res 17: 10368-10372.

Kwoh D, Davis G, Whitfield K, Chappelle H, Dimichele L, Gingeras T (1989). Transcription-based amplification system and detection of amplified human immunodeficiency virus type 1 with a bead-based sandwich hybridization format. Proc Natl Acad Sci USA, 86: 1173-1177.

Landegren U, Kaiser R, Sanders J, Hood L (1988). A ligase-mediated gene detection technique. Science 241: 1077-1080.

Lee C, Cheng C, Wang J, Lumeng L (1992) Identification of hepatitis C viruses with a nonconserved sequence of the 5' untranslated region. J Clin Microbiol 30: 1602-1604.

Lizardi P, Guerra C, Lomeli H, Tussie-Luna I, Kramer F (1988) Exponential amplification of recombinant RNA hybridization probes. Bio/Technology 6: 1197-1202.

Lomeli H, Tyagi S, Printchard C, Lisardi P, Kramer F (1989) Quantitative assays based on the use of replicatable hybridization probes. Clin Chem 35: 1826-1831.

Maniatis T, Fritsch E, Sambrook J (1982) Molecular cloning: a laboratory manual. Cold Spring Harbor Laboratory Press, Cold Spring Harbor, N.Y.

Mori S, Kato N, Yagyu A, Tanaka T, Ikeda Y, Petchclai B, Chiewsilp P, Kurimura T, Shimotohno K (1992) A new type of hepatitis C virus in patients in Thailand. Biochem Biophys Res Comm 183: 334-342.

Nakao T, Enomoto N, Takada N, Takada A, Date T (1991) Typing of hepatitis C virus genomes by restriction length polymorphism. J Gen Virol 72: 2105-2112.

Okamoto H, Okada S, Sugiyama Y, Yotsumoto S, Tanaka T, Yoshizawa H, Tsuda F, Miyakawa Y, Mayumi M (1990) The 5' terminal sequence of the hepatitis C virus genome. Japan J Exp Med 60: 167-177.

Okamoto H, Okada S, Sugiyama Y, Kurai K, Iizuka H, Machida A, Miyakawa Y, Mayumi M (1991) Nucleotide sequence of the genomic RNA of hepatitis C virus isolated from a human carrier: comparison with reported isolates for conserved and divergent regions. J Gen Virol 72: 2697-2704.

Okamoto H, Sugivama Y, Okada S, Kurai K, Akahane Y, Sugai Y, Tanaka T, Sato K, Tsuda F, Miyakawa Y, Mayumi M (1992a) Typing hepatitis C virus by polymerase chain reaction with type-specific primers: application to clinical surveys and tracing infectious sources. J Gen Virol 73: 673-679.

Okamoto H, Kurai K, Okada S, Yamamoto K, Lizuka H, Tanaka T, Fukuda S, Tsuda F, Mishiro S (1992b) Full-length sequences of a hepatitis C virus genome having poor homology to reported isolates: comparative study of four distinct genotypes. Virology 188: 331-341.

Pozatto G, Moretti M, Franzin F, Croce L, Tiribelli C, Masayu T, Kaneko S, Unoura M, Kobayashi K (1991) Severity of liver disease with different hepatitis C viral clones. Lancet 338: 509

Saiki r, Gelfand D, Stoffel S, Scharf S, Higuchi R, Horn G, Mullis K, Erlich H (1988). Primer-directed enzymatic amplification of DNA with a thermostable DNA polymerase. Science 239: 487-491.

Strezoska Z, Paunesku T, Radosavljevic D, Labat I, Drmanac R, Crkvenjakov R (1991) DNA sequencing by hybridization: 100 bases read by a non-gel-based method. Proc Natl Acad Sci USA 88: 10089-10093.

Takamizawa A, Mori C, Fuke I, Manabe S, Murakami S, Fujita J, Onishi E, Andoh T, Yoshida I, Okayama H (1991) Structure and organization of the hepatitis C virus genome isolated from human carriers. J Virol 65: 1105-1113.

Walker G, Little M, Nadeau J, Shank D (1992). Isothermal in vitro amplification of DNA by a restriction enzyme/DNA polymerase system. Proc Natl Acad Sci USA 89: 392-396.

Wu D, Wallace B (1989). The ligation amplification reaction (LAR)-amplification of specific DNA sequences using sequential rounds of template-dependent ligation. Genomics 4: 560-569.

Yoshioka K, Kakumu S, Wakita T, Ishikawa T, Itoh Y, Takayanagi M, Higashi Y, Shibata M, Morishima T (1992) Detection of hepatitis C virus by polymerase chain reaction and response to interferon-therapy: relationship to genotypes of hepatitis C virus. Hepatology 16: 293-299.

The invention claimed is:

1. An isolated polynucleic acid consisting of 15-50 nucleotides capable of specifically hybridizing with an HCV NS5B sequence portion of a target sequence, said HCV NS5B sequence portion being a nucleic acid sequence encoding a NS5B amino acid sequence defined by any one of SEQ ID NO:82 to SEQ ID NO:92, or a complement of a nucleic acid sequence encoding a NS5B amino acid sequence defined by any one of SEQ ID NO:82 to SEQ ID NO:92.

2. The isolated polynucleic acid of claim 1 hybridizing under conditions allowing detection of homologous target sequences comprising one or few mismatches.

3. The isolated polynucleic acid of claim 1 hybridizing under conditions allowing detection of completely homologous target sequences.

4. A capture probe or labeled probe consisting of a binding molecule or a detectable label, and a nucleic acid sequence of 15-50 nucleotides capable of specifically hybridizing with an HCV NS5B sequence portion of a target sequence, said HCV NS5B sequence portion being a nucleic acid sequence encoding a NS5B amino acid sequence defined by any one of SEQ ID NO:82 to SEQ ID NO:92, or a complement of a nucleic acid sequence encoding a NS5B amino acid sequence defined by any one of SEQ ID NO:82 to SEQ ID NO:92.

5. An isolated HCV virus characterized by any of the HCV NS5 nucleotide sequences selected from the group consisting of a nucleic acid sequence encoding any of SEQ ID NO:82 to SEQ ID NO:92.

6. A kit for detecting or typing HCV isolates comprising at least one isolated polynucleic acid of claim 1.

7. A solid substrate comprising the capture probe or labeled probe of claim 4 immobilized thereon.

8. An isolated polynucleic acid sequence comprising a polynucleic acid sequence encoding any of amino acid sequences defined by SEQ ID NO:82 to SEQ ID NO:92, or a complement thereof.

9. An isolated polynucleic acid comprising 15-50 nucleotides capable of specifically hybridizing with an HCV NS5B sequence portion of a target sequence, said HCV NS5B sequence portion being a nucleic acid sequence encoding a NS5B amino acid sequence defined by any one of SEQ ID NO:82 to SEQ ID NO:92, or a complement of a nucleic acid sequence encoding a NS5B amino acid sequence defined by any one of SEQ ID NO:82 to SEQ ID NO:92.

* * * * *

SEQUENCE LISTING (1) GENERAL INFORMATION:

(iii) NUMBER OF SEQUENCES: 97

(2) INFORMATION FOR SEQ ID NO: 1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: genomic DNA (iii) HYPOTHETICAL: YES (iv) ANTI-SENSE: NO (vi) ORIGINAL SOURCE:
      (C) INDIVIDUAL ISOLATE: HCV (Kato et al., 1992)

(viii) POSITION IN GENOME:
      (A) CHROMOSOME/SEGMENT: HCV
      (B) MAP POSITION: Position -299 of 5' end (ix) FEATURE:
      (A) NAME/KEY: misc_feature
      (B) LOCATION: 1..27
      (D) OTHER INFORMATION: /standard_name=
          "Universal HCV primer HcPr98"

(xi) SEQUENCE DESCRIPTION: SEQ ID NO: 1:

CCCTGTGAGG AACTWCTGTC TTCACGC    27

(2) INFORMATION FOR SEQ ID NO: 2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: genomic DNA (iii) HYPOTHETICAL: NO (iv) ANTI-SENSE: YES (vi) ORIGINAL SOURCE:
      (C) INDIVIDUAL ISOLATE: HCV (Okamoto et al., 1991)

(viii) POSITION IN GENOME:
      (A) CHROMOSOME/SEGMENT: HCV
      (B) MAP POSITION: Position -1 of 5' end (ix) FEATURE:
      (A) NAME/KEY: misc_feature
      (B) LOCATION: 1..21
      (D) OTHER INFORMATION: /standard_name=

-continued

"Universal HCV primer HcPr29"

(xi) SEQUENCE DESCRIPTION: SEQ ID NO: 2:

GGTGCACGGT CTACGAGACC T                                                               21

(2) INFORMATION FOR SEQ ID NO: 3:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: genomic DNA (iii) HYPOTHETICAL: YES (iv) ANTI-SENSE: NO (vi) ORIGINAL SOURCE:
      (C) INDIVIDUAL ISOLATE: HCV (viii) POSITION IN GENOME:
      (A) CHROMOSOME/SEGMENT: HCV
      (B) MAP POSITION: Position -264 of 5' end (ix) FEATURE:
      (A) NAME/KEY: misc_feature
      (B) LOCATION: 1..26
      (D) OTHER INFORMATION: /standard_name=
         "Universal HCV primer HcPr95"

(xi) SEQUENCE DESCRIPTION: SEQ ID NO: 3:

TCTAGCCATG GCGTTAGTRY GAGTGT                                              26

(2) INFORMATION FOR SEQ ID NO: 4:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: genomic DNA (iii) HYPOTHETICAL: NO (iv) ANTI-SENSE: YES (vi) ORIGINAL SOURCE:
      (C) INDIVIDUAL ISOLATE: HCV (viii) POSITION IN GENOME:
      (A) CHROMOSOME/SEGMENT: HCV
      (B) MAP POSITION: Position -29 of 5' end (ix) FEATURE:
      (A) NAME/KEY: misc_feature
      (B) LOCATION: 1..26
      (D) OTHER INFORMATION: /standard_name=
         "Universal HCV primer HcPr96"

(xi) SEQUENCE DESCRIPTION: SEQ ID NO: 4:

CACTCGCAAG CACCCTATCA GGCAGT                                              26

(2) INFORMATION FOR SEQ ID NO: 5:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: genomic DNA -continued

```
        (iii) HYPOTHETICAL: NO (iv) ANTI-SENSE: NO (vi) ORIGINAL SOURCE:
              (C) INDIVIDUAL ISOLATE: HCV type 1 (Kato et al.,
                  1990)

(viii) POSITION IN GENOME:
              (A) CHROMOSOME/SEGMENT: HCV type 1
              (B) MAP POSITION: position -170 of the 5' end (ix) FEATURE:
              (A) NAME/KEY: misc_feature
              (B) LOCATION: 1..16
              (D) OTHER INFORMATION: /standard_name= "HCV type
                   1 specific Probe HcPr124"

(xi) SEQUENCE DESCRIPTION: SEQ ID NO: 5:

AATTGCCAGG ACGACC                                                 16

(2) INFORMATION FOR SEQ ID NO: 6:

(i) SEQUENCE CHARACTERISTICS:
              (A) LENGTH: 16 base pairs
              (B) TYPE: nucleic acid
              (C) STRANDEDNESS: single
              (D) TOPOLOGY: linear (ii) MOLECULE TYPE: genomic DNA (iii) HYPOTHETICAL: NO (iv) ANTI-SENSE: YES (vi) ORIGINAL SOURCE:
              (C) INDIVIDUAL ISOLATE: HCV type 1 (Kato et al.,
                  1990)

(viii) POSITION IN GENOME:
              (A) CHROMOSOME/SEGMENT: HCV type 1
              (B) MAP POSITION: position -117 of 5'end (ix) FEATURE:
              (A) NAME/KEY: misc_feature
              (B) LOCATION: 1..16
              (D) OTHER INFORMATION: /standard_name= "HCV type
                   1 specific Probe HcPr125"

(xi) SEQUENCE DESCRIPTION: SEQ ID NO: 6:

TCTCCAGGCA TTGAGC                                                 16

(2) INFORMATION FOR SEQ ID NO: 7:

(i) SEQUENCE CHARACTERISTICS:
              (A) LENGTH: 16 base pairs
              (B) TYPE: nucleic acid
              (C) STRANDEDNESS: single
              (D) TOPOLOGY: linear (ii) MOLECULE TYPE: genomic DNA (iii) HYPOTHETICAL: NO (iv) ANTI-SENSE: NO (vi) ORIGINAL SOURCE:
              (C) INDIVIDUAL ISOLATE: HCV type 1b (Kato et
                  al., 1990)

(viii) POSITION IN GENOME:
              (A) CHROMOSOME/SEGMENT: HCV type 1b
              (B) MAP POSITION: position -103 of the 5'end (ix) FEATURE:
```

(A) NAME/KEY: misc_feature
(B) LOCATION: 1..16
(D) OTHER INFORMATION: /standard_name= "HCV type
    1b specific Probe HcPr138"

(xi) SEQUENCE DESCRIPTION: SEQ ID NO: 7:

CCGCGAGACT GCTAGC                                              16

(2) INFORMATION FOR SEQ ID NO: 8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (vi) ORIGINAL SOURCE:
        (C) INDIVIDUAL ISOLATE: HCV type 2

(viii) POSITION IN GENOME:
        (A) CHROMOSOME/SEGMENT: HCV type 2
        (B) MAP POSITION: position -83 of the 5'end (ix) FEATURE:
        (A) NAME/KEY: misc_feature
        (B) LOCATION: 1..16
        (D) OTHER INFORMATION: /standard_name= "HCV type
            2 specific Probe HcPr147"

(xi) SEQUENCE DESCRIPTION: SEQ ID NO: 8:

TAGCGTTGGG TTGCGA                                              16

(2) INFORMATION FOR SEQ ID NO: 9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: YES (iv) ANTI-SENSE: NO (vi) ORIGINAL SOURCE:
        (C) INDIVIDUAL ISOLATE: HCV type 2a (Chan et
            al., 1992)

(viii) POSITION IN GENOME:
        (A) CHROMOSOME/SEGMENT: HCV type 2a
        (B) MAP POSITION: position -168 of 5' end (ix) FEATURE:
        (A) NAME/KEY: misc_feature
        (B) LOCATION: 1..16
        (D) OTHER INFORMATION: /standard_name= "HCV type
            2a specific probe HcPr136"

(xi) SEQUENCE DESCRIPTION: SEQ ID NO: 9:

TTRCCGGRAA GACTGG                                              16

(2) INFORMATION FOR SEQ ID NO: 10:

(i) SEQUENCE CHARACTERISTICS:
        (A) LENGTH: 16 base pairs
        (B) TYPE: nucleic acid

```
        (C) STRANDEDNESS: single
        (D) TOPOLOGY: linear (ii) MOLECULE TYPE: genomic DNA (iii) HYPOTHETICAL: YES (iv) ANTI-SENSE: YES (vi) ORIGINAL SOURCE:
         (C) INDIVIDUAL ISOLATE: HCV type 2a (Chan et
             al., 1992)

(viii) POSITION IN GENOME:
         (A) CHROMOSOME/SEGMENT: HCV type 2a
         (B) MAP POSITION: Position -117 of 5' end (ix) FEATURE:
         (A) NAME/KEY: misc_feature
         (B) LOCATION: 1..16
         (D) OTHER INFORMATION: /standard_name= "HCV type
             2a specific probe HcPr137"

(xi) SEQUENCE DESCRIPTION: SEQ ID NO: 10:

TGRCCGGGCA TAGAGT                                                       16

(2) INFORMATION FOR SEQ ID NO: 11:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: genomic DNA (iii) HYPOTHETICAL: NO (iv) ANTI-SENSE: NO (vi) ORIGINAL SOURCE:
         (C) INDIVIDUAL ISOLATE: HCV type 2b (Nakao et
             al., 1991)

(viii) POSITION IN GENOME:
         (A) CHROMOSOME/SEGMENT: HCV type 2b
         (B) MAP POSITION: position -168 of 5' end (ix) FEATURE:
         (A) NAME/KEY: misc_feature
         (B) LOCATION: 1..16
         (D) OTHER INFORMATION: /standard_name= "HCV type
             2b specific probe HcPr126"

(xi) SEQUENCE DESCRIPTION: SEQ ID NO: 11:

TTACCGGGAA GACTGG                                                       16

(2) INFORMATION FOR SEQ ID NO: 12:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: genomic DNA (iii) HYPOTHETICAL: NO (iv) ANTI-SENSE: YES (vi) ORIGINAL SOURCE:
         (C) INDIVIDUAL ISOLATE: HCV type 2b (Nakao et
             al., 1991)

(viii) POSITION IN GENOME:
```

-continued

```
            (A) CHROMOSOME/SEGMENT: HCV type 2b
            (B) MAP POSITION: position -117 of 5' end (ix) FEATURE:
            (A) NAME/KEY: misc_feature
            (B) LOCATION: 1..16
            (D) OTHER INFORMATION: /standard_name= "HCV type
                2b specific probe HcPr127"

(xi) SEQUENCE DESCRIPTION: SEQ ID NO: 12:

TGACCGGACA TAGAGT                                                      16

(2) INFORMATION FOR SEQ ID NO: 13:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: genomic DNA (iii) HYPOTHETICAL: NO (iv) ANTI-SENSE: NO (vi) ORIGINAL SOURCE:
            (C) INDIVIDUAL ISOLATE: HCV type 3

(viii) POSITION IN GENOME:
            (A) CHROMOSOME/SEGMENT: HCV type 3
            (B) MAP POSITION: position -170 of 5' end (ix) FEATURE:
            (A) NAME/KEY: misc_feature
            (B) LOCATION: 1..16
            (D) OTHER INFORMATION: /standard_name= "HCV type
                3 specific probe HcPr128"

(xi) SEQUENCE DESCRIPTION: SEQ ID NO: 13:

AATCGCTGGG GTGACC                                                      16

(2) INFORMATION FOR SEQ ID NO: 14:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: genomic DNA (iii) HYPOTHETICAL: NO (iv) ANTI-SENSE: YES (vi) ORIGINAL SOURCE:
            (C) INDIVIDUAL ISOLATE: HCV type 3

(viii) POSITION IN GENOME:
            (A) CHROMOSOME/SEGMENT: HCV type 3
            (B) MAP POSITION: position -117 of 5' end (ix) FEATURE:
            (A) NAME/KEY: misc_feature
            (B) LOCATION: 1..16
            (D) OTHER INFORMATION: /standard_name= "HCV type
                3 specific probe HcPr 129"

(xi) SEQUENCE DESCRIPTION: SEQ ID NO: 14:

TTTCTGGGTA TTGAGC                                                      16

(2) INFORMATION FOR SEQ ID NO: 15:
```

```
    (i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (vi) ORIGINAL SOURCE:
        (C) INDIVIDUAL ISOLATE: HCV type 3a (Chan et
            al., 1992)

(viii) POSITION IN GENOME:
        (A) CHROMOSOME/SEGMENT: HCV type 3a
        (B) MAP POSITION: position -146 of 5' end (ix) FEATURE:
        (A) NAME/KEY: misc_feature
        (B) LOCATION: 1..16
        (D) OTHER INFORMATION: /standard_name= "HCV type
            3a specific probe HcPr140"

(xi) SEQUENCE DESCRIPTION: SEQ ID NO: 15:

TCTTGGAGCA ACCCGC                                                    16

(2) INFORMATION FOR SEQ ID NO: 16:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (vi) ORIGINAL SOURCE:
        (C) INDIVIDUAL ISOLATE: HCV type 3b (Chan et
            al., 1992)

(viii) POSITION IN GENOME:
        (A) CHROMOSOME/SEGMENT: HCV type 3b
        (B) MAP POSITION: position -146 of 5' end (ix) FEATURE:
        (A) NAME/KEY: misc_feature
        (B) LOCATION: 1..16
        (D) OTHER INFORMATION: /standard_name= "HCV type
            3b specific probe HcPr139"

(xi) SEQUENCE DESCRIPTION: SEQ ID NO: 16:

TCTTGGAACA ACCCGC                                                    16

(2) INFORMATION FOR SEQ ID NO: 17:

(i) SEQUENCE CHARACTERISTICS:
        (A) LENGTH: 16 base pairs
        (B) TYPE: HCV type 4 (Bukh et al.,
            1992)
        (C) STRANDEDNESS: single
        (D) TOPOLOGY: linear (ii) MOLECULE TYPE: genomic DNA (iii) HYPOTHETICAL: YES (iv) ANTI-SENSE: NO (vi) ORIGINAL SOURCE:
```

```
   (viii) POSITION IN GENOME:
         (A) CHROMOSOME/SEGMENT: HCV type 4
         (B) MAP POSITION: position -170 of 5' end (ix) FEATURE:
         (A) NAME/KEY: misc_feature
         (B) LOCATION: 1..16
         (D) OTHER INFORMATION: /standard_name= "HCV type
             4 specific probe HcPr 144"

(xi) SEQUENCE DESCRIPTION: SEQ ID NO: 17:

AATYGCCGGG ATGACC                                                16

(2) INFORMATION FOR SEQ ID NO: 18:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: genomic DNA (iii) HYPOTHETICAL: NO (iv) ANTI-SENSE: NO (vi) ORIGINAL SOURCE:
         (C) INDIVIDUAL ISOLATE: HCV type 4

(viii) POSITION IN GENOME:
         (A) CHROMOSOME/SEGMENT: HCV type 4
         (B) MAP POSITION: position -147 of 5' end (ix) FEATURE:
         (A) NAME/KEY: misc_feature
         (B) LOCATION: 1..16
         (D) OTHER INFORMATION: /standard_name= "HCV type
             4 specific probe HcPr145"

(xi) SEQUENCE DESCRIPTION: SEQ ID NO: 18:

TTCTTGGAAC TAACCC                                                16

(2) INFORMATION FOR SEQ ID NO: 19:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: genomic DNA (iii) HYPOTHETICAL: NO (iv) ANTI-SENSE: YES (vi) ORIGINAL SOURCE:
         (C) INDIVIDUAL ISOLATE: HCV type 4

(viii) POSITION IN GENOME:
         (A) CHROMOSOME/SEGMENT: HCV type 4
         (B) MAP POSITION: position -117 of 5' end (ix) FEATURE:
         (A) NAME/KEY: misc_feature
         (B) LOCATION: 1..16
         (D) OTHER INFORMATION: /standard_name= "HCV type
             4 specific probe HcPr146"

(xi) SEQUENCE DESCRIPTION: SEQ ID NO: 19:

TTTCCGGGCA TTGAGC                                                16
```

(2) INFORMATION FOR SEQ ID NO: 20:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: genomic DNA (iii) HYPOTHETICAL: YES (iv) ANTI-SENSE: NO (vi) ORIGINAL SOURCE:
       (C) INDIVIDUAL ISOLATE: HCV (Kato et al., 1990)

(viii) POSITION IN GENOME:
       (A) CHROMOSOME/SEGMENT: HCV
       (B) MAP POSITION: position -115 of 5' end (ix) FEATURE:
       (A) NAME/KEY: misc_feature
       (B) LOCATION: 1..16
       (D) OTHER INFORMATION: /standard_name=
           "Universal HCV probe HcPr 142"

(xi) SEQUENCE DESCRIPTION: SEQ ID NO: 20:

TTGGGCGYGC CCCCGC                                                16

(2) INFORMATION FOR SEQ ID NO: 21:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: genomic DNA (iii) HYPOTHETICAL: NO (iv) ANTI-SENSE: NO (vi) ORIGINAL SOURCE:
       (C) INDIVIDUAL ISOLATE: HCV type 3

(viii) POSITION IN GENOME:
       (A) CHROMOSOME/SEGMENT: HCV  type 3
       (B) MAP POSITION: position -103 of 5' end (ix) FEATURE:
       (A) NAME/KEY: misc_feature
       (B) LOCATION: 1..16
       (D) OTHER INFORMATION: /standard_name= "HCV type
           3 specific probe HcPr 154"

(xi) SEQUENCE DESCRIPTION: SEQ ID NO: 21:

CCGCGAGATC ACTAGC                                                16

(2) INFORMATION FOR SEQ ID NO: 22:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: genomic DNA (iii) HYPOTHETICAL: NO (iv) ANTI-SENSE: NO (vi) ORIGINAL SOURCE:
       (C) INDIVIDUAL ISOLATE: HCV type 2a (Okamoto et al., 1991)

(viii) POSITION IN GENOME:
              (A) CHROMOSOME/SEGMENT: HCV type 2a
              (B) MAP POSITION: position -165 of 5' end (ix) FEATURE:
              (A) NAME/KEY: misc_feature
              (B) LOCATION: 1..16
              (D) OTHER INFORMATION: /standard_name= "HCV type
                  2a specific probe HcPr156"

(xi) SEQUENCE DESCRIPTION: SEQ ID NO: 22:

CCGGGAAGAC TGGGTC                                                            16

(2) INFORMATION FOR SEQ ID NO: 23:

(i) SEQUENCE CHARACTERISTICS:
              (A) LENGTH: 16 base pairs
              (B) TYPE: nucleic acid
              (C) STRANDEDNESS: single
              (D) TOPOLOGY: linear (ii) MOLECULE TYPE: genomic DNA (iii) HYPOTHETICAL: NO (iv) ANTI-SENSE: NO (vi) ORIGINAL SOURCE:
              (C) INDIVIDUAL ISOLATE: HCV type 2b (Okamoto et
                  al., 1992)

(viii) POSITION IN GENOME:
              (A) CHROMOSOME/SEGMENT: HCV type 2b
              (B) MAP POSITION: position - 165 of 5' end (ix) FEATURE:
              (A) NAME/KEY: misc_feature
              (B) LOCATION: 1..16
              (D) OTHER INFORMATION: /standard_name= "HCV type
                  2b specific probe HcPr157"

(xi) SEQUENCE DESCRIPTION: SEQ ID NO: 23:

CCGGAAAGAC TGGGTC                                                            16

(2) INFORMATION FOR SEQ ID NO: 24:

(i) SEQUENCE CHARACTERISTICS:
              (A) LENGTH: 16 base pairs
              (B) TYPE: nucleic acid
              (C) STRANDEDNESS: single
              (D) TOPOLOGY: linear (ii) MOLECULE TYPE: genomic DNA (iii) HYPOTHETICAL: NO (iv) ANTI-SENSE: NO (vi) ORIGINAL SOURCE:
              (C) INDIVIDUAL ISOLATE: HCV type 2a (Okamoto et
                  al., 1991)

(viii) POSITION IN GENOME:
              (A) CHROMOSOME/SEGMENT: HCV type 2a
              (B) MAP POSITION: position -136 of 5' end (ix) FEATURE:
              (A) NAME/KEY: misc_feature
              (B) LOCATION: 1..16
              (D) OTHER INFORMATION: /standard_name= "HCV type
                  2a specific probe HcPr158"

(xi) SEQUENCE DESCRIPTION: SEQ ID NO: 24:

```
ACCCACTCTA TGCCCG                                                 16
```

(2) INFORMATION FOR SEQ ID NO: 25:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (vi) ORIGINAL SOURCE:
        (C) INDIVIDUAL ISOLATE: HCV type 2b (Okamoto et
            al., 1992)

(viii) POSITION IN GENOME:
        (A) CHROMOSOME/SEGMENT: HCV type 2b
        (B) MAP POSITION: position -136 of 5' end (ix) FEATURE:
        (A) NAME/KEY: misc_feature
        (B) LOCATION: 1..16
        (D) OTHER INFORMATION: /standard_name= "HCV type
            2b specific probe HcPr159"

(xi) SEQUENCE DESCRIPTION: SEQ ID NO: 25:

```
ACCCACTCTA TGTCCG                                                 16
```

(2) INFORMATION FOR SEQ ID NO: 26:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: YES (vi) ORIGINAL SOURCE:
        (C) INDIVIDUAL ISOLATE: HCV type 2 (Okamoto et
            al., 1992)

(viii) POSITION IN GENOME:
        (A) CHROMOSOME/SEGMENT: HCV type 2
        (B) MAP POSITION: position -126 of 5' end (ix) FEATURE:
        (A) NAME/KEY: misc_feature
        (B) LOCATION: 1..16
        (D) OTHER INFORMATION: /standard_name= "HCV type
            2 specific probe HcPr160"

(xi) SEQUENCE DESCRIPTION: SEQ ID NO: 26:

```
ATAGAGTGGG TTTATC                                                 16
```

(2) INFORMATION FOR SEQ ID NO: 27:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO

```
        (iv) ANTI-SENSE: NO (vi) ORIGINAL SOURCE:
             (C) INDIVIDUAL ISOLATE: HCV (Kato et al., 1990)

(viii) POSITION IN GENOME:
             (A) CHROMOSOME/SEGMENT: HCV
             (B) MAP POSITION: Position -195 of 5' end (ix) FEATURE:
             (A) NAME/KEY: misc_feature
             (B) LOCATION: 1..16
             (D) OTHER INFORMATION: /standard_name=
                 "Universal HCV probe HcPr153"

(xi) SEQUENCE DESCRIPTION: SEQ ID NO: 27:

TCTGCGGAAC CGGTGA                                                    16

(2) INFORMATION FOR SEQ ID NO: 28:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: genomic DNA (iii) HYPOTHETICAL: YES (iv) ANTI-SENSE: NO (xi) SEQUENCE DESCRIPTION: SEQ ID NO: 28:

AATTGCCAGG AYGACC                                                    16

(2) INFORMATION FOR SEQ ID NO: 29:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: genomic DNA (iii) HYPOTHETICAL: YES (iv) ANTI-SENSE: NO (xi) SEQUENCE DESCRIPTION: SEQ ID NO: 29:

GCTCAGTGCC TGGAGA                                                    16

(2) INFORMATION FOR SEQ ID NO: 30:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: genomic DNA (iii) HYPOTHETICAL: YES (iv) ANTI-SENSE: NO (xi) SEQUENCE DESCRIPTION: SEQ ID NO: 30:

CCGCGAGACY GCTAGC                                                    16

(2) INFORMATION FOR SEQ ID NO: 31:
```

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 31:

CCCCGCAAGA CTGCTA                                                              16

(2) INFORMATION FOR SEQ ID NO: 32:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 32:

CGTACAGCCT CCAGGC                                                              16

(2) INFORMATION FOR SEQ ID NO: 33:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: YES (xi) SEQUENCE DESCRIPTION: SEQ ID NO: 33:

GGACCCAGTC TTCCTG                                                              16

(2) INFORMATION FOR SEQ ID NO: 34:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 34:

TGCCTGGTCA TTTGGG                                                              16

(2) INFORMATION FOR SEQ ID NO: 35:

(i) SEQUENCE CHARACTERISTICS:
        (A) LENGTH: 16 base pairs
        (B) TYPE: nucleic acid
        (C) STRANDEDNESS: single (D) TOPOLOGY: linear (ii) MOLECULE TYPE: genomic DNA (iii) HYPOTHETICAL: NO (iv) ANTI-SENSE: YES (xi) SEQUENCE DESCRIPTION: SEQ ID NO: 35:

TKTCTGGGTA TTGAGC                                                           16

(2) INFORMATION FOR SEQ ID NO: 36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 36:

CCGCAAGATC ACTAGC                                                           16

(2) INFORMATION FOR SEQ ID NO: 37:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 37:

GAGTGTTGTA CAGCCT                                                           16

(2) INFORMATION FOR SEQ ID NO: 38:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 38:

AATCGCCGGG ATGACC                                                           16

(2) INFORMATION FOR SEQ ID NO: 39:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 39:

GAGTGTTGTG CAGCCT                                                    16

(2) INFORMATION FOR SEQ ID NO: 40:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 40:

AATCGCCGGG ACGACC                                                    16

(2) INFORMATION FOR SEQ ID NO: 41:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 41:

AATGCCCGGC AATTTG                                                    16

(2) INFORMATION FOR SEQ ID NO: 42:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 42:

AATCGCCGAG ATGACC                                                    16

(2) INFORMATION FOR SEQ ID NO: 43:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 43:

AATGCTCGGA AATTTG                                                      16

(2) INFORMATION FOR SEQ ID NO: 44:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 44:

GAGTGTCGAA CAGCCT                                                      16

(2) INFORMATION FOR SEQ ID NO: 45:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 45:

AATTGCCGGG ATGACC                                                      16

(2) INFORMATION FOR SEQ ID NO: 46:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: YES (xi) SEQUENCE DESCRIPTION: SEQ ID NO: 46:

TCTCCGGGCA TTGAGC                                                      16

(2) INFORMATION FOR SEQ ID NO: 47:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 47:

AATTGCCGGG ACGACC                                                      16

(2) INFORMATION FOR SEQ ID NO: 48:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 48:

GGGTCCTTTC CATTGG                                                  16

(2) INFORMATION FOR SEQ ID NO: 49:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 49:

AATCGCCAGG ATGACC                                                  16

(2) INFORMATION FOR SEQ ID NO: 50:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 50:

TGCCTGGAAA TTTGGG                                                  16

(2) INFORMATION FOR SEQ ID NO: 51:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 51:

GAGTGTCGTA CAGCCT                                                  16

(2) INFORMATION FOR SEQ ID NO: 52:

(i) SEQUENCE CHARACTERISTICS:

```
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 52:

AGTYCACCGG AATCGC                                                    16

(2) INFORMATION FOR SEQ ID NO: 53:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 53:

GGAATCGCCA GGACGA                                                    16

(2) INFORMATION FOR SEQ ID NO: 54:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO: 54:

GAATCGCCGG GTTGAC                                                    16

(2) INFORMATION FOR SEQ ID NO: 55:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: jp62

(viii) POSITION IN GENOME:
        (B) MAP POSITION: 5' untranslated region (xi) SEQUENCE DESCRIPTION: SEQ ID NO: 55:

GAGTGTCGTA CAGCCTCCAG GCCCCCCCCT CCCGGGAGAG                           40

CCATAGTGGT CTGCGGAACC GGTGAGTACA CCGGAATTGC                           80

CGGGAAGACT GGGTCCTTTC TTGGATAAAC CCACTCTATG                          120

CCCGGCCATT TGGGCGTGCC CCCGCAAGAC TGCTAGCCGA                          160
```

```
GTAGCGTTGG GTTGCGA                                                          177

(2) INFORMATION FOR SEQ ID NO: 56:

(i) SEQUENCE CHARACTERISTICS:
          (A) LENGTH: 177 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (B) CLONE: gb81

(viii) POSITION IN GENOME:
          (B) MAP POSITION: 5' untranslated region (xi) SEQUENCE DESCRIPTION: SEQ ID NO: 56:

GAGTGTCGTA CAGCCTCCAG GCCCCCCCCT CCCGGGAGAG                                   40

CCATAGTGGT CTGCGGAACC GGTGAGTACA CCGGAATCGC                                   80

CGGGAAGACT GGGTCCTTTC TTGGATAAAC CCACTCTATG                                  120

CCCGGTCATT TGGGCGTGCC CCCGCAAGAC CGCTAGCCGA                                  160

GTAGCGTTGG GTTGCGA                                                          177

(2) INFORMATION FOR SEQ ID NO: 57:

(i) SEQUENCE CHARACTERISTICS:
          (A) LENGTH: 177 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (B) CLONE: br56

(viii) POSITION IN GENOME:
          (B) MAP POSITION: 5' untranslated region (xi) SEQUENCE DESCRIPTION: SEQ ID NO: 57:

GAGTGTCGTG CAGCCTCCAG GCCCCCCCCT CCCGGGAGAG                                   40

CCATAGTGGT CTGCGGAACC GGTGAGTACA CCGGAATCGC                                   80

TGGGGTGACC GGGTCCTTTC TTGGAGCAAC CCGCTCAATA                                  120

CCCAGAAATT TGGGCGTGCC CCCGCGAGAT CACTAGCCGA                                  160

GTAGTGTTGG GTCGCGA                                                          177

(2) INFORMATION FOR SEQ ID NO: 58:

(i) SEQUENCE CHARACTERISTICS:
          (A) LENGTH: 177 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (B) CLONE: bu79

(viii) POSITION IN GENOME:
          (B) MAP POSITION: 5'untranslated region (xi) SEQUENCE DESCRIPTION: SEQ ID NO: 58:

GAGTGTTGTA CAGCCTCCAG GCCCCCCCCT CCCGGGAGAG                                   40
```

```
CCATAGTGGT CTGCGGAACC GGTGAGTACA CCGGAATCGC                   80

CGGGACGACC GGGTCCTTTC TTGGATTAAC CCGCTCAATG                  120

CCCGGAAATT TGGGCGTGCC CCCGCGAGAC TGCTAGCCGA                  160

GTAGTGTTGG GTCGCGA                                          177

(2) INFORMATION FOR SEQ ID NO: 59:

(i) SEQUENCE CHARACTERISTICS:
         (A) LENGTH: 178 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (B) CLONE: bu74

(viii) POSITION IN GENOME:
         (B) MAP POSITION: 5' untranslated region (xi) SEQUENCE DESCRIPTION: SEQ ID NO: 59:

GAGTGTTGTG CAGCCTCCAG GACCCCCCCT CCCGGGAGAG                   40

CCATAGTGGT CTGCGGAACC GGTGAGTCCA CCGGAATCGC                   80

CGGGATGACC GGGTCCTTTC TTGGAACTAA CCCGCTCAAT                  120

GCCCGGAAAT TTGGGCGTGC CCCCGCGAGA CTGCTAGCCG                  160

AGTAGTGTTG GGTCGCGA                                         178

(2) INFORMATION FOR SEQ ID NO: 60:

(i) SEQUENCE CHARACTERISTICS:
         (A) LENGTH: 178 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (B) CLONE: gb80

(viii) POSITION IN GENOME:
         (B) MAP POSITION: 5' untranslated region (xi) SEQUENCE DESCRIPTION: SEQ ID NO: 60:

GAGTGTCGTG CAGCCTCCAG GCCCCCCCCT CCCGGGAGAG                   40

CCATAGTGGT CTGCGGAACC GGTGAGTACA CCGGAATCGC                   80

CGGGATGACC GGGTCCTTTC TTGGAACTAA CCCGCTCAAT                  120

GCCCGGAAAT TTGGGCGTGC CCCCGCGAGA CTGCTAGCCG                  160

AGTAGTGTTG GGTCGCGA                                         178

(2) INFORMATION FOR SEQ ID NO: 61:

(i) SEQUENCE CHARACTERISTICS:
         (A) LENGTH: 177 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (B) CLONE: be82 (also referred to as be99)
```

(viii) POSITION IN GENOME:
              (B) MAP POSITION: 5' untranslated region (xi) SEQUENCE DESCRIPTION: SEQ ID NO: 61:

GAGTGTCGTG CAGCCTCCAG GACCCCCCCT CCCGGGAGAG                    40

CCATAGTGGT CTGCGGAACC GGTGAGTACA CCGGAATTGC                    80

CAGGACGACC GGGTCCTTTC TTGGATCAAC CCGCTCAATG                   120

CCTGGAGATT TGGGCGTGCC CCCGCGAGAC CGCTAGCCGA                   160

GTAGTGTTGG GTCGCGA                                            177

(2) INFORMATION FOR SEQ ID NO: 62:

(i) SEQUENCE CHARACTERISTICS:
              (A) LENGTH: 177 base pairs
              (B) TYPE: nucleic acid
              (C) STRANDEDNESS: single
              (D) TOPOLOGY: linear (ii) MOLECULE TYPE: cDNA (vii) IMMEDIATE SOURCE:
              (B) CLONE: be90

(viii) POSITION IN GENOME:
              (B) MAP POSITION: 5' untranslated region (xi) SEQUENCE DESCRIPTION: SEQ ID NO: 62:

GAGTGTCGTG CAGCCTCCAG GATCCCCCCT CCCGGGAGAG                    40

CCATAGTGGT CTGCGGAACC GGTGAGTACA CCGGAATTGC                    80

CAGGATGACC GGGTCCTTTC TTGGATTAAC CCGCTCAGTG                   120

CCTGGAGATT TGGGCGTGCC CCCGCGAGAC TGCTAGCCGA                   160

GTAGTGTTGG GTCGCGA                                            177

(2) INFORMATION FOR SEQ ID NO: 63:

(i) SEQUENCE CHARACTERISTICS:
              (A) LENGTH: 177 base pairs
              (B) TYPE: nucleic acid
              (C) STRANDEDNESS: single
              (D) TOPOLOGY: linear (ii) MOLECULE TYPE: cDNA (vii) IMMEDIATE SOURCE:
              (B) CLONE: be91

(viii) POSITION IN GENOME:
              (B) MAP POSITION: 5' untranslated region (xi) SEQUENCE DESCRIPTION: SEQ ID NO: 63:

GAGTGTCGTA CAGCCTCCAG GCCCCCCCCT CCCGGGAGAG                    40

CCATAGTGGT CTGCGGAACC GGTGAGTACA CCGGAATTGC                    80

CGGAAAGACT GGGTCCTTTC TTGGATAAAC CCACTCTATG                   120

TCCGGTCATT TGGGCGTGCC CCCGCAAGAC TGCTAGCCTA                   160

GTAGCGTTGG GTTGCGA                                            177

(2) INFORMATION FOR SEQ ID NO: 64:

(i) SEQUENCE CHARACTERISTICS:
              (A) LENGTH: 177 base pairs
              (B) TYPE: nucleic acid (C) STRANDEDNESS: single
        (D) TOPOLOGY: linear (ii) MOLECULE TYPE: cDNA (vii) IMMEDIATE SOURCE:
        (B) CLONE: be92

(viii) POSITION IN GENOME:
        (B) MAP POSITION: 5' untranslated region (xi) SEQUENCE DESCRIPTION: SEQ ID NO: 64:

```
GAGTGTCGTA CAGCCTCCAG GCCCCCCCCT CCCGGGAGAG                40
CCATAGTGGT CTGCGGAACC GGTGAGTACA CCGGAATTGC                80
CAGGAAGACT GGGTCCTTTC TTGGATAAAC CCACTCTATG               120
CCTGGTCATT TGGGCGTGCC CCCGCAAGAC TGCTAGCCGA               160
GTAGCGTTGG GTTGCGA                                        177
```

(2) INFORMATION FOR SEQ ID NO: 65:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: be93

(viii) POSITION IN GENOME:
        (B) MAP POSITION: 5' untranslated region (xi) SEQUENCE DESCRIPTION: SEQ ID NO: 65:

```
GAGTGTCGTG CAGCCTCCAG GCCCCCCCCT CCCGGGAGAG                40
CCATAGTGGT CTGCGGAACC GGTGAGTACA CCGGAATCGC                80
TGGGGTGACC GGGTCCTTTC TTGGAGCAAC CCGCTCAATA               120
CCCAGACATT TGGGCGTGCC CCCGCGAGAT CACTAGCCGA               160
GTAGTGTTGG GTCGCGA                                        177
```

(2) INFORMATION FOR SEQ ID NO: 66:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: be94

(viii) POSITION IN GENOME:
        (B) MAP POSITION: 5' untranslated region (xi) SEQUENCE DESCRIPTION: SEQ ID NO: 66:

```
GAGTGTCGTG CAGCCTCCAG GCCCCCCCCT CCCGGGAGAG                40
CCATAGTGGT CTGCGGAACC GGTGAGTACA CCGGAATCGC                80
TGGGGTGACC GGGTCCTTTC TTGGAGCAAC CCGCTCAATA               120
CCCAGACATT TGGGCGTGCC CCCGCAAGAT CACTAGCCGA               160
GTAGTGTTGG GTCGCGA                                        177
```

(2) INFORMATION FOR SEQ ID NO: 67:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: gb48

(viii) POSITION IN GENOME:
        (B) MAP POSITION: 5' untranslated region (xi) SEQUENCE DESCRIPTION: SEQ ID NO: 67:

```
GAGTGTTGTA CAGCCTCCAG GACCCCCCCT CCCGGGAGAG          40
CCATAGTGGT CTGCGGAACC GGTGAGTACA CCGGAATCGC          80
CGGGATGACC GGGTCCTTTC TTGGATAAAC CCGCTCAATG         120
CCCGGAAATT TGGGCGTGCC CCCGCAAGAC TGCTAGCCGA         160
GTAGTGTTGG GTCGCGA                                  177
```

(2) INFORMATION FOR SEQ ID NO: 68:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: gb116

(viii) POSITION IN GENOME:
        (B) MAP POSITION: 5' untranslated region (xi) SEQUENCE DESCRIPTION: SEQ ID NO: 68:

```
GAGTGTTGTA CAGCCTCCAG GACCCCCCCT CCCGGGAGAG          40
CCATAGTGGT CTGCGGAACC GGTGAGTACA CCGGAATCGC          80
CGGGATGACC GGGTCCTTTC TTGGATTAAC CCGCTCAATG         120
CCCGGAAATT TGGGCGTGCC CCCGCAAGAC TGCTAGCCGA         160
GTAGTGTTGG GTCGCGA                                  177
```

(2) INFORMATION FOR SEQ ID NO: 69:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: gb569

(viii) POSITION IN GENOME:
        (B) MAP POSITION: 5' untranslated region (xi) SEQUENCE DESCRIPTION: SEQ ID NO: 69:

```
GAGTGTTGTA CAGCCTCCAG GACCCCCCCT CCCGGGAGAG          40
```

```
CCATAGTGGT CTGCGGAACC GGTGAGTACA CCGGAATCGC                80

CGGGATGACC GGGTCCTTTC TTGGATAAAC CCGCTCAATG               120

CCCGGAAATT TGGGCGTGCC CCCGCAAGAC TGCTAGCCGA               160

GTAGTGTTGG GTCGCGA                                       177

(2) INFORMATION FOR SEQ ID NO: 70:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: gb358

(viii) POSITION IN GENOME:
        (B) MAP POSITION: 5' untranslated region (xi) SEQUENCE DESCRIPTION: SEQ ID NO: 70:

GAGTGTTGTA CAGCCTCCAG GACCCCCCCT CCCGGGAGAG                40

CCATAGTGGT CTGCGGAACC GGTGAGTACA CCGGAATCGC                80

CGGGATGACC GGGTCCTTTC TTGGATAAAC CCGCTCAATG               120

CCCGGAAATT TGGGCGTGCC CCCGCAAGAC TGCTAGCCGA               160

GTAGTGTTGG GTCGCGA                                       177

(2) INFORMATION FOR SEQ ID NO: 71:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: gb549

(viii) POSITION IN GENOME:
        (B) MAP POSITION: 5' untranslated region (xi) SEQUENCE DESCRIPTION: SEQ ID NO: 71:

GAGTGTTGTG CAGCCTCCAG GACCCCCCCT CCCGGGAGAG                40

CCATAGTGGT CTGCGGAACC GGTGAGTTCA CCGGAATCGC                80

CGGGACGACC GGGTCCTTTC TTGGAACAAA CCCGCTCAAT               120

GCCCGGCAAT TTGGGCGTGC CCCCGCAAGA CTGCTAGCCG               160

AGTAGTGTTG GGTCGCGA                                      178

(2) INFORMATION FOR SEQ ID NO: 72:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: cam600
```

-continued

```
        (viii) POSITION IN GENOME:
              (B) MAP POSITION: 5' untranslated region (xi) SEQUENCE DESCRIPTION: SEQ ID NO: 72:

GAGTGTTGTA CAGCCTCCAG GACCCCCCCT CCCGGGAGAG                          40

CCATAGTGGT CTGCGGAACC GGTGAGTACA CCGGAATCGC                          80

CGAGATGACC GGGTCCTTTC TTGGATCAAC CCGCTCAATG                         120

CTCGGAAATT TGGGCGTGCC CCCGCAAGAC TGCTAGCCGA                         160

GTAGTGTTGG GTCGCGA                                                  177

(2) INFORMATION FOR SEQ ID NO: 73:

(i) SEQUENCE CHARACTERISTICS:
             (A) LENGTH: 177 base pairs
             (B) TYPE: nucleic acid
             (C) STRANDEDNESS: single
             (D) TOPOLOGY: linear (ii) MOLECULE TYPE: cDNA (vii) IMMEDIATE SOURCE:
             (B) CLONE: cam736

(viii) POSITION IN GENOME:
             (B) MAP POSITION: 5' untranslated region (xi) SEQUENCE DESCRIPTION: SEQ ID NO: 73:

GAGTGTTGTA CAGCCTCCAG GACCCCCCCT CCCGGGAGAG                          40

CCATAGTGGT CTGCGGAACC GGTGAGTACA CCGGAATCGC                          80

CGAGATGACC GGGTCCTTTC TTGGATCAAC CCGCTCAATG                         120

CTCGGAAATT TGGGCGTGCC CCCGCAAGAC TGCTAGCCGA                         160

GTAGTGTTGG GTCGCGA                                                  177

(2) INFORMATION FOR SEQ ID NO: 74:

(i) SEQUENCE CHARACTERISTICS:
             (A) LENGTH: 177 base pairs
             (B) TYPE: nucleic acid
             (C) STRANDEDNESS: single
             (D) TOPOLOGY: linear (ii) MOLECULE TYPE: cDNA (vii) IMMEDIATE SOURCE:
             (B) CLONE: gb809

(viii) POSITION IN GENOME:
             (B) MAP POSITION: 5' untranslated region (xi) SEQUENCE DESCRIPTION: SEQ ID NO: 74:

GAGTGTTGTA CAGCCTCCAG GACCCCCCCT CCCGGGAGAG                          40

CCATAGTGGT CTGCGGAACC GGTGAGTACA CCGGAATCGC                          80

CGAGATGACC GGGTCCTTTC TTGGATCAAC CCGCTCAATG                         120

CTCGGAAATT TGGGCGTGCC CCCGCAAGAC CGCTAGCCGA                         160

GTAGTGTTGG GTCGCGA                                                  177

(2) INFORMATION FOR SEQ ID NO: 75:

(i) SEQUENCE CHARACTERISTICS:
             (A) LENGTH: 177 base pairs
             (B) TYPE: nucleic acid
             (C) STRANDEDNESS: single
```

```
        (D) TOPOLOGY: linear (ii) MOLECULE TYPE: cDNA (vii) IMMEDIATE SOURCE:
         (B) CLONE: gb487

(viii) POSITION IN GENOME:
         (B) MAP POSITION: 5' untranslated region (xi) SEQUENCE DESCRIPTION: SEQ ID NO: 75:

GAGTGTTGTA CAGCCTCCAG GACCCCCCCT CCCGGGAGAG           40

CCATAGTGGT CTGCGGAACC GGTGAGTACA CCGGAATCGC           80

CAGGATGACC GGGTCCTTTC TTGGATTAAC CCGCTCAATG          120

CCTGGAAATT TGGGCGTGCC CCCGCAAGAC TGCTAGCCGA          160

GTAGTGTTGG GTCGCGA                                   177

(2) INFORMATION FOR SEQ ID NO: 76:

(i) SEQUENCE CHARACTERISTICS:
         (A) LENGTH: 177 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (B) CLONE: gb724

(viii) POSITION IN GENOME:
         (B) MAP POSITION: 5' untranslated region (xi) SEQUENCE DESCRIPTION: SEQ ID NO: 76:

GAGTGTCGTA CAGCCTCCAG GACCCCCCCT CCCGGGAGAG           40

CCATAGTGGT CTGCGGAACC GGTGAGTTCA CCGGAATCGC           80

CAGGACGACC GGGTCCTTTC TTGGATTAAC CCGCTCAATG          120

CCTGGAAATT TGGGCGTGCC CCCGCAAGAC TGCTAGCCGA          160

GTAGTGTTGG GTCGCGA                                   177

(2) INFORMATION FOR SEQ ID NO: 77:

(i) SEQUENCE CHARACTERISTICS:
         (A) LENGTH: 177 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (A) LIBRARY: be97

(viii) POSITION IN GENOME:
         (B) MAP POSITION: 5' untranslated region (xi) SEQUENCE DESCRIPTION: SEQ ID NO: 77:

GAGTGTTGTA CAGCCTCCAG GACCCCCCCT CCCGGGAGAG           40

CCATAGTGGT CTGCGGAACC GGTGAGTACA CCGGAATCGC           80

CAGGACGACC GGGTCCTTTC TTGGATTAAC CCGCTCAATG          120

CCTGGAAATT TGGGCGTGCC CCCGCAAGAC TGCTAGCCGA          160

GTAGTGTTGG GTCGCGA                                   177
```

(2) INFORMATION FOR SEQ ID NO: 78:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: be95

(viii) POSITION IN GENOME:
        (B) MAP POSITION: 5' untranslated region (xi) SEQUENCE DESCRIPTION: SEQ ID NO: 78:

```
GAGTGTCGAA CAGCCTCCAG GACCCCCCCT CCCGGGAGAG                    40

CCATAGTGGT CTGCGGAACC GGTGAGTACA CCGGAATTGC                    80

CGGGATGACC GGGTCCTTTC TTGGATTAAC CCGCTCAATG                   120

CCCGGAGATT TGGGCGTGCC CCCGCGAGAC TGCTAGCCGA                   160

GTAGTGTTGG GTCGCGA                                            177
```

(2) INFORMATION FOR SEQ ID NO: 79:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: be96

(viii) POSITION IN GENOME:
        (B) MAP POSITION: 5' untranslated region (xi) SEQUENCE DESCRIPTION: SEQ ID NO: 79:

```
GAGTGTCGAA CAGCCTCCAG GACCCCCCCT CCCGGGAGAG                    40

CCATAGTGGT CTGCGGAACC GGTGAGTACA CCGGAATTGC                    80

CGGGACGACC GGGTCCTTTC TTGGATAAAC CCGCTCAATG                   120

CCCGGAGATT TGGGCGTGCC CCCGCGAGAC TGCTAGCCGA                   160

GTAGTGTTGG GTCGCGA                                            177
```

(2) INFORMATION FOR SEQ ID NO: 80:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: be98

(viii) POSITION IN GENOME:
        (B) MAP POSITION: 5' untranslated region (xi) SEQUENCE DESCRIPTION: SEQ ID NO: 80:

```
GAGTGTCGTG CAGCCTCCAG GACCCCCCCT CCCGGGAGAG                    40

CCATAGTGGT CTGCGGAACC GGTGAGTACA CCGGAATCGC                    80
```

```
CGGGTTGACC GGGTCCTTTC TTGGAACTAC CCGCTCAATG                    120

CCCGGAAATT TGGGCGTGCC CCCGCGAGAC TGCTAGCCGA                    160

GTAGTGTTGG GTCGCGA                                             177

(2) INFORMATION FOR SEQ ID NO: 81:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: gb438

(viii) POSITION IN GENOME:
        (B) MAP POSITION: 5' untranslated region (xi) SEQUENCE DESCRIPTION: SEQ ID NO: 81:

GAGTGTCGAA CAGCCTCCAG GATCCCCCCT CCCGGGAGAG                     40

CCATAGTGGT CTGCGGAACC GGTGAGTTCA CCGGAATCGC                     80

CGGGATGACC GGGTCCTTTC TTGGAATCAA CCCGCTCAAT                    120

GCCCGGAAAT TTGGGCGTGC CCCCGCGAGA CTGCTAGCCG                    160

AGTAGTGTTG GGTCGCGA                                            178

(2) INFORMATION FOR SEQ ID NO: 82:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: be90

(viii) POSITION IN GENOME:
        (B) MAP POSITION: ns5

(xi) SEQUENCE DESCRIPTION: SEQ ID NO: 82:

Ser Thr Val Thr Glu Asn Asp Ile Arg Val Glu Glu
1               5                   10

Ser Ile Tyr Gln Cys Cys Asp Leu Ala Pro Glu Ala
            15                  20

Arg Gln Ala Ile Lys Ser Leu Thr Glu Arg Leu Tyr
25                  30                  35

Ile Gly Gly Pro Leu Thr Asn Ser Lys Gly Gln Asn
            40                  45

Cys Gly Tyr Arg Arg Cys Arg Ala Ser Gly Val Leu
            50                  55              60

Thr Thr Ser Cys Gly Asn Thr Leu Thr Cys Tyr Leu
                65                  70

Lys Ala Ser Ala Ala Cys Arg Ala Ala Lys Leu Gln
            75                  80

Asp Cys Thr Met Leu Val Cys Gly Asp Asp Leu Val
85                  90                  95

Val Ile Cys Glu Ser Ala Gly Thr Gln Glu Asp Ala
```

```
                     100                 105
Ala Ser Leu Arg Val
            110

(2) INFORMATION FOR SEQ ID NO: 83:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: be91

(viii) POSITION IN GENOME:
        (B) MAP POSITION: ns5

(xi) SEQUENCE DESCRIPTION: SEQ ID NO: 83:

Ser Thr Val Thr Glu Arg Asp Ile Arg Thr Glu Glu
 1               5                  10

Ser Ile Tyr Gln Ala Cys Ser Leu Pro Gln Glu Ala
            15                  20

Arg Thr Val Ile His Ser Leu Thr Glu Arg Leu Tyr
25                  30                  35

Val Gly Gly Pro Met Ile Asn Ser Lys Gly Gln Ser
                40                  45

Cys Gly Tyr Arg Arg Cys Arg Ala Ser Gly Val Phe
        50                  55                  60

Thr Thr Ser Met Gly Asn Thr Met Thr Cys Tyr Ile
                    65                  70

Lys Ala Leu Ala Ala Cys Lys Ala Ala Gly Ile Val
            75                  80

Asp Pro Val Met Leu Val Cys Gly Asp Asp Leu Val
85                  90                  95

Val Ile Ser Glu Ser Gln Gly Asn Glu Glu Asp Glu
                100                 105

Arg Asn Leu Arg Ala
            110

(2) INFORMATION FOR SEQ ID NO: 84:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: be92

(viii) POSITION IN GENOME:
        (B) MAP POSITION: ns5

(xi) SEQUENCE DESCRIPTION: SEQ ID NO: 84:

Ser Thr Val Thr Glu Arg Asp Ile Arg Thr Glu Glu
 1               5                  10

Ser Ile Tyr Leu Ala Cys Ser Leu Pro Glu Gln Ala
            15                  20

Arg Thr Ala Ile His Ser Leu Thr Glu Arg Leu Tyr
```

```
                 25                  30                  35
Val Gly Gly Pro Met Leu Asn Ser Lys Gly Gln Thr
                 40                  45

Cys Gly Tyr Arg Arg Cys Arg Ala Ser Gly Val Phe
                 50                  55                  60

Thr Thr Ser Met Gly Asn Thr Ile Thr Cys Tyr Val
                         65                  70

Lys Ala Gln Ala Ala Cys Lys Ala Ala Gly Ile Ile
                 75                  80

Ala Pro Thr Met Leu Val Cys Gly Asp Asp Leu Val
 85                  90                  95

Val Ile Ser Glu Ser Gln Gly Thr Glu Glu Asp Glu
                100                 105

Arg Asn Leu Arg Ala
        110

(2) INFORMATION FOR SEQ ID NO: 85:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: be93

(viii) POSITION IN GENOME:
        (B) MAP POSITION: ns5

(xi) SEQUENCE DESCRIPTION: SEQ ID NO: 85:

Ser Thr Val Thr Glu Gln Asp Ile Arg Val Glu Glu
1               5                   10

Glu Ile Tyr Gln Cys Cys Asn Leu Glu Pro Glu Ala
                15                  20

Arg Lys Val Ile Ser Ser Leu Thr Glu Arg Leu Tyr
 25                  30                  35

Cys Gly Gly Pro Met Phe Asn Ser Lys Gly Ala Gln
                 40                  45

Cys Gly Tyr Arg Arg Cys Arg Ala Ser Gly Val Leu
                 50                  55                  60

Pro Thr Ser Phe Gly Asn Thr Ile Thr Cys Tyr Ile
                         65                  70

Lys Ala Thr Thr Ala Ala Lys Ala Ala Gly Leu Arg
                 75                  80

Asn Pro Asp Phe Leu Val Cys Gly Asp Asp Leu Val
 85                  90                  95

Val Val Ala Glu Ser Asp Gly Val Asp Glu Asp Arg
                100                 105

Ala Ala Leu Arg Ala
        110

(2) INFORMATION FOR SEQ ID NO: 86:

(i) SEQUENCE CHARACTERISTICS:
        (A) LENGTH: 113 amino acids
        (B) TYPE: amino acid
        (C) STRANDEDNESS: single
        (D) TOPOLOGY: linear
```

```
    (ii) MOLECULE TYPE: protein (vii) IMMEDIATE SOURCE:
             (B) CLONE: gb48

(viii) POSITION IN GENOME:
             (B) MAP POSITION: ns5

(xi) SEQUENCE DESCRIPTION: SEQ ID NO: 86:

Ser Thr Val Thr Glu Lys Asp Ile Arg Val Glu Glu
1               5                   10

Glu Val Tyr Gln Cys Cys Asp Leu Gly Pro Glu Ala
            15                  20

Arg Lys Ala Ile Thr Ala Leu Thr Glu Arg Leu Tyr
25                  30                  35

Val Gly Gly Pro Met His Asn Ser Lys Gly Asp Leu
                40                  45

Cys Gly Tyr Arg Arg Cys Arg Ala Ser Gly Val Tyr
    50                  55                  60

Thr Thr Ser Phe Gly Asn Thr Leu Thr Cys Tyr Leu
                65                  70

Lys Ala Ser Ala Ala Ile Lys Ala Ala Gly Leu Arg
                75                  80

Asp Cys Thr Met Leu Val Cys Gly Asp Asp Leu Val
85                  90                  95

Val Ile Ala Glu Ser Asp Gly Val Glu Glu Asp Lys
                100                 105

Arg Pro Leu Gly Ala
    110

(2) INFORMATION FOR SEQ ID NO: 87:

(i) SEQUENCE CHARACTERISTICS:
            (A) LENGTH: 113 amino acids
            (B) TYPE: amino acid
            (C) STRANDEDNESS: single
            (D) TOPOLOGY: linear (ii) MOLECULE TYPE: protein (vii) IMMEDIATE SOURCE:
             (B) CLONE: gb116

(viii) POSITION IN GENOME:
             (B) MAP POSITION: ns5

(xi) SEQUENCE DESCRIPTION: SEQ ID NO: 87:

Ser Thr Val Thr Glu Lys Asp Ile Arg Val Glu Glu
1               5                   10

Glu Val Tyr Gln Cys Cys Asp Leu Gly Pro Glu Ala
            15                  20

Arg Arg Ala Ile Thr Ala Leu Thr Glu Arg Leu Tyr
25                  30                  35

Val Gly Gly Pro Met His Asn Ser Arg Gly Asp Leu
                40                  45

Cys Gly Tyr Arg Arg Cys Arg Ala Ser Gly Val Tyr
    50                  55                  60

Thr Thr Ser Phe Gly Asn Thr Leu Thr Cys Tyr Leu
                65                  70

Lys Ala Ser Ala Ala Ile Arg Ala Ala Gly Leu Arg
                75                  80
```

```
Asp Cys Thr Met Leu Val Cys Gly Asp Asp Leu Val
85                  90                  95

Val Ile Ala Glu Ser Asp Gly Val Glu Glu Asp Lys
            100                 105

Arg Ala Leu Gly Ala
    110
```

(2) INFORMATION FOR SEQ ID NO: 88:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: gb215

(viii) POSITION IN GENOME:
        (B) MAP POSITION: ns5

(xi) SEQUENCE DESCRIPTION: SEQ ID NO: 88:

```
Ser Thr Val Thr Glu Lys Asp Ile Arg Val Glu Glu
1               5                   10

Glu Val Tyr Gln Cys Cys Asp Leu Glu Pro Glu Ala
            15                  20

Arg Lys Val Ile Thr Ala Leu Thr Glu Arg Leu Tyr
25                  30                  35

Val Gly Gly Pro Met His Asn Ser Lys Gly Asp Leu
            40                  45

Cys Gly Tyr Arg Arg Cys Arg Ala Ser Gly Val Tyr
    50                  55                  60

Thr Thr Ser Phe Gly Asn Thr Leu Thr Cys Tyr Leu
            65                  70

Lys Ala Ser Ala Ala Ile Arg Ala Ser Gly Leu Arg
    75                  80

Asp Cys Thr Met Leu Val Tyr Gly Asp Asp Leu Val
85                  90                  95

Val Ile Ala Glu Ser Asp Gly Val Glu Glu Asp Lys
            100                 105

Arg Ala Leu Gly Val
    110
```

(2) INFORMATION FOR SEQ ID NO: 89:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: gb358

(viii) POSITION IN GENOME:
        (B) MAP POSITION: ns5

(xi) SEQUENCE DESCRIPTION: SEQ ID NO: 89:

```
Ser Thr Val Thr Glu Lys Asp Ile Arg Val Glu Glu
1               5                   10
```

```
Glu Val Tyr Gln Cys Cys Asp Leu Glu Pro Glu Ala
         15                  20

Arg Lys Ala Ile Thr Ala Leu Thr Glu Arg Leu Tyr
25                  30                  35

Val Gly Gly Pro Met His Asn Ser Lys Gly Asp Leu
             40                  45

Cys Gly Tyr Arg Arg Cys Arg Ala Ser Gly Val Tyr
     50                  55                  60

Thr Thr Ser Phe Gly Asn Thr Leu Thr Cys Tyr Leu
                 65                  70

Lys Ala Ser Ala Ala Ile Arg Ala Ala Gly Leu Arg
         75                  80

Asp Cys Thr Met Leu Val Cys Gly Asp Asp Leu Val
85                  90                  95

Val Ile Ala Glu Ser Asp Gly Val Glu Glu Asp Lys
                100                 105

Arg Ala Leu Gly Ala
         110
```

(2) INFORMATION FOR SEQ ID NO: 90:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: gb549

(viii) POSITION IN GENOME:
        (B) MAP POSITION: ns5

(xi) SEQUENCE DESCRIPTION: SEQ ID NO: 90:

```
Ser Thr Val Thr Glu Arg Asp Ile Arg Thr Glu Glu
1                5                  10

Glu Ile Tyr Gln Cys Cys Asp Leu Glu Pro Glu Ala
         15                  20

Arg Lys Val Ile Ser Ala Leu Thr Glu Arg Leu Tyr
25                  30                  35

Val Gly Gly Pro Met Tyr Asn Ser Lys Gly Asp Leu
             40                  45

Cys Gly Gln Arg Arg Cys Arg Ala Ser Gly Val Tyr
     50                  55                  60

Thr Thr Ser Phe Gly Asn Thr Val Thr Cys Tyr Leu
                 65                  70

Lys Ala Val Ala Ala Thr Arg Ala Ala Gly Leu Lys
         75                  80

Gly Cys Ser Met Leu Val Cys Gly Asp Asp Leu Val
85                  90                  95

Val Ile Cys Glu Ser Gly Gly Val Glu Glu Asp Ala
                100                 105

Arg Ala Leu Arg Ala
         110
```

(2) INFORMATION FOR SEQ ID NO: 91:

```
        (i) SEQUENCE CHARACTERISTICS:
            (A) LENGTH: 113 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (vi) ORIGINAL SOURCE:
            (C) INDIVIDUAL ISOLATE: gb809

(xi) SEQUENCE DESCRIPTION: SEQ ID NO: 91:

Ser Thr Val Thr Glu Arg Asp Ile Lys Val Glu Glu
1               5                  10

Glu Val Tyr Gln Cys Cys Asp Leu Glu Pro Glu Ala
            15                  20

Arg Lys Val Ile Ala Ala Leu Thr Glu Arg Leu Tyr
25                  30                  35

Val Gly Gly Pro Met His Asn Ser Lys Gly Asp Leu
                40                  45

Cys Gly Tyr Arg Arg Cys Arg Ala Ser Gly Val Tyr
    50                  55                  60

Thr Thr Ser Phe Gly Asn Thr Met Thr Cys Tyr Leu
                65                  70

Lys Ala Ser Ala Ala Ile Arg Ala Ala Gly Leu Lys
                75                  80

Asp Cys Thr Met Leu Val Cys Gly Asp Asp Leu Val
85                  90                  95

Val Ile Ala Glu Ser Gly Gly Val Glu Glu Asp Lys
                100                 105

Arg Ala Leu Gly Ala
        110

(2) INFORMATION FOR SEQ ID NO: 92:

(i) SEQUENCE CHARACTERISTICS:
            (A) LENGTH: 113 amino acids
            (B) TYPE: amino acid
            (C) STRANDEDNESS: single
            (D) TOPOLOGY: linear (ii) MOLECULE TYPE: protein (vii) IMMEDIATE SOURCE:
            (B) CLONE: be95

(viii) POSITION IN GENOME:
            (B) MAP POSITION: ns5

(xi) SEQUENCE DESCRIPTION: SEQ ID NO: 92:

Ser Thr Val Thr Glu His Asp Ile Met Thr Glu Glu
1               5                  10

Ser Ile Tyr Gln Ser Cys Asp Leu Gln Pro Glu Ala
            15                  20

Arg Ala Ala Ile Arg Ser Leu Thr Gln Arg Leu Tyr
25                  30                  35

Cys Gly Gly Pro Met Tyr Asn Ser Lys Gly Gln Gln
                40                  45

Cys Gly Tyr Arg Arg Cys Arg Ala Ser Gly Val Phe
    50                  55                  60
```

```
Thr Thr Ser Met Gly Asn Thr Met Thr Cys Tyr Ile
            65                  70
Lys Ala Leu Ala Ser Cys Arg Ala Ala Arg Leu Arg
        75                  80
Asp Cys Thr Leu Leu Val Cys Gly Asp Asp Leu Val
85                  90                  95
Ala Ile Cys Glu Ser Gln Gly Thr His Glu Asp Glu
            100                 105
Ala Ser Leu Arg Ala
        110
```

(2) INFORMATION FOR SEQ ID NO: 93:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 93:

GAGTGTTGTA CAGCCTCC                                     18

(2) INFORMATION FOR SEQ ID NO: 94:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 94:

TGCCCGGAAA TTTGGGC                                      17

(2) INFORMATION FOR SEQ ID NO: 95:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 95:

TGCCCGGAGA TTTGGG                                       16

(2) INFORMATION FOR SEQ ID NO: 96:

(i) SEQUENCE CHARACTERISTICS:
        (A) LENGTH: 17 base pairs
        (B) TYPE: nucleic acid
        (C) STRANDEDNESS: single
        (D) TOPOLOGY: linear

```
        (ii)  MOLECULE TYPE: cDNA (iii) HYPOTHETICAL: NO (iv)  ANTI-SENSE: NO (xi)  SEQUENCE DESCRIPTION: SEQ ID NO: 96:

GAGTGTGGAA CAGCCTC                                                                17

(2) INFORMATION FOR SEQ ID NO: 97:

(i)   SEQUENCE CHARACTERISTICS:
              (A) LENGTH: 16 base pairs
              (B) TYPE: nucleic acid
              (C) STRANDEDNESS: single
              (D) TOPOLOGY: linear (ii)  MOLECULE TYPE: cDNA (iii) HYPOTHETICAL: NO (iv)  ANTI-SENSE: YES (xi)  SEQUENCE DESCRIPTION: SEQ ID NO: 97:

GGGGGCCTGG AGGCTG                                                                 16
```